United States Patent
Maurer, Jr. et al.

(10) Patent No.: US 9,895,555 B2
(45) Date of Patent: Feb. 20, 2018

(54) IMAGING METHODS FOR IMAGE-GUIDED RADIATION TREATMENT

(71) Applicant: ACCURAY INCORPORATED, Sunnyvale, CA (US)

(72) Inventors: Calvin R. Maurer, Jr., San Jose, CA (US); Mu Young Lee, San Jose, CA (US); Gopinath Kuduvalli, San Jose, CA (US); Petr Jordan, Redwood City, CA (US); Prashant Chopra, Sunnyvale, CA (US)

(73) Assignee: Accuray Incorporated, Sunnyvale, CA (US)

( * ) Notice: Subject to any disclaimer, the term of this patent is extended or adjusted under 35 U.S.C. 154(b) by 469 days.

(21) Appl. No.: 14/446,136

(22) Filed: Jul. 29, 2014

(65) Prior Publication Data

US 2015/0016586 A1 Jan. 15, 2015

Related U.S. Application Data

(62) Division of application No. 13/156,299, filed on Jun. 8, 2011, now Pat. No. 8,804,901.
(Continued)

(51) Int. Cl.
*A61N 5/10* (2006.01)
*G06T 7/00* (2017.01)
(Continued)

(52) U.S. Cl.
CPC ........... *A61N 5/1067* (2013.01); *A61B 6/025* (2013.01); *A61B 6/032* (2013.01); *A61B 6/4014* (2013.01); *A61B 6/4071* (2013.01); *A61B 6/4085* (2013.01); *A61B 6/4458* (2013.01); *A61B 6/482* (2013.01); *A61B 6/488* (2013.01); *A61N 5/1049* (2013.01); *G06T 7/0014* (2013.01);
(Continued)

(58) Field of Classification Search
CPC .................... A61N 5/1049; A61N 2005/1061
See application file for complete search history.

(56) References Cited

U.S. PATENT DOCUMENTS 5,099,134 A 3/1992 Hase
5,818,902 A 10/1998 Yu
(Continued)

FOREIGN PATENT DOCUMENTS

DE 102008030893 12/2009
EP 2058027 5/2009
(Continued)

OTHER PUBLICATIONS

Badea, Christian C., Volume Imaging Using a Combined Cone Beam CT-DTS Approach, Doctorate Thesis, University of Patras (2000), 123 pages.
(Continued)

*Primary Examiner* — Hoon Song
(74) *Attorney, Agent, or Firm* — Womble Bond Dickinson (US) LLP

(57) ABSTRACT

An IGRT system and methods are described embodiments of which perform selectively integration of x-ray source arrays, dual-energy imaging, stereoscopic imaging, static and source collimation, or inverse geometry tomosynthesis imaging to acquire or track a target during radiation treatment.

21 Claims, 29 Drawing Sheets

FIG. 1

Related U.S. Application Data

(60) Provisional application No. 61/352,637, filed on Jun. 8, 2010, provisional application No. 61/371,733, filed on Aug. 8, 2010.

(51) Int. Cl.
*A61B 6/02* (2006.01)
*A61B 6/03* (2006.01)
*A61B 6/00* (2006.01)
*G06T 7/70* (2017.01)

(52) U.S. Cl.
CPC .............. *G06T 7/70* (2017.01); *A61N 5/1083* (2013.01); *A61N 2005/1061* (2013.01); *G06T 2200/04* (2013.01); *G06T 2207/10112* (2013.01); *G06T 2207/30004* (2013.01)

(56) References Cited

U.S. PATENT DOCUMENTS

| | | | |
|---|---|---|---|
| 6,075,840 A | 6/2000 | Pellegrino | |
| 6,501,981 B1 | 12/2002 | Schweikard et al. | |
| 6,647,092 B2 | 11/2003 | Eberhard | |
| 6,778,850 B1 | 8/2004 | Adler | |
| 6,865,254 B2 | 3/2005 | Nafstadius | |
| 6,885,724 B2 | 4/2005 | Li | |
| 6,969,194 B1 | 11/2005 | Nafstadius | |
| 6,973,158 B2 | 12/2005 | Besson | |
| 6,973,202 B2 | 12/2005 | Mostafavi | |
| 6,977,987 B2 | 12/2005 | Yamashita | |
| 7,085,347 B2 | 8/2006 | Mihara | |
| 7,142,633 B2 | 11/2006 | Eberhard | |
| 7,162,008 B2 | 1/2007 | Earl | |
| 7,188,999 B2 | 3/2007 | Mihara et al. | |
| 7,204,640 B2 | 4/2007 | Fu et al. | |
| 7,227,925 B1 | 6/2007 | Mansfield et al. | |
| 7,231,017 B2 | 6/2007 | Gertsenshteyn | |
| 7,246,943 B2 | 7/2007 | Gotoh | |
| 7,302,033 B2 | 11/2007 | Carrano | |
| 7,345,282 B2 | 3/2008 | Hawman | |
| 7,388,940 B1 | 6/2008 | De Man | |
| 7,440,603 B2 | 10/2008 | Eberhard | |
| 7,444,011 B2 | 10/2008 | Pan et al. | |
| 7,446,328 B2 | 11/2008 | Rigney | |
| 7,471,765 B2 | 12/2008 | Jaffray et al. | |
| 7,505,562 B2 | 3/2009 | Dinca et al. | |
| 7,519,151 B1 | 4/2009 | Shukla | |
| 7,532,705 B2 | 5/2009 | Yin et al. | |
| 7,564,945 B2 | 7/2009 | Kim | |
| 7,567,647 B1 | 7/2009 | Maltz | |
| 7,623,623 B2 | 11/2009 | Raanes | |
| 7,639,777 B2 | 12/2009 | Warner | |
| 7,657,304 B2 | 2/2010 | Mansfield | |
| 7,684,647 B2 | 3/2010 | Fu et al. | |
| 7,693,257 B2 | 4/2010 | Allison | |
| 7,711,087 B2 | 5/2010 | Mostafavi | |
| 7,945,014 B2 * | 5/2011 | Mertelmeier | A61B 6/025 378/21 |
| 7,961,838 B2 | 6/2011 | Yin | |
| 2002/0154728 A1 | 10/2002 | Morita et al. | |
| 2005/0049478 A1 | 3/2005 | Kuduvalli et al. | |
| 2005/0078861 A1 | 4/2005 | Usikov | |
| 2005/0117708 A1 | 6/2005 | Cho | |
| 2005/0226364 A1 | 10/2005 | De Man | |
| 2006/0002509 A1 | 1/2006 | Claus et al. | |
| 2006/0008047 A1 | 1/2006 | Zhou | |
| 2006/0098855 A1 | 5/2006 | Gkanatsios et al. | |
| 2006/0210015 A1 | 9/2006 | Pelc | |
| 2007/0003123 A1 | 1/2007 | Fu | |
| 2007/0076846 A1 | 4/2007 | Ruchala | |
| 2007/0116175 A1 | 5/2007 | Zhang et al. | |
| 2007/0237290 A1 | 10/2007 | Mostafavi | |
| 2007/0291895 A1 | 12/2007 | Yin et al. | |
| 2008/0056435 A1 | 3/2008 | Basu et al. | |
| 2008/0130825 A1 | 6/2008 | Fu et al. | |
| 2008/0240350 A1 | 10/2008 | Moyers | |
| 2008/0260093 A1 | 10/2008 | Bontus | |
| 2009/0067579 A1 | 3/2009 | Mansfield | |
| 2009/0110238 A1 | 4/2009 | Li | |
| 2009/0116616 A1 | 5/2009 | Lu | |
| 2009/0175562 A1 | 7/2009 | Pan et al. | |
| 2009/0180666 A1 | 7/2009 | Sheng | |
| 2009/0189591 A1 | 7/2009 | Lu | |
| 2009/0296886 A1 | 12/2009 | Maltz et al. | |
| 2009/0297011 A1 | 12/2009 | Brunner | |
| 2010/0020931 A1 | 1/2010 | Otto | |
| 2010/0067739 A1 | 3/2010 | Mostafavi | |
| 2010/0069742 A1 | 3/2010 | Partain | |
| 2010/0091938 A1 | 4/2010 | Fadler | |
| 2010/0128839 A1 | 5/2010 | Partain | |
| 2010/0329413 A1 | 12/2010 | Zhou et al. | |
| 2011/0075794 A1 | 3/2011 | Boese et al. | |
| 2014/0247919 A1 * | 9/2014 | Zhang | A61B 6/025 378/62 |

FOREIGN PATENT DOCUMENTS

| | | |
|---|---|---|
| EP | 1472702 | 12/2009 |
| WO | 2009/012453 | 1/2009 |
| WO | 2010/030397 | 3/2010 |

OTHER PUBLICATIONS

Chen, Y. et al., Impulse Response Analysis for Several Digital Tomosynthesis Mammography Reconstructions Algorithms, Medical Imaging 2005: Physics of Medical Imaging, Michael J. Flynn, ed., Proceedings of SPIE vol. 5745, pp. 541-549 (2005).

Godfrey, D., et al., Digital Tomosynthesis With an On-Board Kilovoltage Imaging Device, Int. J. Radiation Oncology Biol. Phys., vol. 65, No. 1, pp. 8-15 (2006).

Kamino, Y., et al., Development of a Four-Dimensional Image-Guided Radiotherapy System With a Gimbaled X-Ray Head, Int. J. Radiation Oncology Biol. Phys., vol. 66, No. 1, pp. 271-278 (2006).

Kamino, Y., et al., Development of a New Concept Automatic Frequency Controller for an Ultrasmall C-Band Linear Accelerator Guide, Med. Phys. 34 (8), pp. 3243-3248 (Aug. 2007).

Kamino, Y., et al., Development of an Ultrasmall C-Bind Linear Accelerator Guide for a Four-Dimensional Image-Guided Radiotherapy System With a Gimbaled X-Ray Head, Med. Phys. 34 (5), pp. 1797-1808 (May 2007).

Kilby et al., The CyberKnife® Robotic Radiosurgery System in 2010, Tech. in Cancer Res. and Treatment, vol. 9, No. 5, pp. 433-452 (2010).

Lalush, D., Three-Dimensional Tomosynthesis Reconstruction from 1D and 2D X-ray Source Arrays, 2006 IEEE Nuclear Science Symposium Conference Record, pp. 1670-1674 (2006).

Martin et al., Stereotactic Body Radiotherapy: A Review, Clinical Oncology, pp. 1-16 (2010).

Poulot, J., MV Cone Beam CT Imaging for Daily Localization: (Part II), AAPM CE-Therapy Series Panel Session, Jul. 28, 2009, downloaded from http://www.aapm.org/meetings/amos2/pdf/42-12003-41828-461.pdf on Mar. 23, 2010 (Jul. 28, 2009).

Quan, E., et al., Three-Dimensional Imaging Properties of Rotation-Free Square and Hexagonal Micro-CT Systems, IEEE Trans. Med. Imaging, vol. 29, No. 3, pp. 916-923 (Mar. 2010).

Wang, J., Accurate and Fast Localization of Prostate for External Beam Radiation Therapy, Annual Summary Prepared for U.S. Army Medical Research and Material Command, Fort Derrick MD, Award No. W81XWH-08-1-0127 (Mar. 2009).

Yang, G. et al., Stationary Digital Breast Tomosynthesis System With a Multi-Beam Field Emission X-ray Source Array, Medical Imaging 2008: Physics of Medical Imaging, Proc. SPIE 6913, 69131A (2008).

USPTO Notice of Allowance for U.S. Appl. No. 13/156,299, dated Apr. 3, 2014, 9 pages.

Greene et al. "A Constrained Non-Rigid Registration Algorithm for Application in Prostate Radiotherapy", Biomedical Imaging: From Nano to Macro, 2007, ISBI 2007, 4th IEEE International Sympo-

(56) References Cited

OTHER PUBLICATIONS sium on IEEE, Apr. 1, 2007, [retrieved Sep. 28, 2017 from https://www.ncbi.nlm.nih.gov/pmc/articles/PMC2792992/].

Ren Lei et al, "Automatic registration between reference and on-board digital tomosynthesis images for positioning verification", Medical Physics, AIP, Melville, NY, vol. 35, No. 2, Jan. 28, 2008, pp. 664-672.

Stellaray, Digitally Addressable Flat Panel X-ray Sources for Medical Imaging, Stellaray, Inc., 1-page document, www.stellar-ray.com(undated).

Triple Ring Technologies, Technology and Product Development: Focus on X-ray Technologies, 2-page document, www.tripleringtech.com (undated).

Wu et al. "On-Board Patient Positioning for Head-and-Neck IMRT: Comparing Digital Tomosynthesis to Kilovoltage Radiography and Con-Beam Computer Tomography", International Journal of Radiation: Oncology Biology Physics, Pergamon Press, USA, vol. 69, No. 2, Sep. 14, 2007, pp. 598-606.

XinRay Systems, Products and Technology: Distributed X-ray Source Technology, 2-page document, www.xinraysystems.com (undated).

Zhang et al., "Comparing Digital Tomosynthesis to Cone-beam CT for Position Verification in Patients Undergoing Partial Breast Irradiation", International Journal of Radiation: Oncology Bioloby Physics, Pergamon Press, USA, vol. 73, No. 3, Mar. 1, 2009, [retrieved Sep. 28, 2017 from https://www.ncbi.nlm.nih.gov/pmc/articles/PMC2685874/].

PCT/2011/039678; International Search Report dated Jan. 16, 2012, 6 pages.

PCT/2011/039678; Written Opinion dated Jan. 16, 2012, 12 pages.

\* cited by examiner

IMAGING METHODS FOR IMAGE-GUIDED RADIATION TREATMENT

CROSS-REFERENCE TO RELATED APPLICATIONS

This application is a divisional of U.S. patent application Ser. No. 13/156,299, filed Jun. 8, 2011, which claims priority to U.S. provisional application No. 61/352,637 filed Jun. 8, 2010 and U.S. provisional application No. 61/371,733 filed on Aug. 8, 2010, which are hereby incorporated by reference. This patent application is related to the commonly assigned U.S. application Ser. No. 13/033,584 filed on Feb. 23, 2011, which is incorporated by reference herein.

FIELD

This application relates to medical imaging and image guided radiation treatment. More particularly, this application relates to systems, methods, and related computer program products for x-ray based medical imaging and x-ray based image-guided radiation treatment.

BACKGROUND

Pathological anatomies such as tumors and lesions can be treated with an invasive procedure, such as surgery, which can be harmful and full of risks for the patient. A non-invasive method to treat a pathological anatomy (e.g., tumor, lesion, vascular malformation, nerve disorder, etc.) is external beam radiation therapy, which typically uses a therapeutic radiation source, such as a linear accelerator (LINAC), to generate radiation beams, such as x-rays. In one type of external beam radiation therapy, a therapeutic radiation source directs a sequence of x-ray beams at a tumor site from multiple co-planar angles, with the patient positioned so the tumor is at the center of rotation (isocenter) of the beam. As the angle of the therapeutic radiation source changes, every beam passes through the tumor site, but passes through a different area of healthy tissue on its way to and from the tumor. As a result, the cumulative radiation dose at the tumor is high and that to healthy tissue is relatively low.

The term "radiosurgery" refers to a procedure in which radiation is applied to a target region at doses sufficient to necrotize a pathology in fewer treatment sessions or fractions than with delivery of lower doses per fraction in a larger number of fractions. Radiosurgery is typically characterized, as distinguished from radiotherapy, by relatively high radiation doses per fraction (e.g., 500-2000 centiGray), extended treatment times per fraction (e.g., 30-60 minutes per treatment), and hypo-fractionation (e.g., one to five fractions or treatment days). Radiotherapy is typically characterized by a low dose per fraction (e.g., 100-200 centiGray), shorter fraction times (e.g., 10 to 30 minutes per treatment) and hyper-fractionation (e.g., 30 to 45 fractions). For convenience, the term "radiation treatment" is used herein to mean radiosurgery and/or radiotherapy unless otherwise noted.

Associated with each radiation therapy system is an imaging system to provide in-treatment images that are used to set up and, in some examples, guide the radiation delivery procedure and track in-treatment target motion. Portal imaging systems place a detector opposite the therapeutic source itself to image the patient for setup and in-treatment images, while other approaches utilize distinct, independent image radiation source(s) and detector(s) for the patient set-up and in-treatment images. Target or target volume tracking during treatment is accomplished by comparing in-treatment images to pre-treatment image information. Pre-treatment image information may comprise, for example, computed tomography (CT) data, cone-beam CT (CBCT) data, magnetic resonance imaging (MRI) data, positron emission tomography (PET) data or 3D rotational angiography (3DRA) data, and any information obtained from these imaging modalities (for example and without limitation digitally reconstructed radiographs or DRRs).

In one common scenario, the therapeutic source is a linear accelerator (LINAC) producing therapeutic radiation (which can be termed an "MV source") and the imaging system comprises one or more independent x-ray imaging sources producing relatively low intensity lower energy imaging radiation (each of which can be termed a "kV source"). In-treatment images can comprise one or more (preferably two) two-dimensional images (typically x-ray) acquired at one or more different points of view (e.g., stereoscopic x-ray images), and are compared with two-dimensional DRRs derived from the three dimensional pre-treatment image information. A DRR is a synthetic x-ray image generated by casting rays through the 3D imaging data, where the rays simulate the geometry of the in-treatment x-ray imaging system. The resulting DRR then has approximately the same scale and point of view as the in-treatment x-ray imaging system, and can be compared with the in-treatment x-ray images to determine the position and orientation of the target, which is then used to guide delivery of radiation to the target.

X-ray tomosynthesis refers to the process of acquiring a number of two-dimensional x-ray projection images of a target volume using x-rays that are incident upon the target volume at a respective number of different angles, followed by the mathematical processing of the two-dimensional x-ray projection images to yield a set of one or more tomosynthesis reconstructed images representative of one or more respective slices of the target volume, wherein the number of x-ray projection images is less than that in a set that would be required for CT image reconstruction, and/or the number or range of incident radiation angles is less than would be used in a CT imaging procedure. Commonly, a plurality of tomosynthesis reconstructed images are generated, each being representative of a different slice of the target volume, and therefore a set of tomosynthesis reconstructed images is sometimes referred to as a tomosynthesis volume. As used herein, the term tomosynthesis projection image refers to one of the two-dimensional x-ray projection images acquired during the tomosynthesis imaging process.

For purposes of the above terminology, for some preferred embodiments, a set of images that is required for CT image reconstruction is considered to include images (e.g., 300 or more) generated over a range of incident angles that is 180 degrees plus the fan beam angle. For some preferred embodiments, the x-ray projection images for constructing a tomosynthesis image are taken over an angular range between 1 degree and an angular range value that is less than that needed for a complete projection set for CT imaging (e.g., 180 degrees plus the fan angle), wherein the number of projection images generated in this range is a value that is between 2 and 1000. In other preferred embodiments, the x-ray projection images for constructing a tomosynthesis image are taken over an angular range of between 5 degrees and 45 degrees, wherein the number of projection images generated in this range is between 5 and 100.

X-ray tomosynthesis has been proposed as an in-treatment kV imaging modality for use in conjunction with radiation treatment systems. In U.S. Pat. No. 7,532,704B1 it is proposed to process the three-dimensional pre-treatment image information (e.g., a planning CT image volume) to generate digital tomosynthesis (DTS) reference image data of a target located within or on a patient, such as by simulating x-ray cone-beam projections through the planning CT image volume. Subsequently, with the patient on the treatment bed, DTS verification images are generated by acquiring a number of x-ray cone beam images at different angles. Target localization is then performed by comparing landmarks, such as bony structures, soft-tissue anatomy, implanted targets, and skin contours in the DTS reference image data and DTS verification image data. In U.S. Pat. No. 7,711, 087B2 it is proposed to acquire tomosynthesis image data during a treatment session. For purposes of movement tracking during the treatment session, tomosynthesis reconstructed slices are processed directly in conjunction with reference CT data in a process that searches for a tomosynthesis reconstructed image that best matches a selected reference CT slice. The identity of the particular tomosynthesis reconstructed image that yields a maximum degree of match, together with the amount of spatial offset required for that tomosynthesis reconstructed image to achieve the peak match, is used to localize the target in three-dimensional space.

Cone beam CT (CBCT) has also been proposed as an in-treatment imaging modality for use in conjunction with radiation treatment systems, in some cases as a kV imaging modality and in other cases as an MV (portal) imaging modality. Whereas conventional CT imaging reconstructs 2D slices from 1D projections through a target volume, the 2D slices then being stacked to form a 3D volumetric image, CBCT imaging directly constructs a 3D volumetric image from 2D projections of the target volume. As known in the art, CBCT offers the ability to form a 3D image volume from a single gantry rotation about the target volume, whereas conventional CT requires one rotation per slice (for single-row detectors) or 1/M rotations per slice (for newer quasi-linear multi-row detectors having M rows). CBCT also provides for a more isotropic spatial resolution, whereas conventional CT limits the spatial resolution in the longitudinal direction to the slice thickness. However, because conventional CT systems usually offer a substantially higher degree of collimation near their linear or quasi-linear row detectors than can usually be afforded by CBCT systems near their two-dimensional detectors, scattering noise and artifacts are more of a problem for CBCT systems than for conventional CT systems.

In U.S. Pat. No. 7,471,765B2 it is proposed to use a CBCT imaging system including a kV x-ray tube and a flat-panel imaging detector mounted on a LINAC gantry such that the kV radiation is approximately orthogonal to the MV treatment radiation from the LINAC. Prior to treatment, a CBCT planning image is acquired for treatment planning. Subsequently, before each treatment fraction, a CBCT image is acquired and compared to the CBCT pre-treatment planning image, and the results of the comparison are used to modify the treatment plan for that treatment fraction to compensate for interfraction setup errors and/or interfraction organ motion. Due to limitations in permissible gantry rotation speeds (e.g., one rotation per minute) which cause the CBCT acquisition time to be slow compared to breathing (or other physiological cycles) of the patent, a gating scheme synchronized to patient breathing (or other physiological cycles) is used during CBCT acquisition to reduce the deleterious effects of organ motion in the reconstructed images. Also due to the relatively slow CBCT acquisition time, the CBCT volume data is generally useful only for patient set-up before each treatment fraction, and not for intra-fraction motion correction.

X-ray source arrays such as field emission "cold cathode" x-ray source arrays represent a promising advance in medical imaging and offer potential advantages over conventional x-ray tube sources in several respects. A conventional x-ray tube usually comprises a tungsten, tantalum or rhenium cathode that is heated to approximately 2000° C. to cause electrons to be emitted thermionically, the free electrons then being accelerated toward an anode by a high electrical potential such as 120 kV. X-ray radiation usable for imaging is created when the thermionically generated electrons strike an anode, usually made of tungsten, molybdenum, or copper, at a focal spot of the x-ray tube, the collision causing the emission of x-ray photons. While historically being the only practical and cost-effective way to provide imaging x-ray radiation in medical imaging environments, conventional x-ray tube sources can bring about many design compromises in view of their relatively large size and weight, high operating temperatures, high power consumption, relatively modest temporal resolution (e.g., on/off switching times), and their minimal amenability to miniaturization or formation into closely spaced arrays.

As an alternative to conventional x-ray tube technology in which free electrons are generated by thermionic emission, alternative technologies have been introduced in which the free electrons are generated by field emission. In a field emission source, free electrons are emitted upon the application of a voltage to a material having a high emission density, such as certain carbon nanotube (CNT) materials. Because field emission of electrons is produced by a high electric field, no heating is necessary. Field emission sources are thus often referred to as cold cathode sources. Advantageously, the electron beams emitted by such materials may have low divergence and thus provide ease of focusing onto a focal spot. Moreover, the virtually instantaneous response of the source offers time gating capabilities that may even be on the order of nanoseconds. Because they can be made exceedingly small, field emission x-ray sources are highly amenable to formation into arrays. According to U.S. Pat. No. 7,505,562B2, which is incorporated by reference herein, devices having 1000 pixels per meter (i.e., 1000 individual x-ray sources per meter) with pulse repetition rates on the order of 10 MHz can be envisioned using technology within the current state of the art.

As used herein, the term x-ray source array refers to a source of x-rays comprising a plurality of spatially distinct, electronically activatible x-ray emitters or emission spots (focal spots) that are addressable on at least one of an individual and groupwise basis. Although most x-ray source arrays suitable for use with one or more of the preferred embodiments will commonly be of the field emission "cold cathode" type, the scope of the present teachings is not so limited. By way of example, other types of x-ray source arrays that may be suitable for use with one or more of the preferred embodiments include scanning-beam array X-ray sources in which an electron beam digitally scans across a tungsten transmission target thirty times per second, sequentially producing ten thousand individually collimated X-ray beams, as reported by Triple Ring Technologies, Inc., of Newark, Calif.

X-ray source arrays have been proposed for use in kV imaging systems associated with radiation treatment systems, such as in US20090296886A1. However, it is believed that substantial advances in the configuration, operation, and/or manner of integration of x-ray source arrays into IGRT systems, such as those provided by one or more of the preferred embodiments herein, are needed in order to achieve clinical practicality, effectiveness, and market acceptance. It is to be appreciated the although particularly advantageous in the context of IGRT systems, one or more of the preferred embodiments is also applicable to a wide variety of other medical imaging applications outside the realm of image-guided radiation treatment.

More generally, one or more issues arises with respect to known medical imaging and/or radiation treatment systems that is at least partially addressed by one or more of the preferred embodiments described further hereinbelow. Other issues arise as would be apparent to a person skilled in the art in view of the present teachings.

BRIEF DESCRIPTION OF THE DRAWINGS

Reference will now be made to the accompanying drawings showing example embodiments of the present application, and in which:

FIG. 14 illustrates a smaller scale (i.e., less detailed) conceptual side view of an x-ray source array SA and collimator COLL according to a preferred embodiment, wherein the collimator COLL is segmented into a number of separately controlled segments COLSEG1, SOLSEG2, COLSEG3, and so on;

FIGS. 17-1 through FIG. 17-5 illustrate acquiring a set of x-ray tomosynthesis projection images of a target volume according to a preferred embodiment;

FIGS. 19-1 through FIG. 19-5 illustrate acquiring a set of x-ray tomosynthesis projection images of a target structure T according to a preferred embodiment;

FIGS. 21-1 through FIG. 21-5 illustrate acquiring a set of x-ray tomosynthesis projection images of a target volume according to a preferred embodiment that is functionally similar to that of FIG. 19-1 through FIG. 19-5, except that the selective localized illumination of digital detectors is achieved by mechanical control of the beamsteering angle of the x-ray collimating units XCU while the subset of x-ray sources within each x-ray source array unit SAU is kept constant;

DESCRIPTION

Figure 1:
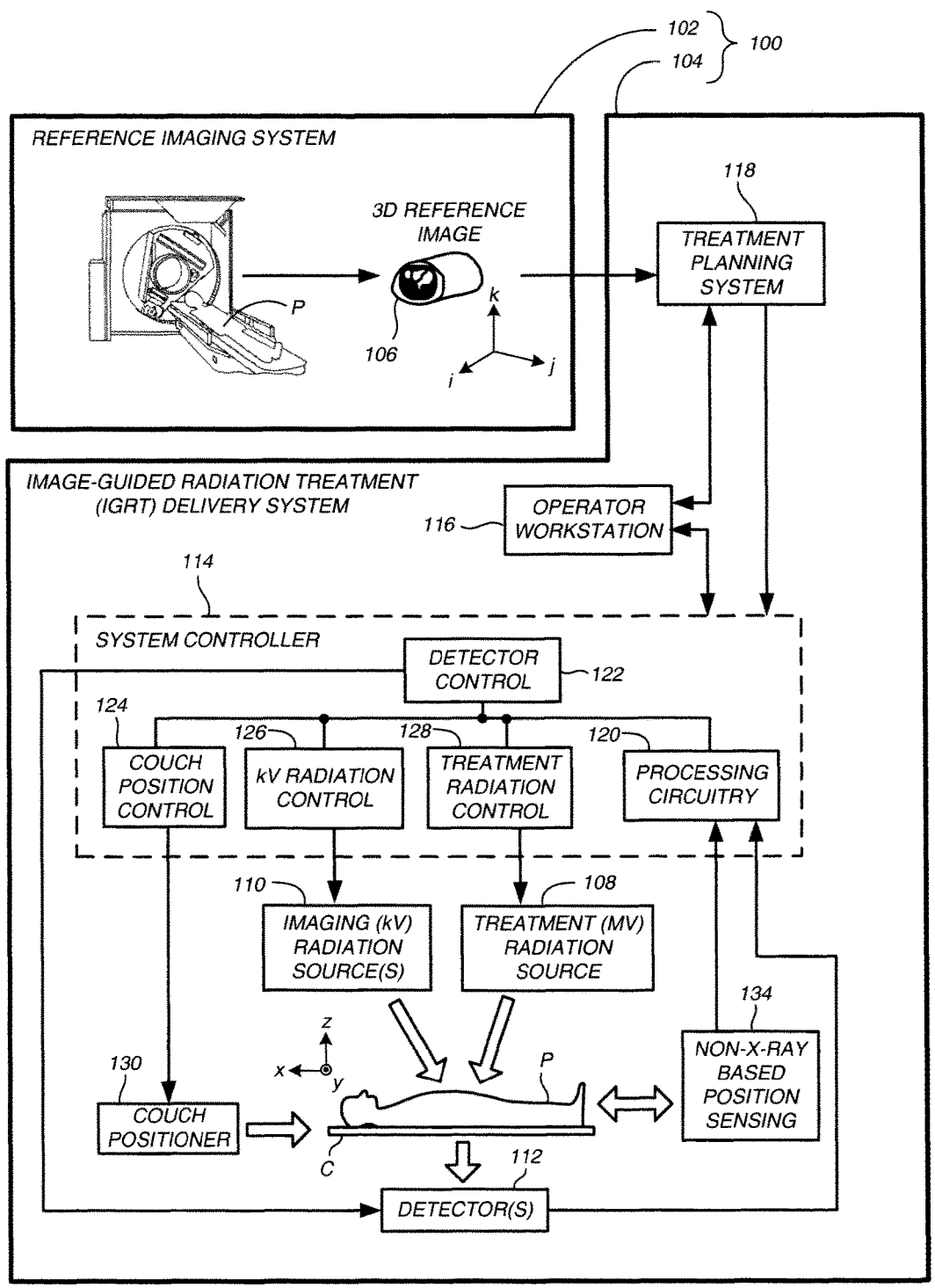
FIG. 1 illustrates a radiation treatment environment within which one or more of the preferred embodiments is advantageously applied.

FIG. 1 illustrates a radiation treatment environment 100 within which one or more of the preferred embodiments is advantageously applied. The radiation treatment environment 100 includes a reference imaging system 102 and an IGRT system 104. Reference imaging system 102 usually comprises a high precision volumetric imaging system such as a computed tomography (CT) system or a nuclear magnetic resonance imaging (MRI) system. In view of cost and workflow considerations in many clinical environments, the reference imaging system 102 is often a general purpose tool used for a variety of different purposes in the clinic or hospital environment, and is not specifically dedicated to the IGRT system 104. Rather, the reference imaging system 102 is often located in its own separate room or vault and is purchased, installed, and/or maintained on a separate and more generalized basis than the IGRT system 104. Accordingly, for the example of FIG. 1, the reference imaging system 102 is illustrated as being distinct from the IGRT system 104. Notably, for other radiation treatment environments that are not outside the scope of the present teachings, the reference imaging system 102 can be considered as an integral component of the IGRT system 104.

IGRT system 104 comprises a radiation treatment (MV) source 108 that selectively applies high-energy x-ray treatment radiation to a target volume of a patient P positioned on a treatment couch C. The MV source 108 applies the treatment radiation under the control of a system controller 114, and more particularly a treatment radiation control subsystem 128 thereof. System controller 114 further comprises processing circuitry 120, a detector controller 122, a couch position controller 124, and a kV radiation controller 126 each programmed and configured to achieve one or more of the functionalities described further herein. One or more imaging (kV) radiation sources 110 selectively emit relatively low-energy x-ray imaging radiation under the control of kV radiation controller 126, the imaging radiation being captured by one or more imaging detectors 112. In alternative preferred embodiments, one or more of the imaging detectors 112 can be a so-called portal imaging detector that captures high-energy x-ray treatment radiation from MV source 108 that has propagated through the target volume.

For one preferred embodiment, the kV imaging radiation sources 110 include both a two-dimensional stereotactic x-ray imaging system and a tomosynthesis imaging system. For other preferred embodiments, only a two-dimensional stereotactic x-ray imaging system is provided, while for still other preferred embodiments only a tomosynthesis imaging system is provided. Preferably, each of the stereotactic x-ray imaging system and the tomosynthesis imaging system are characterized by either (a) a fixed, predetermined, nonmoving geometry relative to the (x, y, z) coordinate system of the treatment room, or (b) a precisely measurable and/or precisely determinable geometry relative to the (x, y, z) coordinate system of the treatment room in the event they are dynamically moveable. The MV radiation source 108 should also, of course, have a precisely measurable and/or precisely determinable geometry relative to the (x, y, z) coordinate system of the treatment room.

A couch positioner 130 is actuated by the couch position controller 124 to position the couch C. A non-x-ray based position sensing system 134 senses position and/or movement of external marker(s) strategically affixed to the patient, and/or senses position and/or movement of the patient skin surface itself, using one or more methods that do not involve ionizing radiation, such as optically based or ultrasonically based methods. In one example, IGRT system 104 can be similar to a CYBERKNIFE® robotic radiosurgery system available from Accuray Incorporated of Sunnyvale, Calif., and the non-x-ray position sensing system 134 can be similar to relevant sensing components of the Accuray Incorporated SYNCHRONY® respiratory tracking system. IGRT system 104 further includes an operator workstation 116 and a treatment planning system 118.

In common clinical practice, treatment planning is performed on a pre-acquired treatment planning image 106 generated by the reference imaging system 102. The pre-acquired treatment planning image 106 is often a high resolution three-dimensional CT image acquired substantially in advance (e.g., one to two days in advance) of the one or more radiation treatment fractions that the patient will undergo. As indicated in FIG. 1 by the illustration of an (i, j, k) coordinate system for the treatment planning image 106, which is in contrast to the (x, y, z) treatment room coordinate system illustrated for the treatment room of the IGRT system 104, there is generally no pre-existing or intrinsic alignment or registration between the treatment planning image 106 coordinate system and the treatment room coordinate system. During the treatment planning process, a physician establishes a coordinate system (e.g., i, j, k in treatment planning image 106) within the treatment planning image, which may also be referred to herein as the planning image coordinate system or planning image reference frame. A radiation treatment plan is developed in the planning image coordinate system that dictates the various orientations, sizes, durations, etc., of the high-energy treatment radiation beams to be applied by the MV source 108 during each treatment fraction. Accurate delivery of therapeutic radiation to a target requires aligning the planning image coordinate system with the treatment room coordinate system as the entire delivery and tracking system (if present) is calibrated to the treatment room coordinate system. It will be appreciated that this alignment does not need to be exact and further appreciated that couch adjustment or beam delivery adjustment can be used to account for offsets in the alignment between the two coordinate systems.

Thus, immediately prior to each treatment fraction, under a precise image guidance of the kV imaging radiation sources 110 according to one or more of the embodiments described further hereinbelow, the patient is physically positioned such that the planning image coordinate system (defined, for example and not by way of limitation, by a physician while creating a treatment plan on a CT image or planning image) is positioned into an initial alignment with the treatment room coordinate system, hereinafter termed an initial treatment alignment or initial treatment position. This alignment is commonly referred to as patient set up.

Depending on the location of the target volume, the target volume can vary in position and orientation and/or can undergo volumetric deformations due to patient movement and/or physiological cycles such as respiration. As used herein, the term in-treatment alignment variation or in-treatment position variation is used to refer to the variations in position, orientation, and/or volumetric shape by which the current state of the target volume differs from the initial treatment alignment. By virtue of a known relationship between the treatment planning coordinate system and the treatment room coordinate system, the term in-treatment alignment variation can also be used to refer to the variations in position, orientation, or volumetric shape by which the current state of the target volume differs from that in the treatment planning coordinate system. More generally, the term initial treatment alignment or initial treatment position refers herein to the particular physical pose or disposition (including position, orientation and volumetric shape) of the body part of the patient upon patient setup at the outset of the treatment fraction. The term intrafraction alignment or intrafraction position refers herein to the particular physical pose or disposition (including position, orientation or volumetric shape) of the body part of the patient during the treatment fraction.

A non x-ray based position sensing system 134 may also be provided. This non x-ray based position sensing system 134 may include, by way of example and without limitation, external markers affixed in some manner to a patient's chest which move in response to respiration (other mechanisms for monitoring respiration may be used), and include a mono or stereoscopic x-ray imaging system, which as described above can precisely determine target location. System 134 correlates motion of the external markers with target motion, as determined from (for example) the mono or stereoscopic x-ray projections. Non x-ray based position sensing system 134, therefore, permits system controller 114 to monitor external marker motion, use the correlation model to precisely predict where the target will be located in real time (e.g., ~60 Hz), and direct the treatment beam to the target. As treatment of the moving target progresses additional x-ray images may be obtained and used to verify and update the correlation model.

According to a preferred embodiment, system controller 114 including processing circuitry 120 is configured and programmed to receive information from the non-x-ray based position sensing system 134 and the imaging detector(s) 112 or just from the imaging detector(s) 112 when treating a relatively stationary target volume (for example and without limitation a brain, spine or prostate tumor), compute an in-treatment alignment variation therefrom, and control the treatment radiation source 108 in a manner that compensates for the in-treatment alignment variation on a real-time basis. In the case where the target volume moves due to respiration, the more information-rich x-ray-based data from the imaging detectors 112 is updated at a relatively slow rate compared to the breathing cycle of the patient (for example, once every 15 seconds) to maintain reasonably low x-ray imaging dose levels, the less information-rich data from the non-x-ray based position sensing system 134 can be updated in substantially real-time (for example, 30 times per second). Using methods such as those described in the commonly assigned U.S. Pat. No. 6,501,981B1, a correlation model between one or more x-ray-sensed internal target volume (with or without fiducials) and one or more non-x-ray-sensed external markers is used to ascertain the in-treatment alignment variations on a real-time basis, the correlation model being updated (corrected) at each x-ray imaging interval. Advantageously, judicious x-ray/tomosynthesis imaging source collimation strategies according to one or more of the preferred embodiments described further infra can be advantageously used to improve determination of in-treatment alignment variations or target tracking by virtue of one or more of higher x-ray/tomosynthesis imaging quality, reduced x-ray radiation dose, and higher x-ray/tomosynthesis imaging data acquisition rates.

It is to be appreciated that the use of a non-x-ray based position sensing system 134 such as the SYNCHRONY® respiratory tracking system represents an option that, while advantageous in the radiation treatment of certain tumors within the lung or chest area, is not required for radiation treatments in many other body parts, such as the prostate, spine or brain. Whereas x-ray dosage concerns provide limits on the number of kV x-ray images that should be acquired in any particular intrafraction time interval (for example, no more than one kV image every 15 seconds, every 30 seconds, or every 60 seconds), tumors within the chest area can move at substantially faster periodic rates, therefore giving rise to the need for the non-x-ray based position sensing system 134. However, tumors in other parts of the body, such as the prostate, will generally experience motion on a much slower time scale, wherein the dose-limited kV x-ray imaging rate will be still be sufficiently high to effectively guide the radiation treatment. The prostate, for example, may experience movement due to an accumulation of urine in the nearby urinary bladder, an event for which one kV x-ray image every 60 seconds should be sufficient to track resultant movement. Accordingly, for the many other parts of the anatomy for which kV imaging rates are sufficient, the non-x-ray based position sensing system 134 and the associated "real time" tracking (i.e., tracking at a rate faster than the kV imaging rate) is not required.

It is to be appreciated that the exemplary radiation treatment environment of FIG. 1 is presented by way of example and not by way of limitation, that the preferred embodiments are applicable in a variety of other radiation treatment environment configurations, and that one or more of the preferred embodiments is applicable to general medical imaging environments outside the particular context of radiation treatment systems. Thus, for example, while one or more of the preferred embodiments is particularly advantageous when applied in the context of a radiation treatment environment in which the reference imaging system 102 is physically separated from, has no common coordinate system with, and/or has no other intrinsic means of volumetric image registration with the IGRT delivery system 104, the scope of the present teachings is not so limited. Rather, the one or more preferred embodiments can also be advantageously applied in the context of radiation treatment environments in which the reference imaging system is physically integral with radiation treatment delivery system or has other intrinsic linkages, such as a rail-based patient movement system, with the radiation treatment delivery system.

As used herein, "registration" of medical images refers to the determination of a mathematical relationship between corresponding anatomical or other (e.g. fiducials) features appearing in those medical images. Registration can include, but is not limited to, the determination of one or more spatial or alignment or intrafraction transformations that, when applied to one or both of the medical images, would cause an overlay of the corresponding anatomical features. The spatial or alignment or intrafraction transformations can include rigid-body transformations and/or deformable transformations and can, if the medical images are from different coordinate systems or reference frames, account for differences in those coordinate systems or reference frames. For cases in which the medical images are not acquired using the same imaging system and are not acquired at the same time, the registration process can include, but is not limited to, the determination of a first transformation that accounts for differences between the imaging modalities, imaging geometries, and/or frames of reference of the different imaging systems, together with the determination of a second transformation that accounts for underlying anatomical differences in the body part that may have taken place (e.g., positioning differences, overall movement, relative movement between different structures within the body part, overall deformations, localized deformations within the body part, and so forth) between acquisition times. The term alignment transformation refers herein to a transformation between a first coordinate system (for example and not by way of limitation a planning image coordinate system of a patient) and a second coordinate system (a treatment room coordinate system) whereby the alignment transformation determines the location of a target in the second coordinate system relative to the first coordinate system, for example and not by way of limitation at the time of patient setup prior to commencement of the treatment fraction. The term intrafraction transformation refers herein to a transformation between the first coordinate system and the second coordinate system whereby the intrafraction transformation determines the location of the target in the first coordinate system relative to the second coordinate system following commencement of the procedure, for example and not by way of limitation during the treatment fraction.

Figure 2:
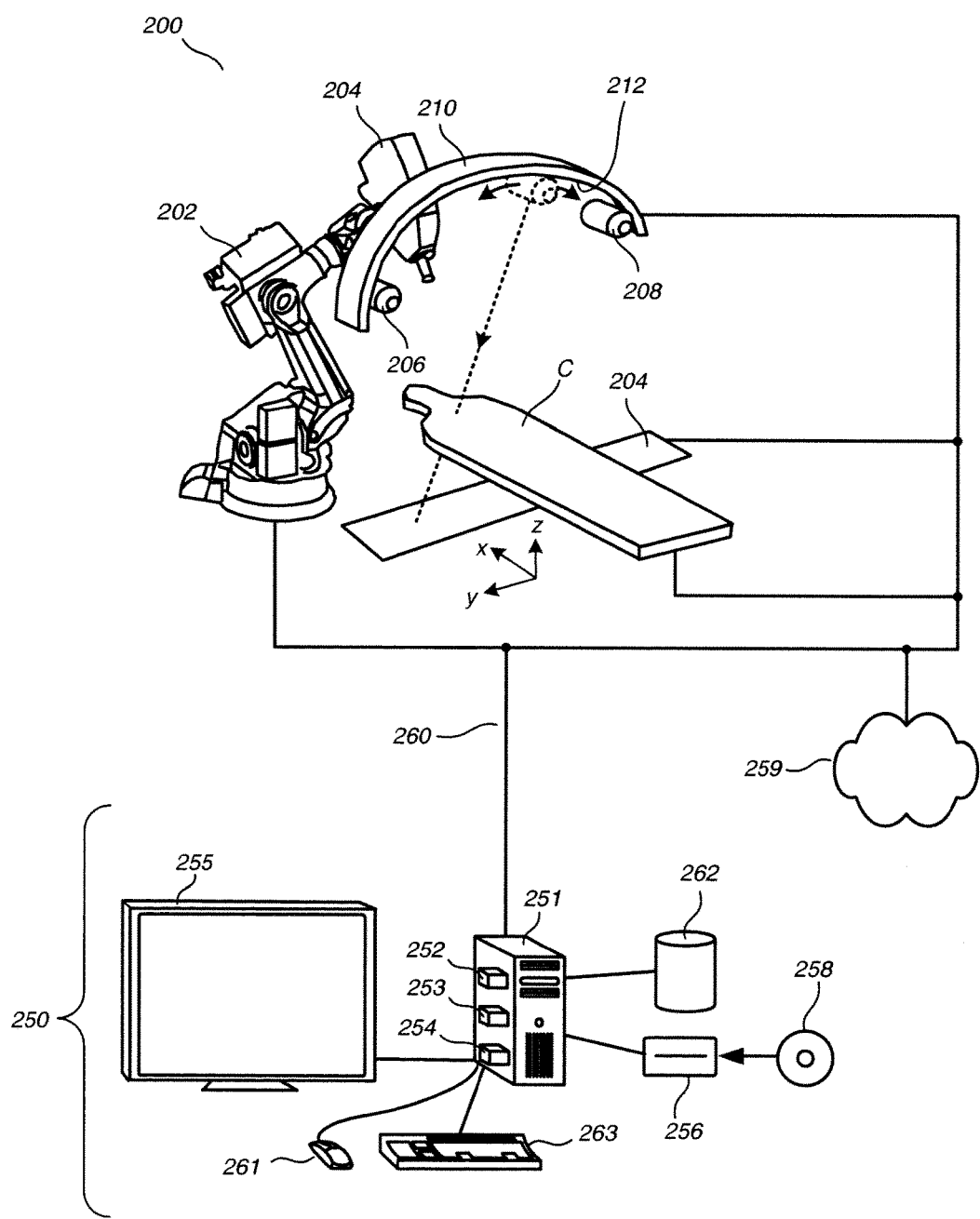
FIG. 2 illustrates an IGRT system having tomosynthesis imaging capability according to a preferred embodiment.

FIG. 2 illustrates an IGRT system 200 having tomosynthesis imaging capability according to a preferred embodiment. IGRT system 200 includes an MV radiation source 204 mounted on an articulated robot arm 202, and further includes a kV x-ray imaging system comprising dual conventional kV sources 206 and 208 translatably mounted on a ceiling-supported support rail 210 extending in an arc over and opposite a floor-mounted kV imaging detector 204. In a first mode of operation, the x-ray sources 206 and 208 can remain fixed at opposite ends of the rail 210 and, in conjunction with corresponding opposing ends of the kV imaging detector 204, can function as a stationary two-dimensional stereoscopic x-ray imaging system. In the first mode of operation, the patient alignment process (and, optionally, the in-treatment target tracking process) can proceed based on comparisons of stereoscopic x-ray images and digitally reconstructed radiographs (DRR's) derived from a reference volume as described, for example, in the commonly assigned U.S. Pat. Nos. 7,204,640B2, and 7,684, 647B2, US 20050049478A1, and US20080130825A1, a process that has been continuously improved over the years and has proven highly robust and effective. Similar methods have been used with substantial clinical and commercial success, such as in the CYBERKNIFE® system from Accuray Incorporated, which tracks, detects and corrects for tumor and patient movement during treatment and precisely delivers high doses of radiation to a tumor typically with sub-millimeter accuracy. In a second mode of operation, the kV source 206 and/or the kV source 208 can be dynamically translated in a tomosynthesis imaging arc along the rail 210 to achieve tomosynthesis imaging in conjunction with the full spatial extent of the imaging detector 204.

Included in FIG. 2 is a schematic diagram of a computer system 250 integrated with and/or coupled to the IGRT system 200 using one or more busses, networks, or other communications systems 260, including wired and/or wireless communications systems, and being capable in conjunction therewith of implementing the methods of one or more of the preferred embodiments. Methods of image guided radiation treatment in accordance with one or more of the preferred embodiments may be implemented in machine readable code (i.e., software or computer program product) and performed on computer systems such as, but not limited to, the computer system 250, wherein a central processing unit (CPU) 251 including a microprocessor 252, random access memory 253, and nonvolatile memory 254 (e.g. electromechanical hard drive, solid state drive) is operated in conjunction with various input/output devices, such as a display monitor 255, a mouse 261, a keyboard 263, and other I/O devices 256 capable of reading and writing data and instructions from machine readable media 258 such as tape, compact disk (CD), digital versatile disk (DVD), blu-ray disk (BD), and so forth. In addition, there may be connections via the one or more busses, networks, or other communications systems 260 to other computers and devices, such as may exist on a network of such devices, e.g., the Internet 259. Software to control the image guided radiation treatment steps described herein may be implemented as a program product and stored on a tangible storage device such as the machine readable medium 258, an external nonvolatile memory device 262, or other tangible storage medium. For clarity of presentation, the computer system 250 of FIG. 2 is omitted from further drawings and/or descriptions hereinbelow. Methods for configuring and programming the computer system 250 for achieving the functionalities described herein would be apparent to a person skilled in the art in view of the present disclosure.

Referring again to FIG. 2, according to one alternative preferred embodiment, the kV imaging sources 206 and 208 are fixably located at opposite ends of the rail 210, and are augmented by a plurality of detector-facing x-ray source arrays (not shown) distributed across a detector-facing surface 212 of the rail 210. A stereoscopic x-ray imaging mode of operation can be carried out by the kV imaging sources 206 and 208 kV in conjunction with opposing ends of the detector 204, while a tomosynthesis imaging mode of operation can be carried out by the x-ray source arrays (without physically moving the x-ray source arrays) in conjunction with the full spatial extent of the imaging detector 204. In another alternative preferred embodiment the kV imaging sources 206 and 208 are omitted altogether, wherein a stereoscopic x-ray imaging mode is achieved by operating only the particular x-ray array sources and detectors disposed near opposing ends of the rail 212, and wherein a tomosynthesis imaging mode of operation is carried out using the full spatial extent of the x-ray source arrays and imaging detector 204.

Figure 3:
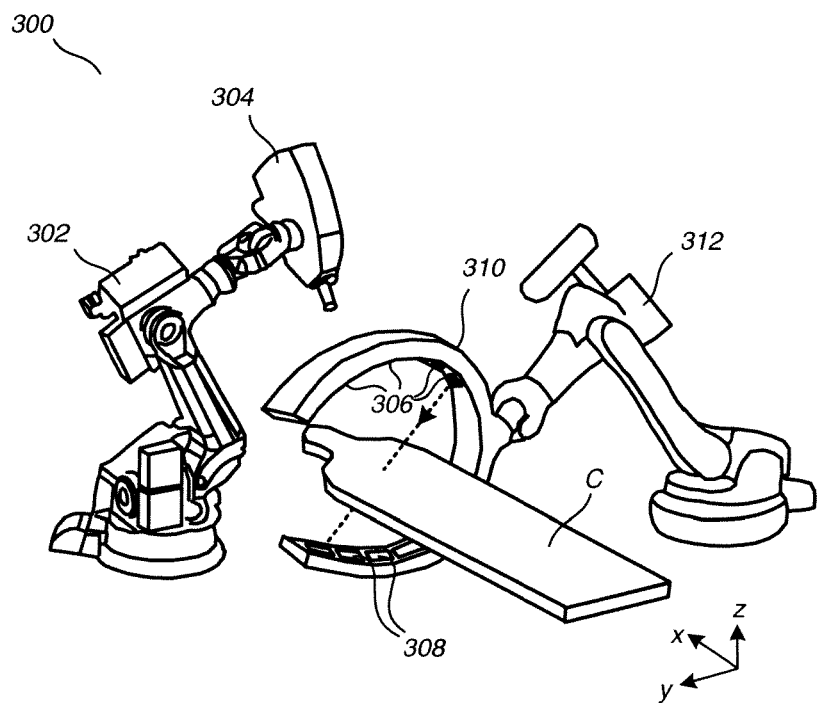
FIG. 3 illustrates an IGRT system having tomosynthesis imaging capability according to a preferred embodiment.

FIG. 3 illustrates an IGRT system 300 having tomosynthesis imaging capability according to a preferred embodiment. IGRT system 300 includes an MV radiation source 304 mounted on an articulated robot arm 302. The IGRT system 300 further includes a kV x-ray imaging system comprising a plurality of x-ray array sources 306 and a corresponding plurality of array detectors 308 arranged linearly along opposing surfaces of a C-arm 310. The C-arm 310 is, in turn, mounted on a robot arm 312 that permits a wide variety of different positions and orientations of the kV imaging system. By virtue of precise robotic control of the C-arm 310, the precise locations and orientations of the sources 306 and detectors 308 relative to the treatment room coordinate system is known. Upon placement of C-arm 310 into a desired imaging position, tomosynthesis imaging can proceed by selective activation of respective ones of sources 306 and detectors 308 over a tomosynthesis imaging arc.

Optionally, the kV imaging system can also be operated in a stereoscopic x-ray imaging mode by operating only the particular x-ray array sources and detectors at opposing ends of the linear arrangements.

Figure 4:
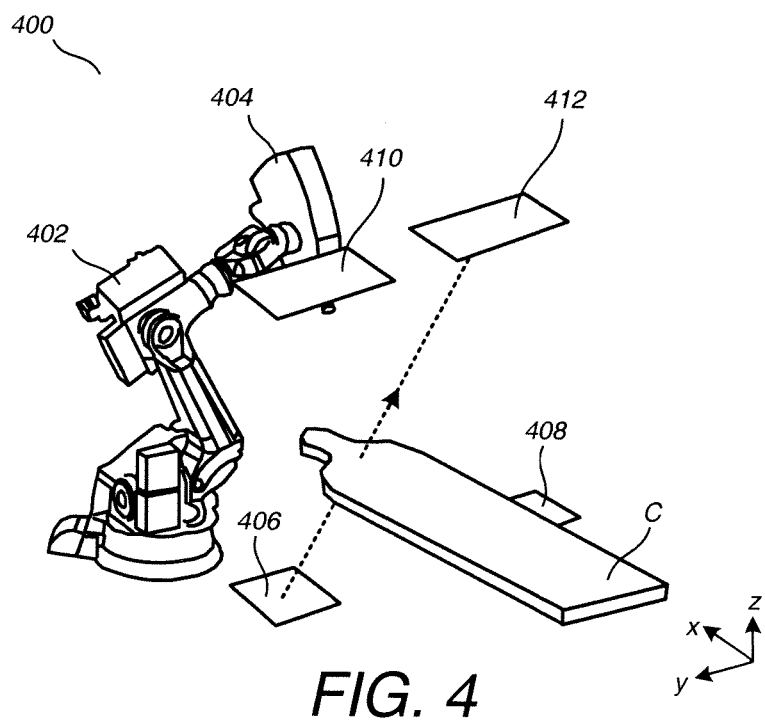
FIG. 4 illustrates an IGRT system having a stereoscopic tomosynthesis imaging capability according to a preferred embodiment.

FIG. 4 illustrates an IGRT system 400 having a stereoscopic tomosynthesis imaging capability according to a preferred embodiment. The IGRT system 400 includes an MV radiation source 404 mounted on an articulated robot arm 402. IGRT system 400 further comprises a first x-ray source array 406 paired with a first x-ray detector array 412 to establish a first "channel" of a stereoscopic x-ray tomosynthesis imaging system, and a second x-ray source array 408 paired with a second x-ray detector array 410 to establish a second "channel." For one preferred embodiment, each channel can be configured in an inverse geometry tomosynthesis imaging arrangement, as described further infra with respect to FIGS. 23A-23D and FIG. 24. The x-ray source arrays 406 and 408 can be mounted in or near the floor of the treatment vault, while the x-ray detector arrays 410 and 412 can be mounted in or near the ceiling of the treatment vault, although the scope of the preferred embodiments is not so limited.

Figure 5:
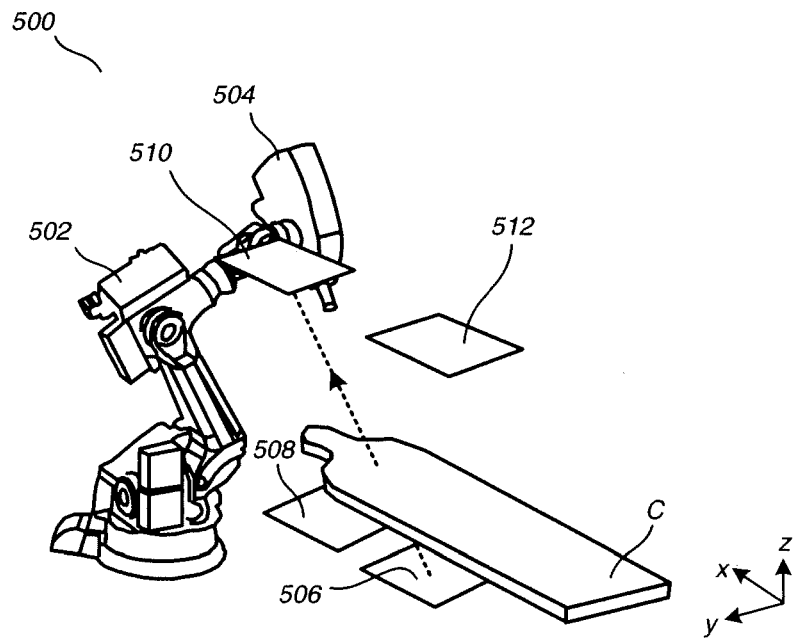
FIG. 5 illustrates an IGRT system having a stereoscopic tomosynthesis imaging capability according to a preferred embodiment.

FIG. 5 illustrates an IGRT system 500 having a stereoscopic tomosynthesis imaging capability according to a preferred embodiment. The IGRT system 500 is similar to the IGRT system 400 of FIG. 4, and includes numbered components 502-512 similar to the numbered components 402-412 of FIG. 4, respectively, except that the kV source and detector arrays are positioned to form a stereoscopic arc extending along the head-to-toe direction of the treatment couch rather than the left-to-right direction as in FIG. 4. In an alternative preferred embodiment (not shown), the kV imaging features of FIGS. 4 and 5 can be combined, such that there are four (4) x-ray source arrays in or near the floor and four (4) x-ray detector arrays in or near the ceiling, such that stereoscopic imaging arcs along either (or both) of the head-to-toe and left-to-right directions can be provided. In still another alternative preferred embodiment (not shown), the x-ray source arrays 506 and 508 can be positioned on an in-floor mechanical platter that is capable of in-floor rotation around a vertical axis passing through the isocenter (not shown), and the x-ray detector arrays 510 and 512 can be positioned on an in-ceiling mechanical platter capable of in-ceiling rotation around that same vertical axis, wherein the mechanical platters can be rotated to provide an option between the left-to-right stereoscopic arc configuration of FIG. 4 and the head-to-toe stereoscopic arc configuration of FIG. 5. In yet another alternative preferred embodiment (not shown), the x-ray source arrays 506 and 508 can be replaced by a single long x-ray source array that extends across the area collectively covered by both of them in FIG. 5 and further includes all of the area lying between them, and the x-ray detector arrays 510 and 512 can likewise be replaced by a single long x-ray detector array that extends across the area collectively covered by both of them in FIG. 5 and further includes all of the area lying between them.

Figure 6:
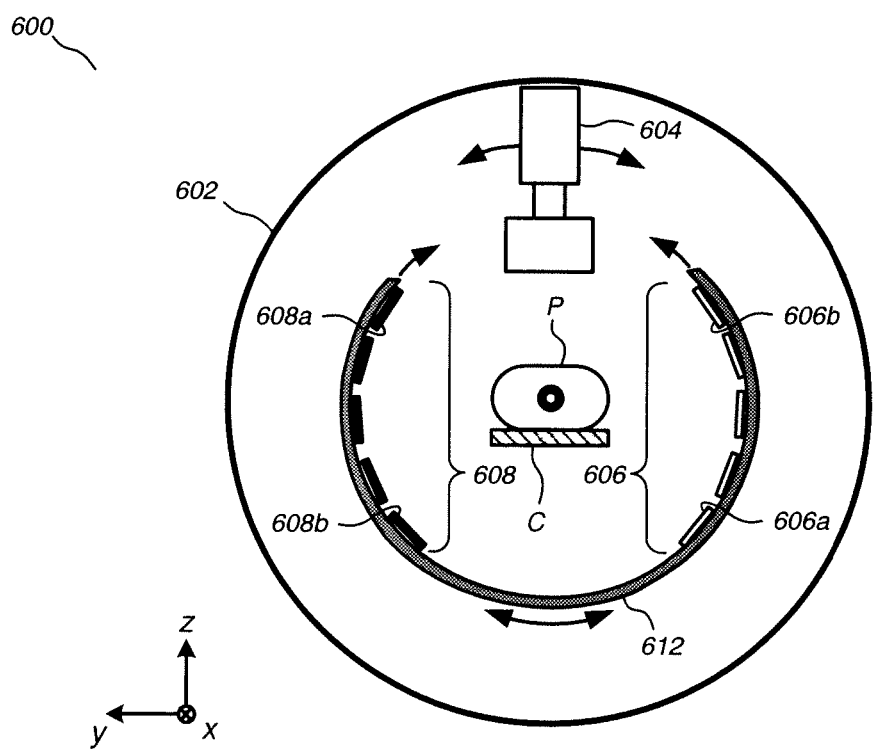
FIG. 6 illustrates a simplified cross-sectional view of an IGRT system having a tomosynthesis imaging capability according to a preferred embodiment, the IGRT system being implemented in the form of a rotating gantry structure.

FIG. 6 illustrates a simplified cross-sectional view of an IGRT system 600 having a tomosynthesis imaging capability according to a preferred embodiment, the IGRT system 600 being implemented in the form of a rotating gantry structure. The IGRT system 600 includes an MV source 604 mounted on a gantry frame 602 in a manner that permits 360 degree rotation around the patient, and further includes a kV imaging system comprising a plurality of x-ray array sources 606 and a corresponding plurality of array detectors 608 arranged along opposing surfaces of a support ring 612 that is rotatable around the patient independently of the MV source 604. Upon rotation of the support ring 612 into a desired imaging position, tomosynthesis imaging can proceed by selective activation of respective ones of sources 606 and detectors 608 over a tomosynthesis imaging arc. Optionally, the kV imaging system can also be operated in a stereoscopic x-ray imaging mode by operating only the particular x-ray array sources and detectors at opposing ends of the linear arrangements along the support ring 612.

It is to be appreciated that one or more of the preferred embodiments described further infra can be implemented in conjunction with a wide variety of different radiation treatment delivery mechanisms, including robotic arm-based systems, C-arm gantry based systems, ring gantry-based systems, and barrel gantry-based systems, and that the particular examples of FIGS. 2-4 are presented only by way of example and not by way of limitation. Other non-limiting examples of IGRT system configurations suitable for use with one or more of the preferred embodiments include systems discussed in U.S. Pat. Nos. 7,188,999B2, 7,227, 925B1, and the commonly assigned U.S. Provisional Application Ser. No. 61/307,847, each of which is incorporated by reference herein.

Figure 7:
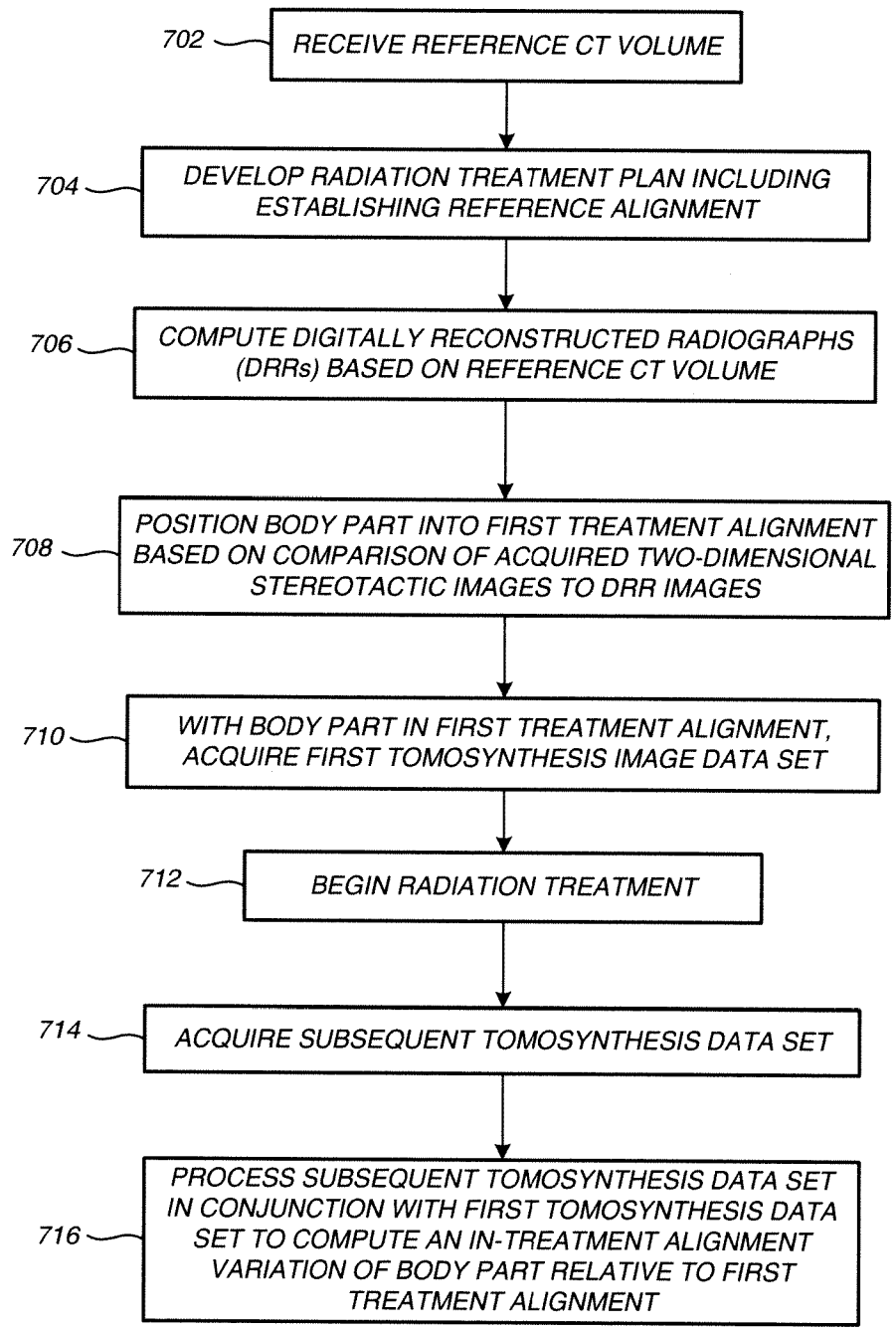
FIG. 7 illustrates image guided radiation treatment (IGRT) of a body part by an IGRT apparatus according to a preferred embodiment.

FIG. 7 illustrates image guided radiation treatment (IGRT) of a body part by an IGRT apparatus according to a preferred embodiment. The IGRT apparatus includes a two-dimensional stereotactic x-ray imaging system and a tomosynthesis imaging system each having known geometries relative to the treatment coordinate system of the IGRT apparatus. At step 702, a reference CT volume of the body part is received. At step 704, a radiation treatment plan for an application of treatment radiation to the body part by the IGRT apparatus is developed. During the treatment planning process, a planning image coordinate system is established. At step 706, a population of two-dimensional stereotactic digitally reconstructed radiograph (DRR) images is generated, based on the known imaging geometry of the treatment room two-dimensional mono or stereotactic imaging system.

At step 708, which is preferably carried out immediately prior to the beginning of radiation treatment, the body part is positioned into a first treatment alignment with the treatment coordinate system by acquiring two-dimensional stereotactic x-ray images, and comparing the acquired stereotactic x-ray images to the DRR images. For one preferred embodiment, this patient alignment process proceeds according to one or more methods described in the commonly assigned U.S. Pat. Nos. 7,204,640B2, 7,684,647B2, US 20050049478A1, and US20080130825A1. Even though based on feedback provided by two-dimensional stereotactic imaging, which provides lesser information than three-dimensional imaging modalities, such methods have been continuously improved and perfected over the years (for example, in relation to the CYBERKNIFE® robotic radiosurgery system available from Accuray Incorporated) and have proven precise, robust, and reliable.

At step 710, with the body part still in the first treatment alignment, a first tomosynthesis data set of the body part is acquired. By virtue of the known imaging geometries of the two-dimensional stereotactic x-ray imaging system and the tomosynthesis imaging system relative to the treatment room, and by virtue of the precise and reliable nature of the positioning process of step 708, there is provided an intrinsic, highly precise registration between first tomosynthesis data set and the planning image data set. The precision of this intrinsic registration is even further facilitated in an optional preferred embodiment in which a same x-ray image source is shared between the tomosynthesis imaging system and the two-dimensional stereotactic x-ray imaging system.

Alternatively, the intrinsic registration can be obtained by acquiring the set up images (mono or stereo 2D images or CBCT image) substantially simultaneously. By "substantially simultaneous" it is meant that the images are acquired within a time frame during which the target volume does not appreciably move such that inherent or intrinsic registration between the two images can be assumed. Inherent or intrinsic registration means that the two images are sufficiently aligned to carry out target tracking and radiation delivery to within the tolerance of the treatment plan being delivered. For a standard fractionated radiotherapy case, the tolerances will not be as high whereas for hypofractionated radiosurgery sub millimeter tolerances may be necessary. It will be appreciated that when using a CBCT image as a set up image, data necessary for the first tomosynthesis can be obtained from the data used to generate the CBCT image. In this latter case, the set up image and the first tomosynthesis image are generated from the very same data.

Subsequent to the patient alignment process and the acquisition of the first tomosynthesis data set, and usually after the beginning of radiation treatment (step 712), a subsequent tomosynthesis data set of the body part is acquired at step 714 using the tomosynthesis imaging system. At step 716, the subsequent tomosynthesis image data set is processed in conjunction with the first tomosynthesis data set to compute an in-treatment alignment variation of the body part relative to at least one of the first treatment alignment and/or the planning coordinate system, that is to say the subsequent tomosynthesis image is used to track intrafraction target motion. Without limitation, the in-treatment alignment variation can be measured and characterized by a rigid body transformation and/or a non-rigid transformation for accommodating elastic deformations in the body part during the treatment delivery. The transformation is used to adjust the patient relative to the treatment beam or vice versa in order to deliver the radiation according to plan. Further tomosynthesis imaging data sets are acquired on an ongoing basis (for example, every 15 seconds) and compared to one or more previous tomosynthesis imaging data sets and/or the first tomosynthesis imaging data set to achieve effective tracking of in-treatment alignment variations throughout the radiation treatment fraction.

Advantageously, the method of FIG. 7 harnesses the three-dimensional and speedy character of tomosynthesis imaging for the important purpose of tracking deformable movement of the body part during the treatment fraction, while at the same time harnessing tried and true patient positioning methods based on x-ray stereoscopic and DRR image comparisons. The method is believed to provide one or more advantages over methods such as those of U.S. Pat. Nos. 7,532,705B2 and 7,711,087B2. For example, although it is indeed possible to compute alignments between (i) tomosynthesis data from simulated x-ray projections through the reference CT volume, and (ii) tomosynthesis data from live projections through the patient, as set forth in U.S. Pat. No. 7,532,705B2, this can be a highly computationally intensive process, and can be subject to errors from inevitable differences between the virtual tomosynthesis imaging geometry of the simulated x-ray projections and real-world tomosynthesis imaging geometry of the IGRT system. Likewise, although it is indeed possible to compute alignments between (i) slices from reference CT volume, and (ii) tomosynthesis data from live projections through the patient, as set forth in U.S. Pat. No. 7,711,087B2, this would also be highly computationally intensive and highly subject to cross-modality, cross-acquisition-system errors. Advantageously, the method of FIG. 7 does not depend on a need to simulate the tomosynthesis imaging geometry of the IGRT system, and does not depend on the need to directly compare data volumes from two distinct imaging systems. Instead, the in-treatment tracking method of FIG. 7 is directed to a more realistic, apples-to-apples alignment computation between two (or more) tomosynthesis data sets acquired using the same tomosynthesis acquisition system, while the patient positioning process, which does indeed depend on comparing image data from two different systems, harnesses tried and true methods based on x-ray stereoscopic and DRR image comparisons.

Notably, although certain additional preferred embodiments described hereinbelow do involve comparison between (i) the reference CT volume or other reference imaging modality (or image data abstracted therefrom such as digitally reconstructed tomographs (DRTs)) and (ii) tomosynthesis image data from an on-board tomosynthesis imaging system, and therefore the need to perform registrations of image data from different frames of reference and/or different imaging modalities is indeed implicated, these difficult registrations only need to be performed at patient setup and not during intrafraction radiation delivery. Because these difficult computations can be computed prior to the instantiation of radiation delivery, rather than during the intrafraction radiation delivery, their computational complexity becomes less of a problem, and time can be taken to compute an optimal result.

Figure 8A:
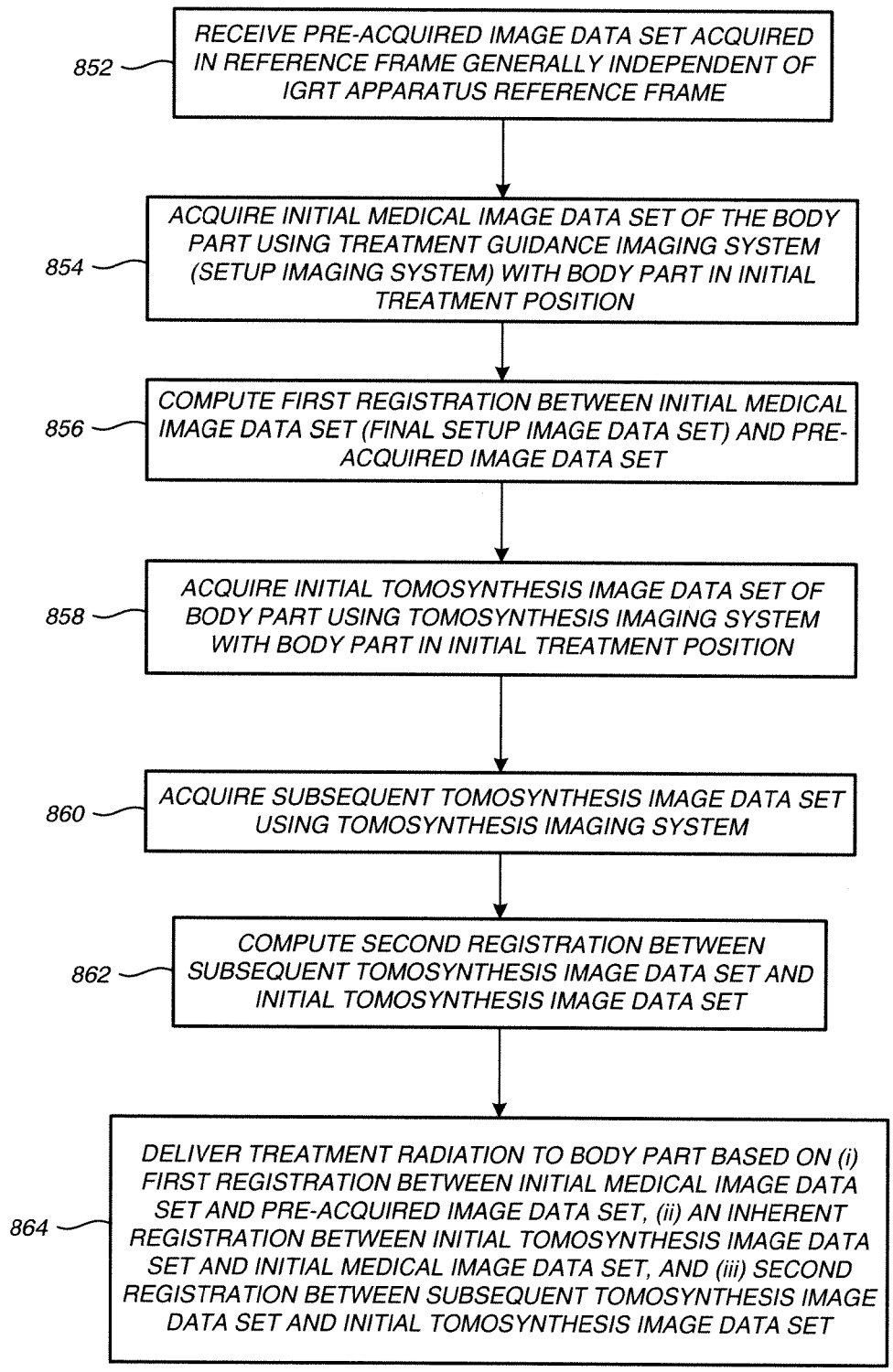
FIG. 8A illustrates image guided radiation treatment of a body part by an IGRT apparatus according to another preferred embodiment.

FIG. 8A illustrates image guided radiation treatment of a body part by an IGRT apparatus according to another preferred embodiment. For this preferred embodiment, the IGRT apparatus includes a treatment guidance imaging system having a known geometry relative to the reference frame of the IGRT apparatus, which can alternatively be termed an on-board imaging system. The treatment guidance imaging system comprises a combination of a tomosynthesis imaging system and an additional medical imaging system, the tomosynthesis imaging system being primarily directed to facilitating intrafraction imaging of the target volume for target tracking, the additional medical imaging system being directed primarily to facilitating a patient setup process in which the patient is positioned into an initial treatment position relative to the IGRT apparatus prior to instantiation of radiation delivery. The additional medical imaging system can be termed a setup imaging system, although it is to be appreciated that the scope of its functionality can extend beyond patient setup without departing from the scope of the preferred embodiments.

According to one preferred embodiment, the setup imaging system and the tomosynthesis imaging system that form the treatment guidance imaging system are either integrated into a common set of imaging hardware or have precisely known geometries relative to each other and the frame of reference of the IGRT apparatus. It is not required that these precisely known geometries be static or permanently fixed, but only that their geometrical relationships be precisely known at any relevant point in time. Although there are many different modalities and configurations that can serve as the setup imaging system, in one preferred embodiment the setup imaging system can be a CBCT imaging system, such as may be provided by one or more of the IGRT systems disclosed in the commonly assigned Ser. No. 61/307,847, supra, the commonly assigned Atty. Dkt. No. AR-002A-PROV, supra, and/or the IGRT apparatus 600 of FIG. 6, supra. Thus, for example, in the IGRT apparatus 600 of FIG. 6, in addition to the on-board tomosynthesis imaging system provided by virtue of the array sources 606 and the array detectors 608, there can also be provided an on-board CBCT system usable for patient setup by virtue of an additional mode of operation in which the support ring 612 is rotated by a full 360 degrees (or at least 180 degrees plus the fan beam angle) around the patient while one or more of the array sources 606 and array detectors 608 is operated at regular angular intervals. Importantly, such CBCT system has an intrinsic, inherent, precisely known spatial registration with the tomosynthesis imaging system because its imaging hardware is integral therewith. For another preferred embodiment, the onboard setup imaging system can alternatively comprise a 2D stereo x-ray imaging system using that same hardware. For other preferred embodiments, the onboard setup imaging system can be an ultrasound system or a system of some other imaging modality, provided only that it can be physically implemented in conjunction with the tomosynthesis imaging system and that its physical positioning and imaging geometry is known or can be precisely measured relative to the frame of reference of the tomosynthesis imaging system, the overall IGRT apparatus, and the treatment vault.

Referring again to FIG. 8A, at step 852 a pre-acquired image data set of the body part is received, the pre-acquired image data set having been acquired in a reference frame generally independent of the reference frame of the IGRT apparatus. In one preferred embodiment, the pre-acquired image data set may have been acquired using the reference CT imaging system 102 of FIG. 1, supra, or alternatively it may be the planning image where the physician has defined the planning coordinate system while creating the treatment plan. However, the scope of the present teachings is not so limited, and in other prefer embodiments the pre-acquired image data set may have been acquired using CBCT, MRI, ultrasound, or tomosynthesis imaging equipment located in a different room than the treatment vault or otherwise having a different frame of reference than that of the IGRT apparatus.

Figure 8B:
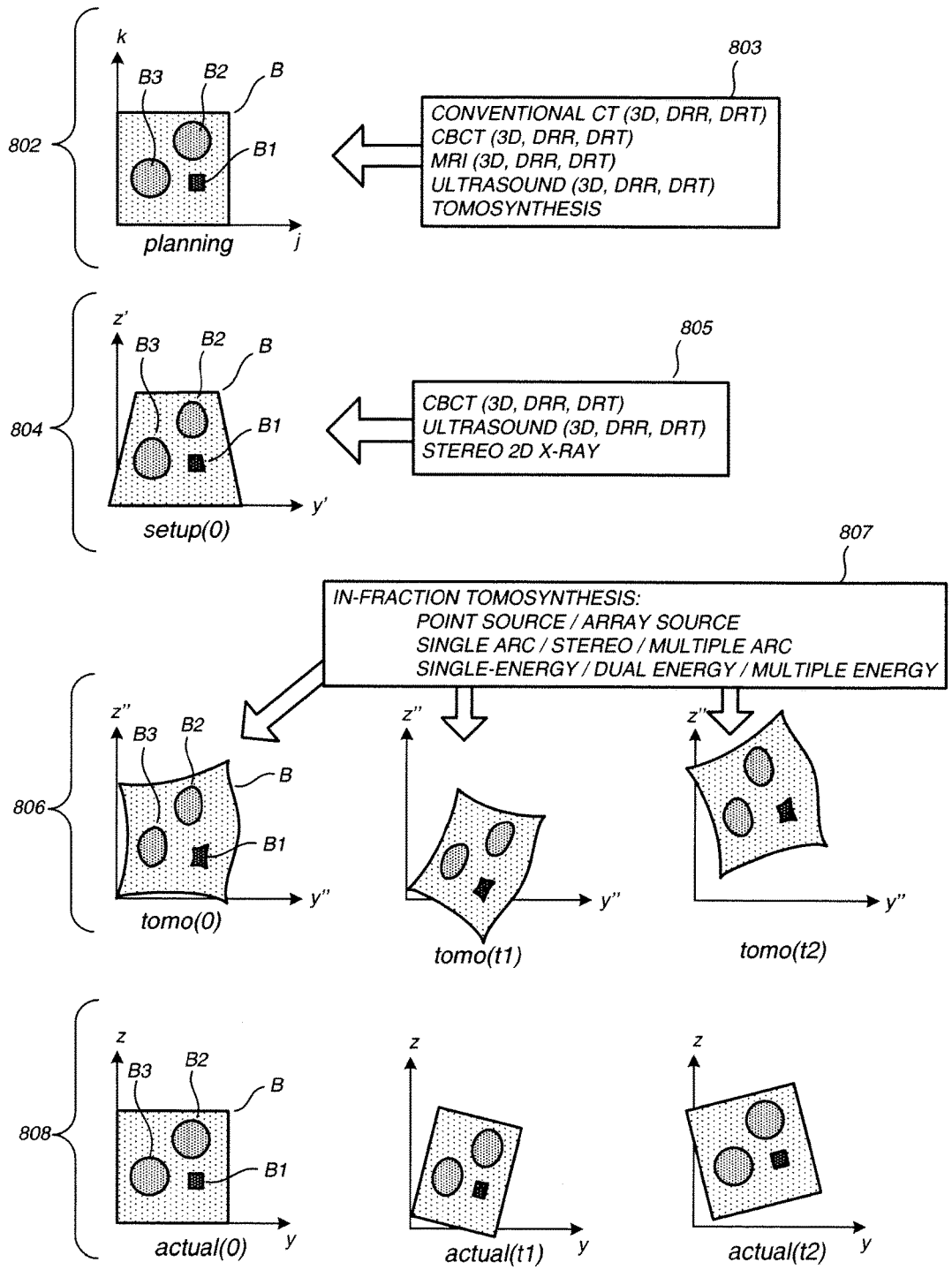
FIG. 8B illustrates a layout of simplified conceptual versions of the various images involved in the method of FIG. 8A.

FIG. 8B illustrates a layout of simplified conceptual versions of the various images involved in the method of FIG. 8A. Shown in simplified conceptual form is a pre-acquired image data set 802 of a body part B, the body part B including a target structure B1 (for example, a tumor) that is the subject of the desired application of the treatment radiation beam, as well as certain sensitive non-target structures B2 and B3 that should be avoided by the treatment beam. Adjacent thereto in FIG. 8B is a block 803 illustrating the various modalities that can be used to acquire the pre-acquired image data set 802. Importantly, it is to be appreciated that the pre-acquired image data set 802, as that term is used herein, can refer not only to the particular 3D image volume that was acquired, but can alternatively refer to any expression or abstraction of that same information, such as DRRs or DRTs (digitally reconstructed tomograph) generated from that 3D volume. The pre-acquired image data set 802 will have characteristics and artifacts unique to the particular imaging modality and imaging geometry of the reference imaging system 102.

Referring again to FIG. 8A, at step 854 an initial medical image data set of the body part is acquired using the setup imaging system while the body part is in an initial treatment position relative to the IGRT apparatus. As discussed above, the body part is in the initial treatment position when the patient setup process is complete and just before the beginning of the application of treatment radiation. For clarity of disclosure herein, the time "0" is used to refer to the time at which the body part is in the initial treatment position. Shown in simplified conceptual form in FIG. 8B is an initial medical image labeled "setup(0)" with numerical reference 804 that is representative of the medical image acquired by the setup imaging system at time 0. Without loss of generality, the initial medical image labeled "setup(0)" with numerical reference 804 is referenced herein as the setup image data set 804.

Also illustrated at the bottom of FIG. 8B for purposes of descriptive comparison is a graphical representation labeled "actual(0)" and having numerical reference 808, which represents a true version of the actual, physical body part as it is actually positioned in the treatment room. Without loss of generality, the graphical representation labeled "actual(0)" and having numerical reference 808 is referenced herein as the actual disposition 808 of the body part at time 0. Notably, the actual disposition 808 at time 0 is illustrated in the actual x-y-z coordinate system of the treatment room (only the y-z coordinates are shown in the simplified 2D version of FIG. 8B), the pre-acquired image data set 802 is illustrated in the i-j-k coordinate system of the reference imaging system 102, and the setup image data set 804 is illustrated in a coordinate system x'-y'-z' of the setup imaging system (which system has a precisely known geometrical relationship, such as by calibration, to the x-y-z coordinate system of the treatment room). As illustrated conceptually in FIG. 8B, the setup image data set 804 will have characteristics and artifacts unique to the particular imaging modality and imaging geometry of the setup imaging system, which will generally be different than the characteristics and artifacts of the pre-acquired image data set 802. Adjacent to the setup image data set 804 in FIG. 8B is a block 805 illustrating the various modalities (e.g., CBCT, ultrasound, stereo 2D x-ray) that can be used to acquire the setup image data set 804, as well as the various abstractions (e.g., DRRs or DRTs) with which the setup image data set 804 can be represented.

Referring again to FIG. 8A, at step 856 a first registration between the initial medical image data set (i.e., the setup image data set 804) and the pre-acquired image data set 802 is performed. For one preferred embodiment, the registration process is separable into (i) computation of a coordinate transformation associated with imaging geometry and/or reference frame differences between the two imaging systems, and (ii) computation of a first alignment variation or position variation associated with underlying anatomical and/or positional variations of the body part between the times of acquisition.

Figure 8C:
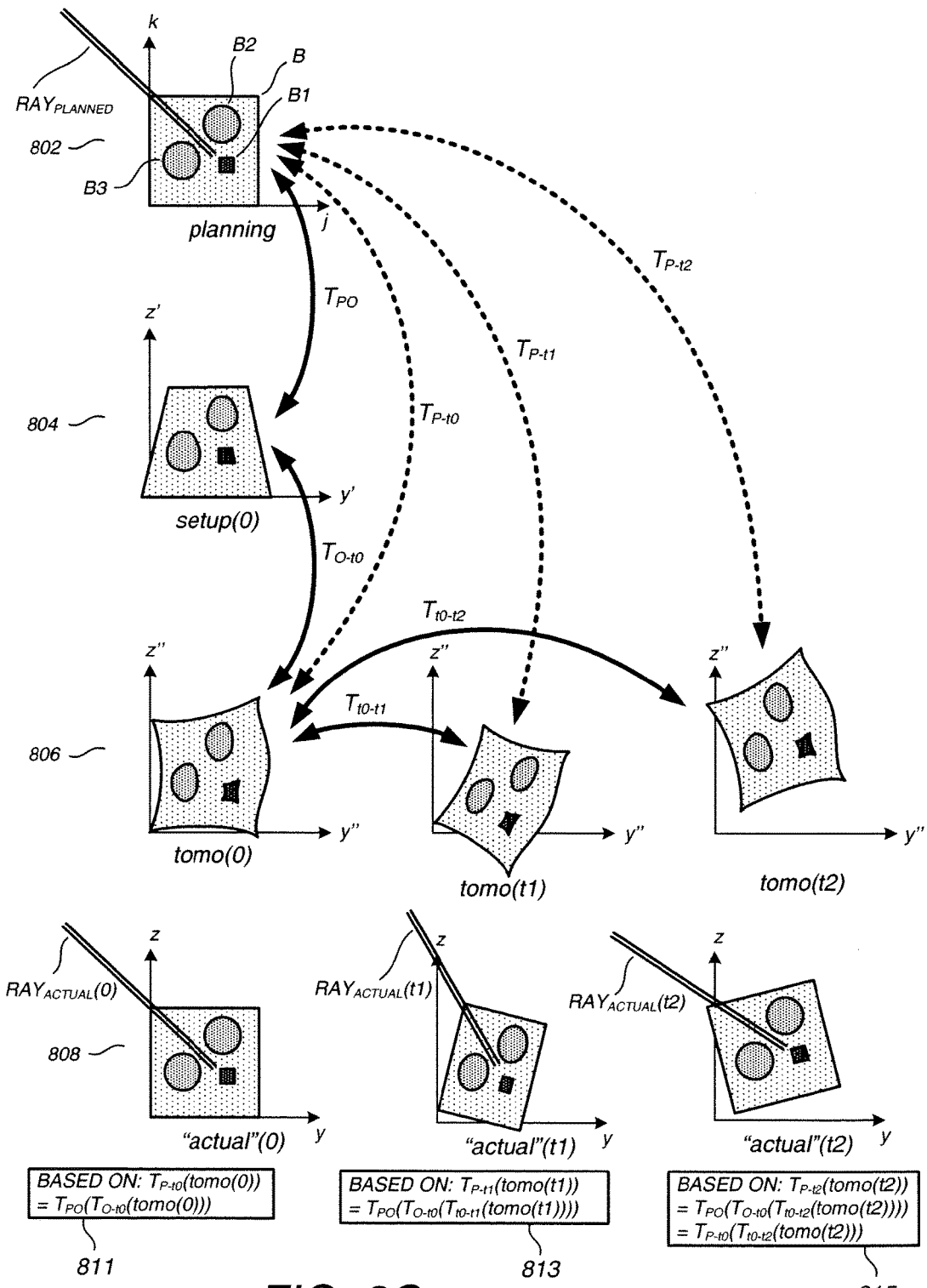
FIG. 8C illustrates the simplified conceptual image versions of FIG. 8B together with simplified graphical representations of transformations "T" associated with selected registrations therebetween to be performed according to one or more of the preferred embodiments.

FIG. 8C illustrates the simplified conceptual image versions of FIG. 8B together with simplified graphical representations of transformations "T" associated with selected registrations therebetween to be performed according to one or more of the preferred embodiments. Thus, illustrated in FIG. 8C is a transformation $T_{PO}$ associated with a registration between the pre-acquired image data set 802 and the setup image data set 804.

At step 858, an initial tomosynthesis image data set of the body part is acquired using the tomosynthesis imaging system. Shown in simplified conceptual form in FIG. 8B is an image labeled "tomo(0)" with numerical reference 806 that is representative of a reconstructed version of the tomosynthesis image data acquired by the tomosynthesis imaging system at time 0l, and which without loss of generality is referenced herein as the initial tomosynthesis image data set tomo(0). The initial tomosynthesis data set tomo(0) is illustrated in FIG. 8B in a coordinate system x"-y"-z" of the tomosynthesis imaging system (which coordinate system is calibrated to the treatment room coordinate system x-y-z). As illustrated conceptually in FIG. 8B, the initial tomosynthesis image data set tomo(0) will have characteristics and artifacts unique to the tomosynthesis imaging modality and the particular imaging geometry of the tomosynthesis imaging system, which will generally be different than the characteristics and artifacts of the pre-acquired image data set 802 and, in the general case, will also be different than the characteristics and artifacts of the setup image data set 804. Advantageously, there is an intrinsic, inherent registration provided between the setup image data set 804 and the initial tomosynthesis image data set tomo(0) by virtue of the precisely known geometries of their acquisition systems relative to each other and by virtue of the set up and tomo(0) images being acquired close in time preferably such the position of the target and other objects of interest have not appreciably moved between image acquisition; this inherent registration making a transformation $T_{O\text{-}r0}$ therebetween relatively straightforward to implement even when the data sets are from different modalities.

Referring again to FIG. 8A, at step 860 a subsequent tomosynthesis image data set, i.e., an intrafraction tomosynthesis data set, is acquired using the tomosynthesis imaging system. Shown in FIG. 8B are examples of a subsequent tomosynthesis data set tomo(t1) which reflects, albeit in its heavily artifact-laden tomosynthesis manner, deformations and positional variations in the body part that occurred between time 0 and time t1. These deformations and positional variations are shown conceptually therebelow in FIG. 8B by the actual disposition 808 at time t1. At step 862, a second registration between the subsequent tomosynthesis image data set tomo(t1) and the initial tomosynthesis image data set tomo(0) is performed. Shown in FIG. 8C is a transformation $T_{r0\text{-}t1}$ associated with this second registration. Advantageously, because the subsequent tomosynthesis image data set tomo(t1) will have most if not all the same characteristics and artifacts as the initial tomosynthesis image data set tomo(0), this registration process is extremely fast and straightforward, very quickly yielding the underlying anatomical and/or positional variations of the body part between times 0 and t1 with respect to the x"-y"-z" frame of reference of the tomosynthesis imaging system.

Finally, at step 864 treatment radiation is delivered to the body part based at least in part on information derived from (i) the first registration between the initial medical image data set (setup image data set 804) and the pre-acquired image data set 802 (see FIG. 8C, transformation $T_{PO}$), (ii) the inherent registration between the initial tomosynthesis image data set tomo(0) and the initial medical image data set (setup image data set 803) (see FIG. 8C, transformation $T_{O\text{-}r0}$), and (iii) the second registration between the subsequent tomosynthesis image data set tomo(t1) and the initial tomosynthesis image data set tomo(t0) (see FIG. 8C, transformation $T_{r0\text{-}t1}$). The process can then be repeated for a subsequent tomosynthesis image data set tomo(t2) and each subsequent tomosynthesis image data set acquired thereafter during the treatment fraction. For one preferred embodiment, using the intrafraction time t1 as an example, the delivery of the treatment radiation comprises computing a third registration between tomo(t1) and the pre-acquired image data set 802 (see FIG. 8C, transformation $T_{P\text{-}t1}$) based on a serial application of the second registration (see FIG. 8C, transformation $T_{r0\text{-}t1}$), the inherent registration between the initial tomosynthesis image data set tomo(0) and the setup image data set 804 (see FIG. 8C, transformation $T_{O\text{-}r0}$), and the first registration (see FIG. 8C, transformation $T_{PO}$), as reflected in box 813 of FIG. 8C.

Also shown in FIG. 8C for purposes of illustration is an exemplary treatment beam $RAY_{PLANNED}$ that was computed by the treatment planning system prior to the treatment fraction based on the pre-acquired image data set 802. For purposes of this very simple example, it is presumed that the treatment plan consists of a single, stationary radiation beam $RAY_{PLANNED}$ that persists throughout the treatment fraction and which impinges upon the treatment target B1 without passing through sensitive non-target structures B2 and B3. As illustrated near the bottom of FIG. 8C, at time 0 the fraction begins with the actual treatment beam $RAY_{ACTUAL}$ (0) which is determined for the actual IGRT coordinate space based on the first registration between the initial medical image data set (setup image data set 804) and the pre-acquired image data set 802 (see FIG. 8C, transformation $T_{PO}$), as reflected in box 811 of FIG. 8C. As of time t2, an actual treatment beam $RAY_{ACTUAL}(t2)$ is being applied, which has been determined for the actual IGRT coordinate space based on a serial application of the relevant second registration (see FIG. 8C, transformation $T_{r0\text{-}t2}$), the inherent registration between the initial tomosynthesis image data set tomo(0) and the setup image data set 804 (see FIG. 8C, transformation $T_{O\text{-}r0}$), and the first registration (see FIG. 8C, transformation $T_{PO}$), as reflected in box 815 of FIG. 8C.

Advantageously, the relatively difficult and time-consuming registration between the initial medical image data set (setup image data set 804) and the pre-acquired image data set 802 (see FIG. 8C, transformation $T_{PO}$) does not need to take place during the treatment fraction after the beginning of radiation delivery, and only the very quick registrations between each subsequent tomosynthesis image data sets (tomo(t1), tomo(t2), and so forth) and the initial tomosynthesis image data tomo(0) needs to take place during the treatment fraction after the beginning of radiation delivery, thereby promoting at least one of reduced intra-fraction computational intensity and reduced treatment radiation delivery margins. Stated differently, the method of FIG. 8A provides an advantage that registrations between image data sets corresponding to different frames of reference do not require repeated computation throughout the radiation treatment fraction, thereby promoting at least one of reduced intra-fraction computational intensity and reduced treatment radiation delivery margins.

As illustrated by the box 807 in FIG. 8B, any of a wide variety of x-ray tomosynthesis acquisition methodologies and geometries can be used in conjunction with the method of FIG. 8A. Examples include the use of x-ray source arrays (see, for example, FIGS. 4-5, supra) or translated x-ray point sources (see, for example, FIG. 2, supra). Further examples include the use of a single tomosynthesis imaging arc (see, for example, FIG. 2, supra), stereoscopic implementations using dual tomosynthesis imaging arcs (see, for example, FIGS. 4-5, supra), and other implementations using three or more tomosynthesis imaging arcs. Stereoscopic tomosynthesis implementations such as those of FIGS. 4-5 supra can be particularly advantageous, each channel separately providing three-dimensional information that is somewhat reduced in resolution in a direction away from its source array, but that reduced resolution being at least partially compensated by virtue of the presence of image information from the other channel taken along a substantially different tomosynthesis imaging arc.

Figure 9A:
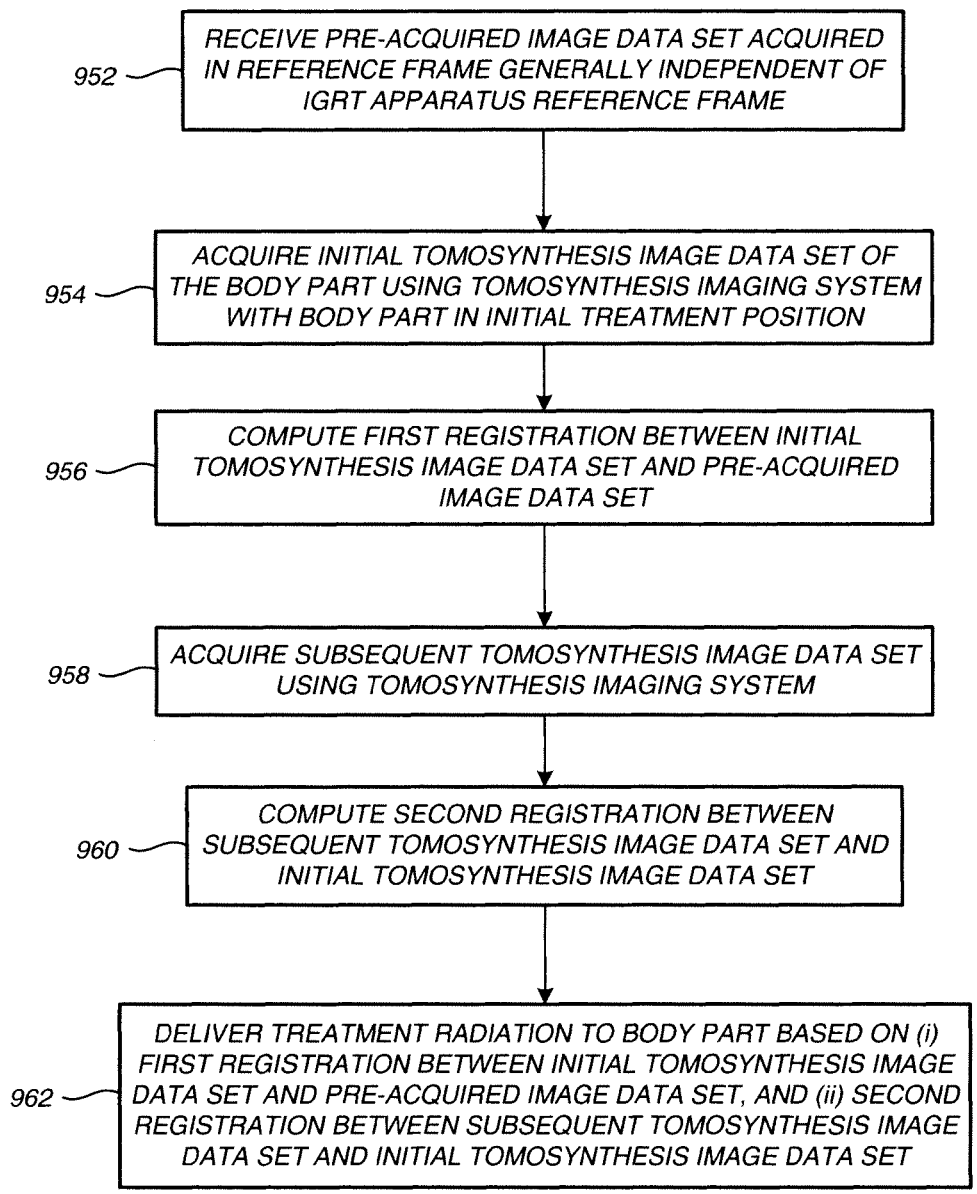
FIG. 9A illustrates image guided radiation treatment of a body part by an IGRT apparatus according to another preferred embodiment that is similar in certain respects to the preferred embodiment of FIG. 8A, except that the tomosynthesis imaging system of the IGRT apparatus is also used as the setup imaging system.
Figure 9B:
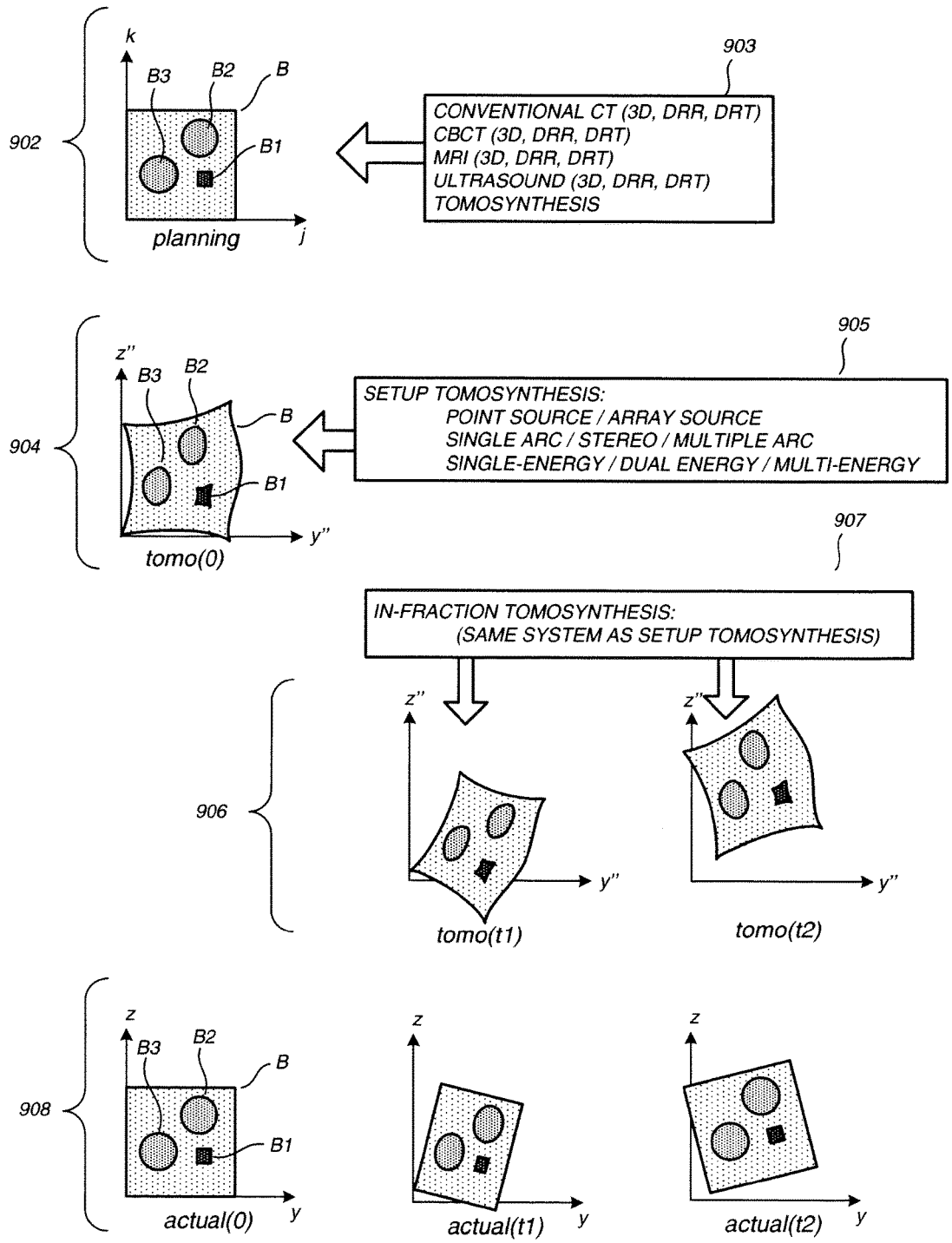
FIG. 9B illustrates a layout of simplified conceptual versions of the various images involved in the method of FIG. 9A.
Figure 9C:
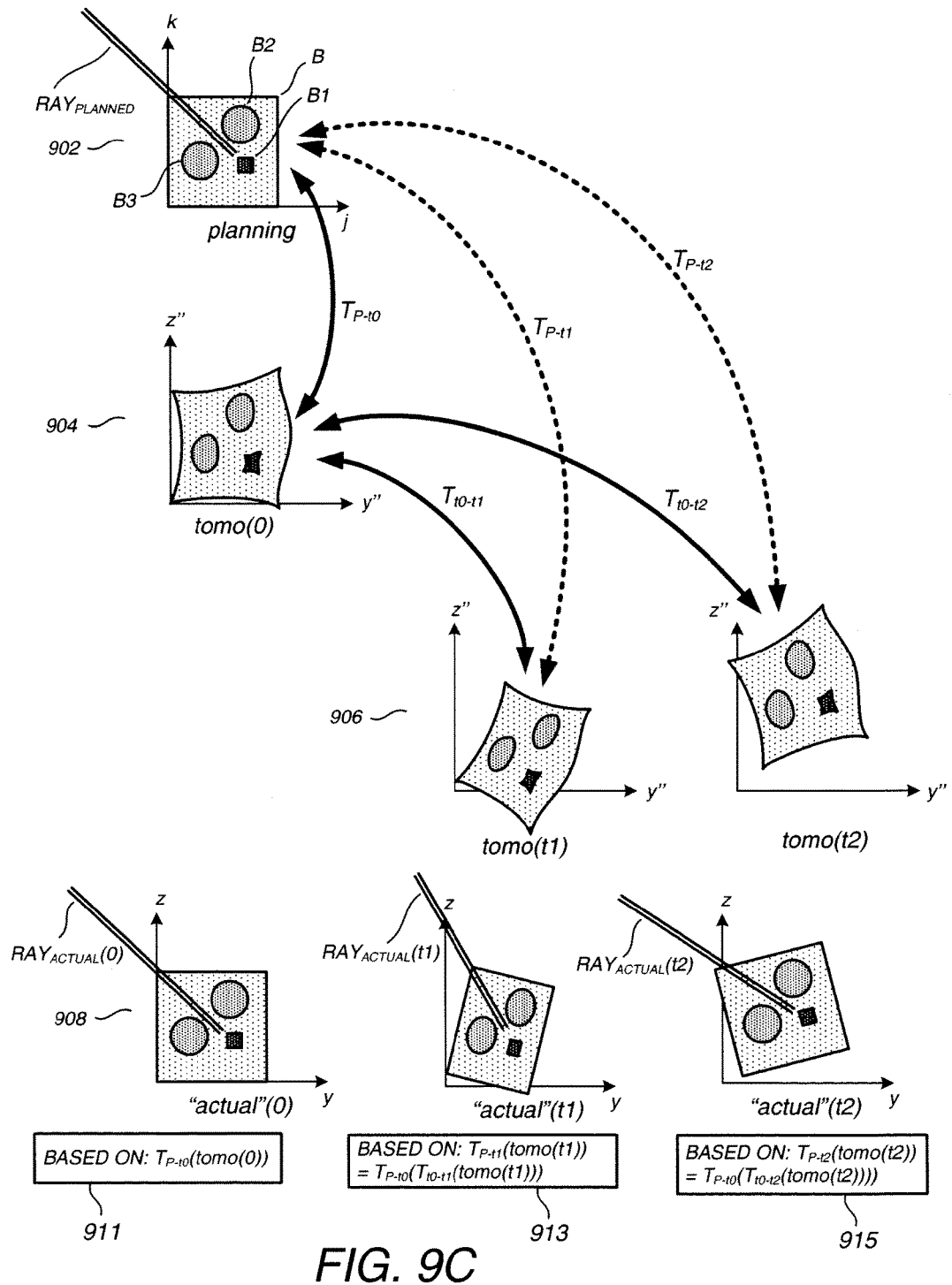
FIG. 9C illustrates the simplified conceptual image versions of FIG. 9B together with simplified graphical representations of transformations "T" associated with selected registrations therebetween to be performed according to one or more of the preferred embodiments.

FIG. 9A illustrates image guided radiation treatment of a body part by an IGRT apparatus according to another preferred embodiment that is similar in certain respects to the preferred embodiment of FIG. 8A, except that the tomosynthesis imaging system of the IGRT apparatus is also used as the setup imaging system. The method of FIG. 9A can be readily understood in view of the steps shown thereon and in view of FIGS. 9B-9C as shown. The method of FIG. 9A can be implemented, for example, using any of the IGRT systems of FIGS. 3-6, supra, and more generally any IGRT system that includes a kV x-ray tomosynthesis imaging capability. At step 952 a pre-acquired image data set of the body part is received, the pre-acquired image data set having been acquired in a reference frame generally independent of the reference frame of the IGRT apparatus (see FIG. 9A, pre-acquired image data set 902). As illustrated at block 903 of FIG. 9B, the pre-acquired image data set 902 may have been acquired using conventional CBCT, MRI, ultrasound, or tomosynthesis imaging equipment located in a different room than the treatment vault or otherwise having a different frame of reference than that of the IGRT apparatus. At step 954 an initial tomosynthesis medical image data set of the body part is acquired using the tomosynthesis imaging system while the body part is in an initial treatment position relative to the IGRT apparatus (see FIG. 9B, initial tomosynthesis image data set tomo(0)). As illustrated by the box 905 in FIG. 9B, any of a wide variety of x-ray tomosynthesis acquisition methodologies and geometries can be used including, but not limited to, the use of x-ray source arrays, translated x-ray point sources, a single tomosynthesis imaging arc, stereoscopic implementations using dual tomosynthesis imaging arcs, other implementations using three or more tomosynthesis imaging arcs, single-energy x-ray tomosynthesis imaging, dual-energy x-ray tomosynthesis imaging, and multiple x-ray energy tomosynthesis imaging. At step 956, a first registration between the initial tomosynthesis image data set tomo(0) and the pre-acquired image data set 902 is performed (see FIG. 9C, transformation $T_{P-t0}$). At step 958 a subsequent tomosynthesis image data set, i.e., an intrafraction tomosynthesis data set, is acquired using the tomosynthesis imaging system (see FIG. 9B, tomo(t1)). At step 960 a second registration between the subsequent tomosynthesis image data set tomo(t1) and the initial tomosynthesis image data set tomo(0) is performed (see FIG. 9C is a transformation $T_{t0-t1}$). At step 962 treatment radiation is delivered to the body part based at least in part on information derived from (i) the first registration between the initial tomosynthesis image data set tomo(0) and the pre-acquired image data set 902 (see FIG. 9C, transformation $T_{P-t0}$), and (ii) the second registration between the subsequent tomosynthesis image data set tomo (t1) and the initial tomosynthesis image data set tomo(t0) (see FIG. 9C, transformation $T_{t0-t1}$). The process can then be repeated for a subsequent tomosynthesis image data set tomo(t2) and each subsequent tomosynthesis image data set acquired thereafter during the treatment fraction. For one preferred embodiment, using the intrafraction time t1 as an example, the delivery of the treatment radiation comprises computing a third registration between tomo(t1) and the pre-acquired image data set 902 (see FIG. 9C, transformation $T_{P-t1}$) based on a serial application of the second registration (see FIG. 9C, transformation $T_{t0-t1}$) and the first registration (see FIG. 9C, transformation $T_{P-t0}$), as reflected in box 913 of FIG. 9C. As illustrated near the bottom of FIG. 9C, at time 0 the fraction begins with the actual treatment beam $RAY_{ACTUAL}(0)$ which is determined for the actual IGRT coordinate space based on the first registration between the initial tomosynthesis image data set tomo(0) and the pre-acquired image data set 902 (see FIG. 9C, transformation $T_{P-t0}$), as reflected in box 911 of FIG. 9C. As of time t2, an actual treatment beam $RAY_{ACTUAL}(t2)$ is being applied, which has been determined for the actual IGRT coordinate space based on a serial application of the relevant second registration (see FIG. 9C, transformation $T_{t0-t2}$) and the first registration (see FIG. 9C, transformation $T_{P-t0}$), as reflected in box 915 of FIG. 9C. Similar to the preferred embodiment of FIG. 8A, there is an advantage provided in that the relatively difficult and potentially time-consuming registration between the initial tomosynthesis image data set tomo(0) and the pre-acquired image data set 902 does not need to take place after the beginning of radiation delivery when time is of the essence, and instead is only required at time prior to the beginning of radiation delivery when time performance is less of an issue. During the treatment fraction after the beginning of radiation delivery, it is only the very quick and precise registrations between each subsequent tomosynthesis image data set (tomo(t1), tomo(t2), etc.) and the initial tomosynthesis image data tomo(0) that need to take place. At least one of reduced intra-fraction computational intensity and reduced treatment radiation delivery margins is promoted. As with the preferred embodiment of FIG. 8A, it is to be appreciated that the registration between the initial tomosynthesis image data set tomo(0) and the pre-acquired image data set 902 can be performed using a purely 3D version of the pre-acquired image data set 902, or using any of a rich variety of different expressions or abstractions based on the pre-acquired image data set 902 (e.g., DRRs and DRTs) without departing from the scope of the preferred embodiments. In one of many different examples, the registration can be of a tomo(0) volume to a DRT volume derived from a 3D version of the pre-acquired image data set 902, comprising the steps of identifying a first image slice within the DRT image volume for which an anatomical object of interest is in focus, identifying a second image slice within the tomo(0) volume for which the anatomical object of interest is in focus, and then performing a 2D-2D registration between said first and second image slices. In another example, there can be a pure 3D-3D registration between the DRT image volume and the tomo(0) volume. In still another example, there can be a pure 3D-3D registration between a pure 3D version of the pre-acquired image data set 902 (i.e., not a DRT abstraction) and the tomo(0) volume.

Figure 10:
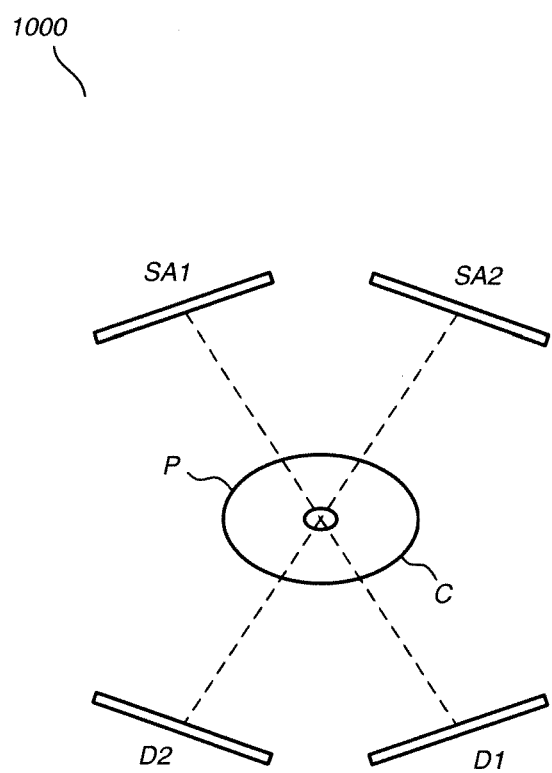
FIG. 10 illustrates a tomosynthesis imaging system as may be integrated into one or more of the above-described IGRT systems according to a preferred embodiment, the tomosynthesis imaging system providing dual-energy stereoscopic tomosynthesis imaging according to a preferred embodiment.

FIG. 10 illustrates a tomosynthesis imaging system 1000 as may be integrated into one or more of the above-described IGRT systems according to a preferred embodiment, the tomosynthesis imaging system 1000 providing dual-energy stereoscopic tomosynthesis imaging according to a preferred embodiment. Tomosynthesis imaging system 1000 comprises dual x-ray source arrays SA1 and SA2 and dual detectors D1 and D2. For the preferred embodiment of FIG. 10 and all subsequent preferred embodiments described hereinbelow, it is to be appreciated that although multiple adjacent and/or nearby x-ray source arrays may be illustrated as distinct physical components for clarity of presentation, they can be physically integrated into a common substrate or otherwise physically connected or coupled to form a common physical source device. Likewise, it is to be appreciated that although multiple adjacent and/or nearby detector arrays may be illustrated as distinct physical components for clarity of presentation, they can also be physically integrated into a common substrate or otherwise physically connected or coupled to form a common physical detector device. Source array SA1 and detector array D1 are configured, dimensioned, and positioned to provide a first x-ray tomosynthesis source-detector pair SA1-D1, i.e., a source-detector pair capable of acquiring two or more x-ray tomosynthesis projection images at two or more respective tomosynthesis projection angles. Source array SA2 and detector array D2 are likewise configured, dimensioned, and positioned to provide a second x-ray tomosynthesis source-detector pair SA2-D2. Preferably, the first and second source-detector pairs are mutually arranged in a generally stereoscopic arrangement relative to the target volume such as shown in FIG. 10.

Dual-energy imaging is a technique that can be used to improve the visibility of masked tissue in X-ray based imaging, and utilizes X-ray emissions having different energy spectra or profiles. X-ray images may be acquired of a patient or portion of a patient using two different X-ray energy profiles, one at a relatively high energy (e.g., 140 kV) and one at a relatively low energy (e.g., 80 kV), such that a different set of image data is acquired for each energy profile. The different sets of image data, when processed, may be used to construct different images that characterize the density or attenuating characteristics of the imaged volume. By decomposing the acquired image data, images may also be generated which differentially reflect the composition of the imaged volume, such as bone or soft tissue.

Provided according to one preferred embodiment is an image-guided radiation treatment (IGRT) apparatus including the first and second x-ray tomosynthesis source-detector pairs (SA1-D1, SA2-D2) positioned to acquire tomosynthesis projection images over first and second projection angle ranges, respectively, that are non-overlapping with each other. First and second sets of tomosynthesis projection images of the target volume are acquired at distinct first and second x-ray energy levels, respectively (e.g., 80 kV and 140 kV), using the respective first and second x-ray tomosynthesis source-detector pairs.

The first and second sets of tomosynthesis projection images are then processed to generate respective first and second tomosynthesis reconstructed image sets of the target volume. Any of a variety of different tomosynthesis reconstruction algorithms can be used including, but not limited to, filtered backprojection (FBP), matrix inversion tomosynthesis (MITS), maximum likelihood expectation maximization (MLEM), and iterative ordered-subset convex (OSC) algorithms based on a maximum-likelihood models.

The first and second tomosynthesis reconstructed image sets are then processed in conjunction with each other on a locationwise basis (e.g., voxelwise basis) within the target volume to generate a dual-energy processed image set. For one preferred embodiment, the processing of the first and second tomosynthesis reconstructed image sets comprises registration (either by a known physical transformation between the imaging coordinate spaces or by image-based registration) and subtraction processing and/or other decomposition into soft-tissue and bone image components. Treatment radiation is delivered to the treatment target within the target volume based at least in part on the dual-energy processed image set.

For one preferred embodiment, the array sources SA1 and SA2 are constructed and/or modified to include a source collimation capability such that no primary x-ray passing through the target volume from the first source SA1 impinges upon the second detector D2, and no primary x-ray passing through the target volume from the second source SA2 impinges upon the first detector D1. Advantageously, the first and second sets of tomosynthesis projection images can then be acquired simultaneously, thereby reducing imaging time and reducing the possibility the target volume moves in between image acquisition.

For one preferred embodiment, the first and second sets of tomosynthesis projection images are simultaneously, or substantially simultaneously, acquired at periodic intervals corresponding to a common phase of a physiological movement cycle of the patient (e.g., a respiratory cycle or a heartbeat cycle), and the IGRT apparatus is further equipped with a non-x-ray-based movement sensing system that processes continuously monitored external patient movement data in conjunction with a correlation model to predictively compute target volume movement during the physiological movement cycle. The dual-energy processed image set is used to update the correlation model at each acquisition cycle.

Optionally, the source arrays SA1 and SA2 can each alternate between low-energy and high-energy emission modes at respective periodic imaging cycles. For one preferred embodiment, the source arrays SA1 and SA2 can be in-phase with each other (i.e., both emitting at low energy, then both emitting at high energy, etc.), while for another preferred embodiment, the source arrays SA1 and SA2 can be out of phase with each other (i.e., one emitting at low energy while the other emits at high energy).

Although dual-energy x-ray tomosynthesis has been found particularly advantageous in the context of the stereoscopic applications, the scope of the present teachings is not so limited and includes alternative preferred embodiments in which only a single tomosynthesis imaging arc is involved, either by virtue of using only a single x-ray source array or by virtue of using multiple x-ray source arrays that collectively extend over only a single tomosynthesis imaging arc. Moreover, for both non-stereoscopic and stereoscopic preferred embodiments, a variety of different methods of configuring and/or operating one or more of the x-ray sources is within the scope of the present teachings including, for example: (i) rapidly varying the electron accelerating potential of each of the x-ray sources between low voltage and high voltage modes to achieve respective low and high energy x-ray tomosynthesis projection images at closely spaced points in time; (ii) positioning dedicated low-energy x-ray sources and dedicated high-energy x-ray sources adjacently to each other along the x-ray source array and interleaving their operation on either (a) a per tomosynthesis imaging set basis (i.e., all projection angles at low energy, then all projection angles at high energy), or (b) a per projection angle basis (i.e., a low-energy projection image at a first angle followed by a high energy projection image at that first angle, then a low-energy projection image at a second angle followed by a high energy projection image at that second angle, and so on); and (iii) a combination of temporally interleaving and spatial interleaving of the x-ray source energies, for example, in a manner analogous to the discrete RGB emission sources of an LCD color display.

Although applicable in a wide variety of medical imaging environments, the preferred embodiments described herein in relation to stereo and non-stereo dual-energy tomosynthesis are particularly advantageous for application in radiation treatment environments where it is impossible and/or unrealistic to expect a patient to temporarily "freeze" while a set of tomosynthesis projection images is acquired. For preferred embodiments in which the low-energy and high-energy tomosynthesis projection images are acquired simultaneously, there is a further advantage provided in that there is an intrinsic time registration between them that, in conjunction with a spatial registration established by virtue of the known imaging geometries involved, provides for proper registration and feature alignment between the low and high energy volumes, which in turn enables fast and accurate generation of a dual energy processed data volume.

Figure 11A:
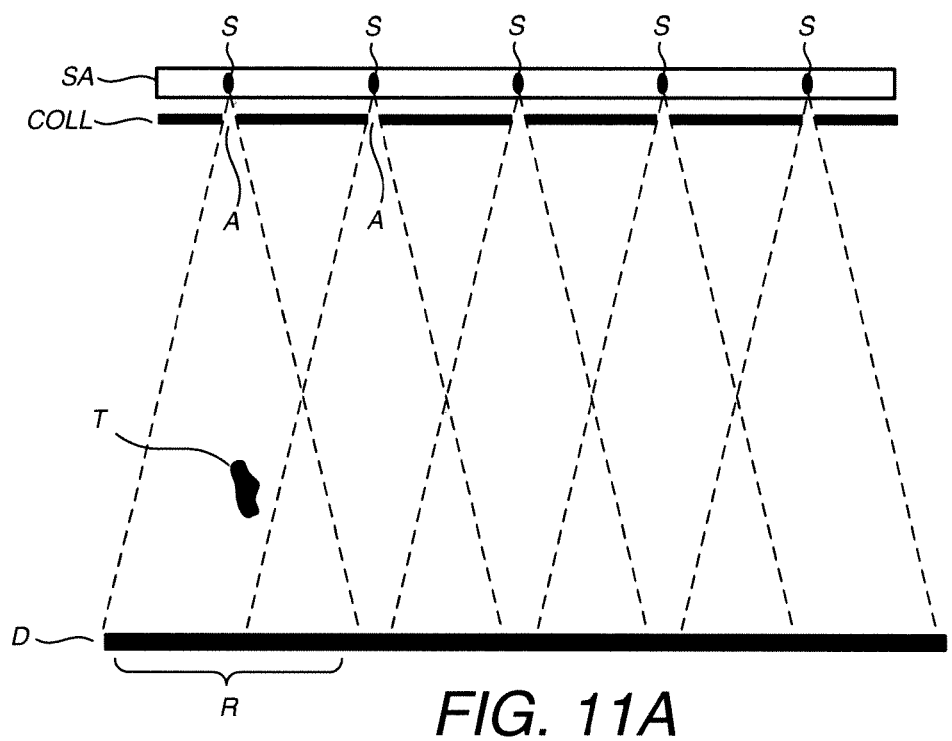
FIG. 11A illustrates selective collimation of x-ray emission from an x-ray source array according to a preferred embodiment.

FIG. 11A illustrates selective collimation of x-ray emission from an x-ray source array according to a preferred embodiment. An x-ray source array SA is provided with a linear, two-dimensional, and/or three-dimensional arrangement of individually addressable and dynamically activatible x-ray sources S. For clarity of presentation herein, individual x-ray sources of an x-ray source array are illustrated simply by the location of their focal spot, as shown in FIG. 11A. For some preferred embodiments, the individual x-ray sources S can be referred to as x-ray source pixels. For clarity of presentation, many of the preferred embodiments are graphically represented in the drawings in the context of one-dimensional (linear) x-ray source arrays and associated one-dimensional depictions of corresponding detector arrays. It is to be appreciated, however, that these representations are merely illustrative and that the corresponding two-dimensional and three-dimensional counterparts of these teachings are also embodied within these descriptions as would be apparent to a person skilled in the art in view of the present disclosure.

Also illustrated in FIG. 11A is a collimation device COLL comprising a light absorbing material, such as lead or tungsten, into which is formed apertures A that correspond respectively to the x-ray sources S. For one preferred embodiment, each aperture A is configured and dimensioned to provide a relatively narrow, fixed cone beam angle for its respective source that is incident upon a subregion R of the detector D. Each combination of source and aperture (S/A) can be called a "pixel" of the source array SA. For another preferred embodiment, one or more of the apertures A can be actuated, such as by using microelectromechanical systems (MEMS) technology to vary the cone beam angle for that pixel, and/or to entirely block (turn off) and unblock (turn on) that pixel. Preferably, each S/A pixel of the source array SA can be individually addressed and actuated. Alternatively, the pixels can be addressed and controlled on a groupwise basis. Without loss of generality hereinbelow, the activation/deactivation of a particular pixel of an x-ray source array is described in terms of the addressable electrical activation/deactivation of the corresponding x-ray source. However, it is to be appreciated that the activation/deactivation of one or more of the pixels of an x-ray source can alternatively be achieved by a MEMS-based blocking or unblocking of that source pixel without departing from the scope of the present teachings.

With exemplary non-limiting reference to FIG. 11A, provided in one preferred embodiment is a method for reduced dosage x-ray imaging (or, alternatively, higher quality imaging for a predefined x-ray dose) of a target structure T using an x-ray source array SA and an x-ray collimating device COLL. The x-ray collimating device COLL is configured and dimensioned to individually collimate x-ray radiation from each of a first plurality of x-ray sources S onto a corresponding subgroup of detector pixels covering an area R substantially smaller than the predefined imaging area of the detector D. Thus, the x-ray collimating device COLL is configured such that, for each x-ray source S in the source array SA, there is a predetermined subregion R of detector pixels that will receive primary x-ray radiation therefrom. For this preferred embodiment, it is known that the target structure T will project onto a relatively small subregion of the imaging area of a detector D in view of the size of the target volume and the overall imaging geometry presented. Based on knowledge of the approximate location of the target structure T, only those x-ray sources S necessary to encompass the target structure T with respect to its projection onto the detector D are activated. The digital detector D is selectively operated such that only the detector pixels corresponding to the currently activated x-ray source(s) are used to measure x-ray radiation. According to one preferred embodiment, the knowledge of the location of the target structure T can be determined from previous medical images of the patient in conjunction with current knowledge of the position of the patient relative to the imaging geometry.

When compared to a prior art scenario in which a single x-ray source covering the entire predefined imaging area is used to achieve comparable x-ray flux through the target, and assuming (as is often the case) that there is patient anatomy generally surrounding the target structure T, the above-described preferred embodiment can provide a similar-quality image at a substantial x-ray dose reduction. Alternatively, for a similar overall x-ray dose as would be applied to the patient by the prior art single x-ray source, a higher-quality image can be obtained by increasing the power of the activated x-ray sources in the x-ray source array.

Figure 11B:
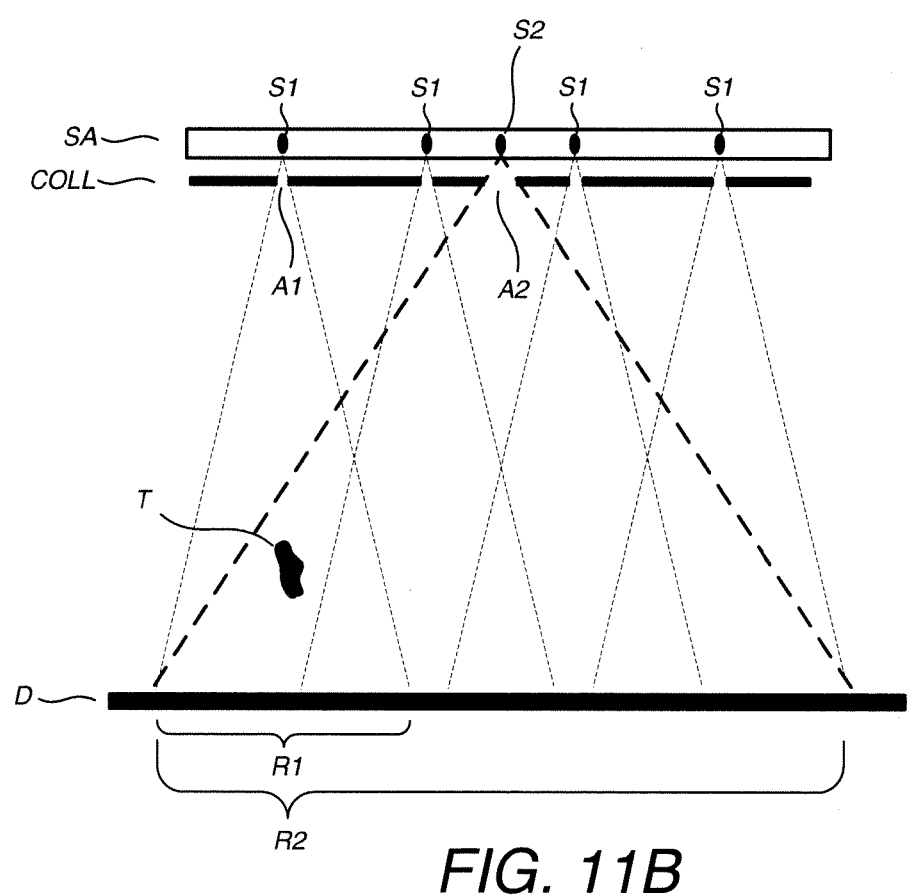
FIG. 11B illustrates selective collimation of x-ray emission from an x-ray source array according to another preferred embodiment.

FIG. 11B illustrates selective collimation of x-ray emission from an x-ray source array according to another preferred embodiment. An x-ray source array SA and collimator COLL is provided with a first group of pixels or source/aperture pairs S1/A1 that are similar in function to the pixels or source/aperture pairs S/A of FIG. 11A, with each of them providing a relatively narrow, fixed cone beam angle for its respective source that is incident upon a subregion R1 of the detector D. Also provided is a second source S2 and corresponding aperture A2 mutually configured to illuminate a region R2 of the detector D that is substantially larger than each subregion R1. The second source S2 can optionally be termed a "pilot" source. For one optional preferred embodiment, the region R2 covers a substantial entirety of the imaging area available on detector D. The device of FIG. 11B can be used in a method for reduced dosage x-ray imaging (or, alternatively, higher quality imaging for a predefined x-ray dose) similar to the method described above in relation to FIG. 11A, with a further advantage that the x-ray source S2 can be operated prior to the x-ray source(s) S1 to acquire a "pilot image" of the overall target volume containing the target structure T. The pilot image can be a relatively low-quality image acquired with a very low x-ray dose, since it is only being used to identify the general locality of the target structure T within the larger target volume on the detector D. Thus, using the device of FIG. 11B, it is no longer required to acquire a priori target volume location from external data sources. In an alternative preferred embodiment, instead of using an added "pilot" x-ray source to initially localize the target structure, a plurality of the source array members S1 can be separately operated one at a time, at very brief low-dose imaging intervals, to acquire a set of smaller "pilot" images that can be processed to identify the location of the target structure.

Figures 1, 17:
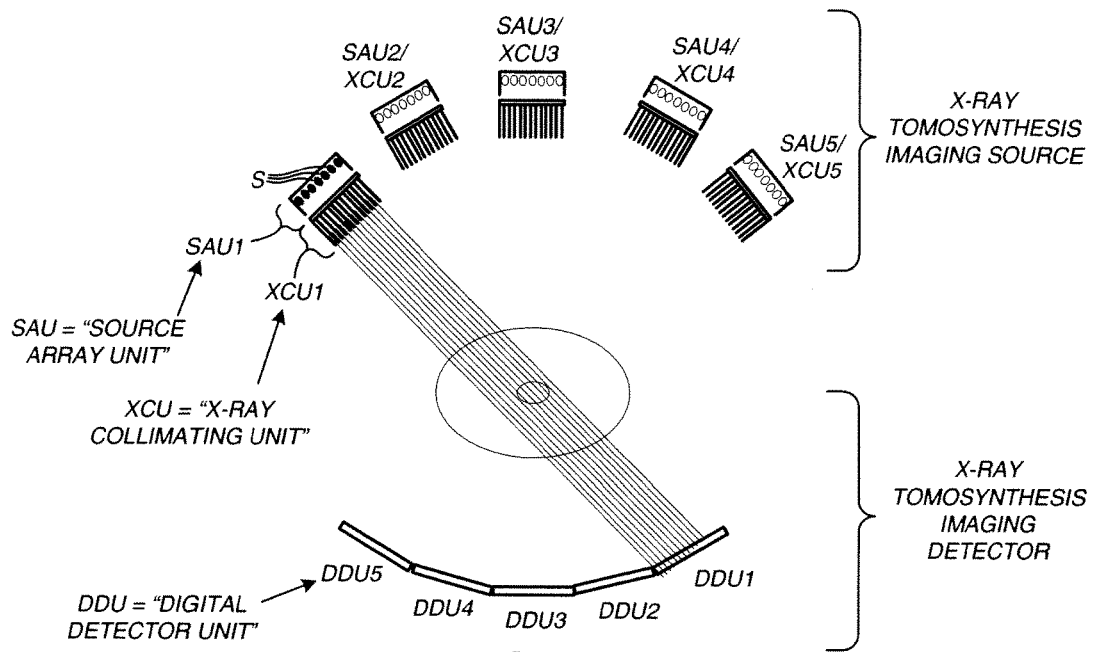
Figures 2, 17:
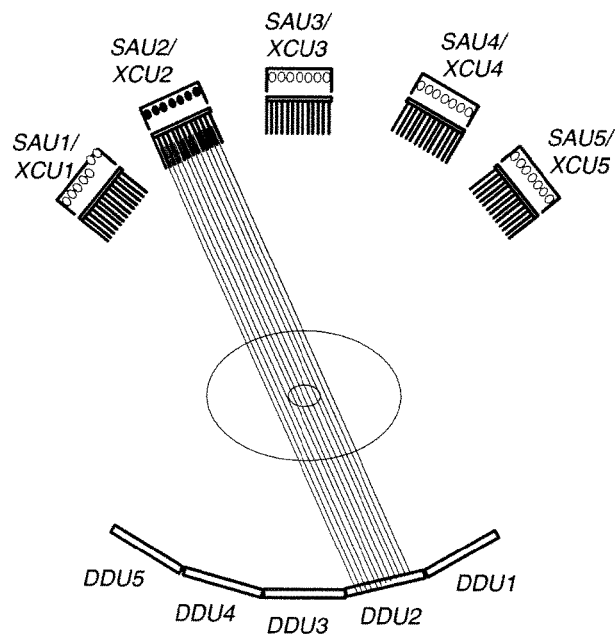
Figures 3, 17:
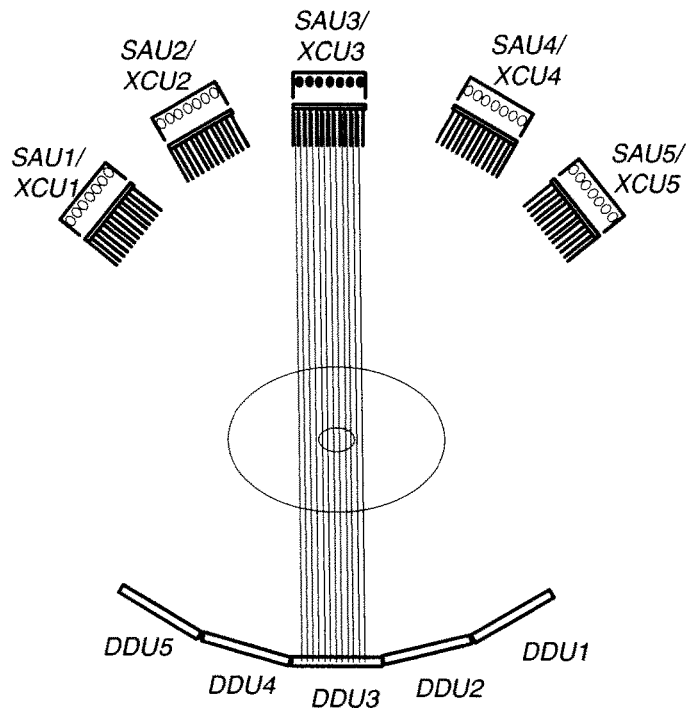
Figures 4, 17:
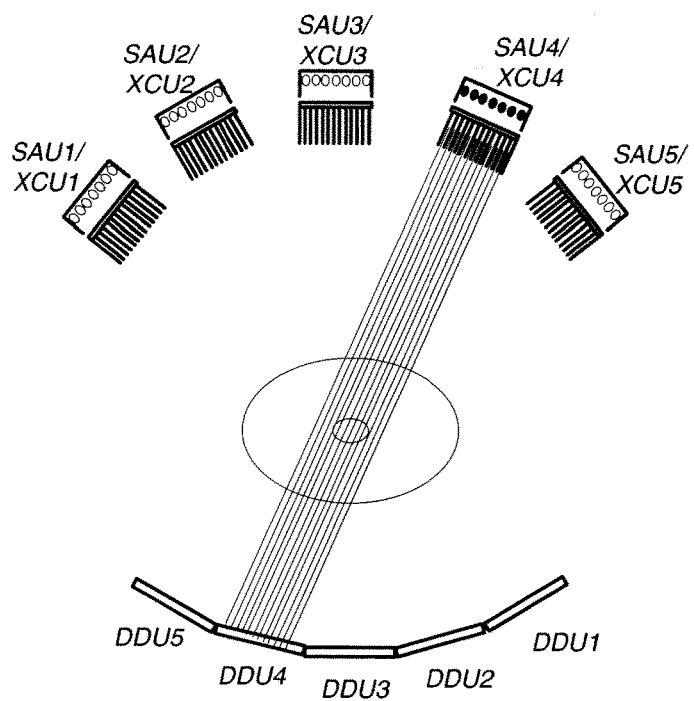
Figures 5, 17:
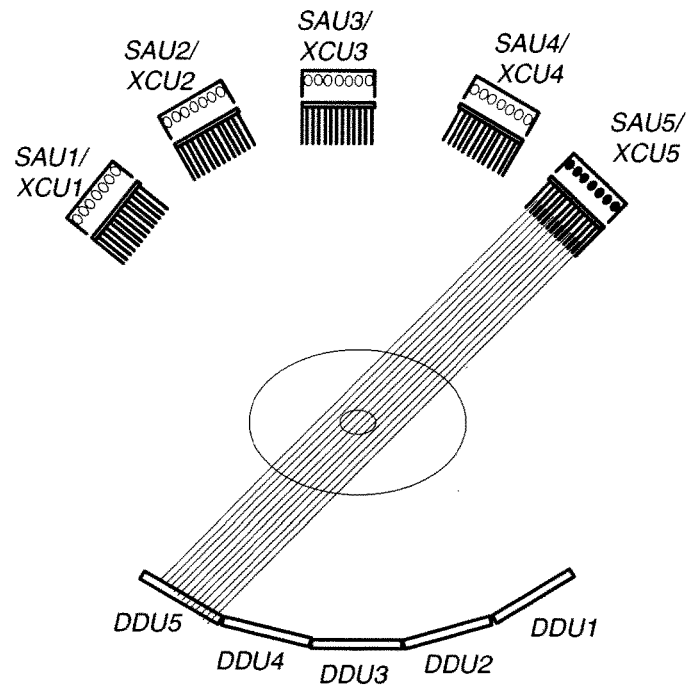

Also provided according to one or more preferred embodiments are methods and systems for reduced-dosage and/or higher quality x-ray tomosynthesis imaging of a target structure contained within a target volume, based on an extension to tomosynthesis of the devices and methods described above in relation to FIGS. 11A-11B. An x-ray tomosynthesis imaging source is provided comprising a plurality of x-ray source array units disposed at a respective plurality of tomosynthesis projection angles relative to the target volume, each x-ray source array unit comprising a first plurality of x-ray sources spatially distinct from each other. Referring forward briefly to FIG. 17-1, an example of an x-ray tomosynthesis imaging source is shown that comprises five x-ray source array units labeled SAU1 through SAU5. Each x-ray source array unit SAU1-SAU5 comprises a first plurality of x-ray sources S. Also provided is an x-ray tomosynthesis imaging detector comprising a plurality of digital detector units respectively disposed opposite the plurality of x-ray source array units relative to the target volume, each digital detector unit being thereby paired with a corresponding one of the x-ray source array units, each digital detector unit comprising an array of detector pixels extending over a predefined imaging area. Referring forward briefly to FIG. 17-1, an example of an x-ray tomosynthesis imaging detector is shown that comprises five digital detector units labeled DDU1 through DDU5. Provided in association with each x-ray source array unit is an x-ray collimating unit disposed between that x-ray source array unit and the target volume, the x-ray collimating unit being positioned closer to that x-ray source array unit than to the target volume, the x-ray collimating unit being configured and dimensioned to individually collimate x-ray radiation from each of the first plurality of x-ray sources of that x-ray source unit onto a corresponding subgroup of detector pixels of the paired digital detector unit that cover an area substantially smaller than the predefined imaging area of the paired digital detector unit. Referring forward briefly to FIG. 17-1, there are shown five x-ray collimating units labeled XCU1 through XCU5.

For this tomosynthesis-related preferred embodiment, it is known that the target structure will project onto a relatively small subregion of the imaging area of each digital detector unit in view of the size of the target structure within the target volume and the overall imaging geometry presented. Based on knowledge of the location of the target structure within the target volume, only particular ones of the first plurality of x-ray sources of each x-ray source array unit necessary to encompass the target structure with respect to its projection onto the paired digital detector unit are activated. Each digital detector unit is selectively operated such that only the detector pixels corresponding to the currently activated x-ray source(s) of the corresponding x-ray source array are used to measure x-ray radiation. According to one preferred embodiment, the knowledge of the location of the target structure within the target volume can be determined from previous medical images of the patient in conjunction with current knowledge of the position of the patient relative to the imaging geometry.

According to another preferred embodiment, a previously acquired low-dose "pilot" tomosynthesis image set is used to localize the target structure. More particularly, provided on each of the x-ray source array units is an additional x-ray source distinct from the first plurality of x-ray sources, and the associated x-ray collimating unit is configured to collimate x-ray radiation from the additional x-ray source onto a substantial entirety of the predefined imaging area of the paired digital detector unit. At a previous time interval, the plurality of x-ray source array units and the corresponding digital detector units are operated to acquire a plurality of "pilot" tomosynthesis projection images of the target volume within which the target structure is disposed. In acquiring the "pilot" tomosynthesis projection images, only the additional x-ray source of each x-ray source array unit is operated. The "pilot" tomosynthesis projection images are then processed to localize the target structure within the target volume.

Figure 11C:
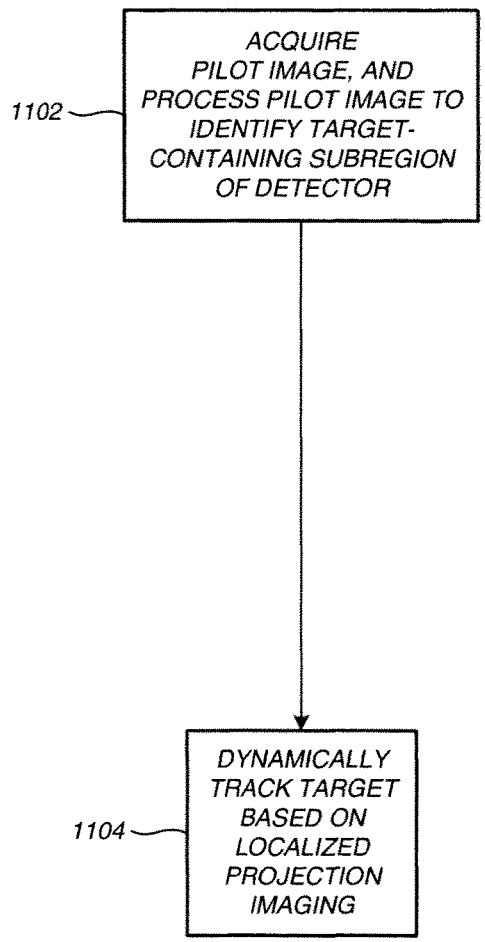
FIG. 11C conceptually illustrates two-dimensional imaging and tracking of a target according to a preferred embodiment.
Figure 11D:
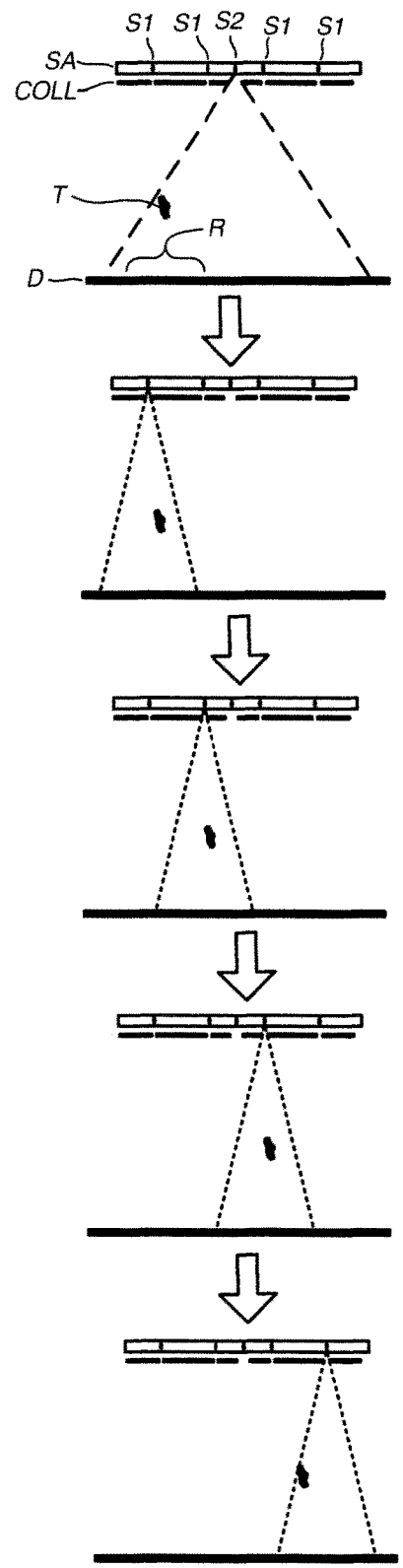
FIG. 11D conceptually illustrates two-dimensional imaging and tracking of a target according to a preferred embodiment.

FIGS. 11C-11D conceptually illustrate two-dimensional imaging and tracking of a target according to a preferred embodiment using, by way of example, the two-dimensional x-ray imaging apparatus of FIG. 11B. At step 1102, a pilot image is acquired using the pilot x-ray source S2, and the pilot image is processed to identify a target-containing subregion of the detector. At step 1104, the target is dynamically tracked using localized projection imaging from individual ones of the x-ray sources S1. A variety of different segmentation and predictive location estimation algorithms can be used to predict where the target structure T will be relative to the detector D, and to thereby select which of the sources S1 to activate at any particular imaging interval. As an alternative to pilot imaging using the source S2, the sources S1 can be sequentially activated, one at a time, to acquire a set of smaller pilot images that can be processed to identify the initial location of the target structure.

Figure 12A:
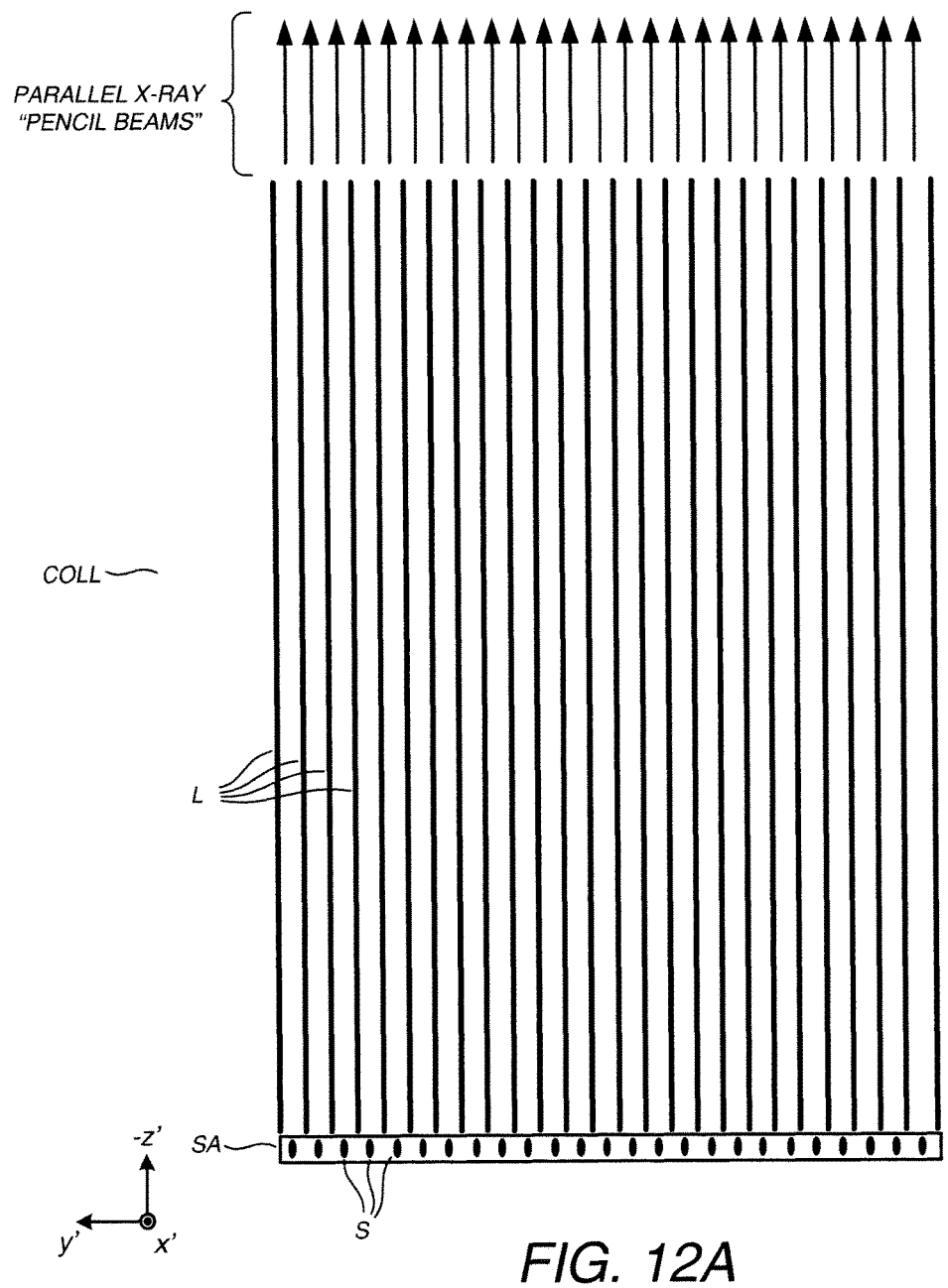
FIG. 12A illustrates an x-ray source collimation device COLL and an x-ray source array SA according to a preferred embodiment.

FIG. 12A illustrates an x-ray source collimation device COLL and an x-ray source array SA according to a preferred embodiment. The collimation device COLL comprises a plurality of slat-like louvers L arranged in parallel fashion over the x-ray source array SA, each pair of louvers L forming a thin collimating slab that directs x-ray radiation in the direction of the thin slab. The louvers L are formed from an x-ray opaque material such as tungsten. For the preferred embodiment of FIG. 12A, the louvers L are directed normal to an emission surface of the source array SA, collimating the generally isotropic x-rays emitted from the x-ray sources S into thin slabs parallel to the x-z plane. To collimate the x-rays into a strictly vertical direction (the "x" direction of FIG. 12A), a second array of similarly constructed louvers parallel to the x-y plane is stacked atop the arrangement of FIG. 12A. For one preferred embodiment, both layers of louvers L are fixably disposed in predetermined directions, while for another preferred embodiment, one or both of the layers has an adjustable direction.

Figure 12B:
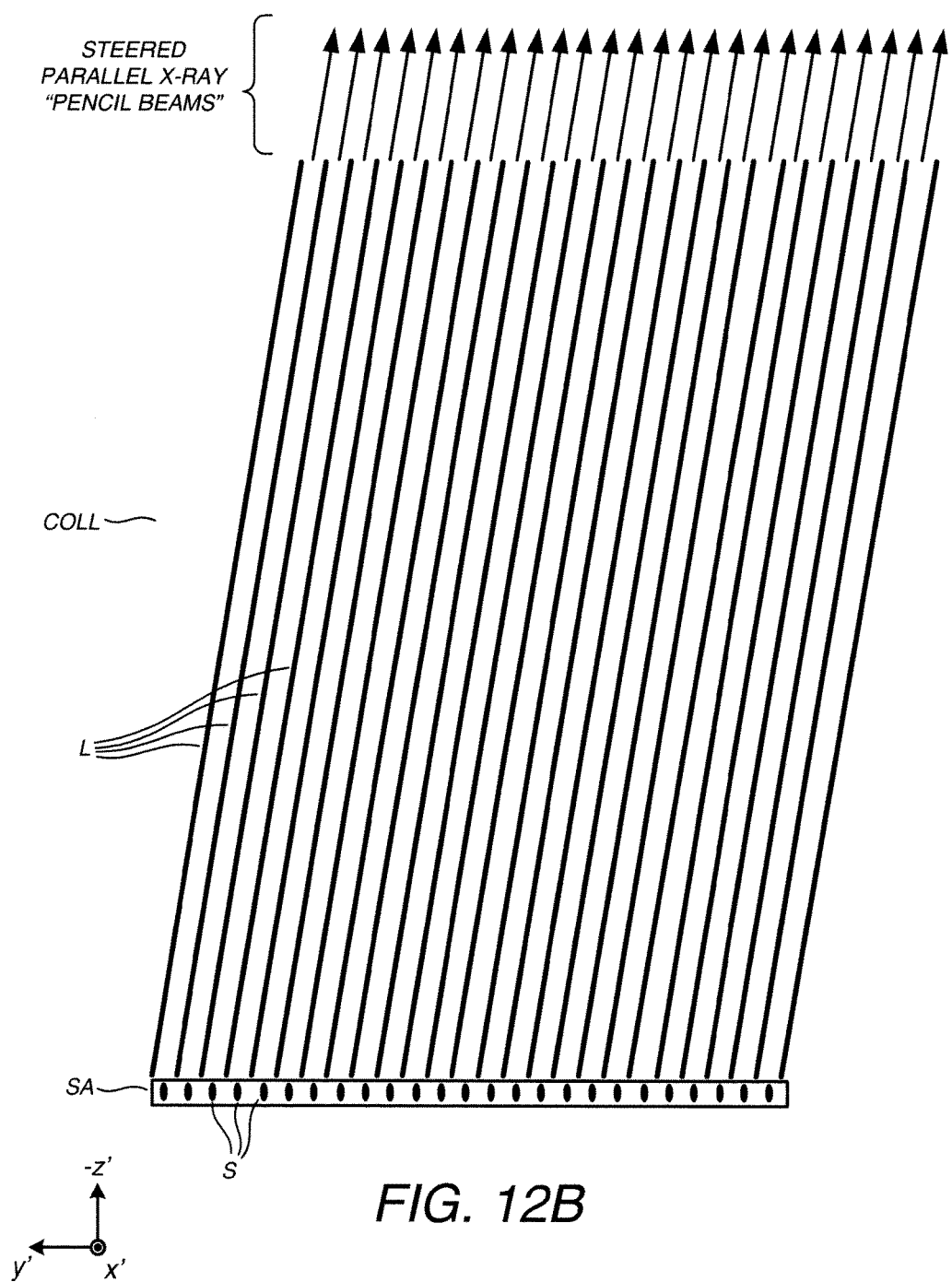
FIG. 12B illustrates an x-ray source collimation device COLL and an x-ray source array SA according to a preferred embodiment in which the x-ray beams are dynamically steered according to actuation of the direction of the louvers L.

FIG. 12B illustrates an x-ray source collimation device COLL and an x-ray source array SA according to a preferred embodiment in which the x-ray beams are dynamically steered according to actuation of the direction of the louvers L. Any of a variety of control and actuation mechanisms (not shown) can be used to manipulate the collimation angle including, but not limited to, motor-driven mechanical rods and hinges, electrostatic or magnetostatic actuation schemes, and various other mechanical, electrical, and/or microelectromechanical (MEMS) based actuation schemes.

Figure 13:
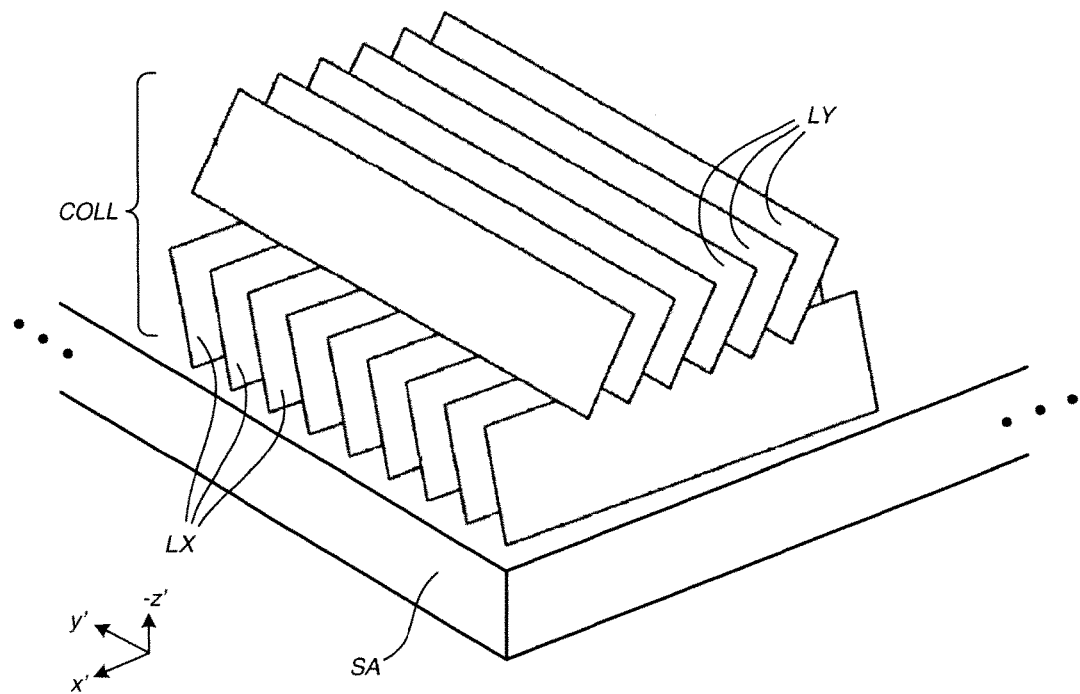
FIG. 13 illustrates a simplified perspective view of an x-ray source collimation device COLL and an x-ray source array SA according to a preferred embodiment, the collimation device COLL comprising a first steerable louver array LX and a second steerable louver array LY.

FIG. 13 illustrates a simplified perspective view of an x-ray source collimation device COLL and an x-ray source array SA according to a preferred embodiment, the collimation device COLL comprising a first steerable louver array LX and a second steerable louver array LY. The collimation device COLL is designed to collimate the x-ray radiation into a population of substantially parallel x-ray pencil beams, preferably such that each primary ray impinges upon the detector at the same angle of incidence. A rich variety of strategic illumination and imaging schemes are enabled by virtue of the population of parallel pencil beams that can reduce x-ray imaging dose and/or increase image quality, particularly when the beams are simultaneously steerable and when each beam is individually activated by one or more separate electronic activation signals. Moreover, distortion artifacts traditionally associated with single-point x-ray sources due to spreading of the beam are avoided.

Because it functions by absorption of x-ray photons that are not emitted in the aimed direction, which is on the order of 99% of all emitted x-ray photons, the collimation device COLL is not necessarily efficient in the sense of overall power requirements, and the device will furthermore operate at relatively high temperatures that may require forced air or liquid cooling systems. However, in terms of x-ray dose to the patient, the collimation device COLL is highly efficient, with the surviving pencil-beam x-ray photons being judiciously aimed at the region of the particular target structure of interest within the patient.

For one preferred embodiment, the collimating device COLL is similar in materials and construction to one or more single photon emission computed tomography (SPECT) collimators disclosed in U.S. Pat. No. 7,345,282B2, which is incorporated by reference herein. However, the SPECT collimators disclosed in U.S. Pat. No. 7,345,282B2 are incorporated into a substantially different environment than two-dimensional x-ray imaging and x-ray tomosynthesis imaging, and furthermore are detector-mounted collimators rather than source-mounted collimators.

For one preferred embodiment, the spatial separation of the arrayed louvers L corresponds directly to the spacings of x-ray sources S, and each source S is disposed midway between respective louvers L in each spatial direction, which is shown in one dimension (the y-direction) in FIGS. 12A-12B. By way of example only and not by way of limitation, x-ray source array SA may be characterized by an average x-ray source focal spot size of 250 µm and an average focal spot spacing of about 1 mm. For this case, the louvers L will likewise be spaced apart by 1 mm, may each have a thickness of about 0.2 mm, and may each have a height of about 5 cm. For another preferred embodiment, the x-ray source array SA may be characterized by an average x-ray source focal spot size of 400 µm and an average focal spot spacing dF in the range of 0.5 mm and 2 mm, and the louvers L may be spaced apart by dF, may each have a thickness dimension of between about 0.1 mm and 0.3 mm, and may each have a height in the range of 4 cm-8 cm. In other preferred embodiments, there may be an x-ray source located only at every second or third inter-louver gap (or generally every Nth inter-louver gap) so that there are no overlaps between respective illumination regions of the digital detector.

Figure 14:
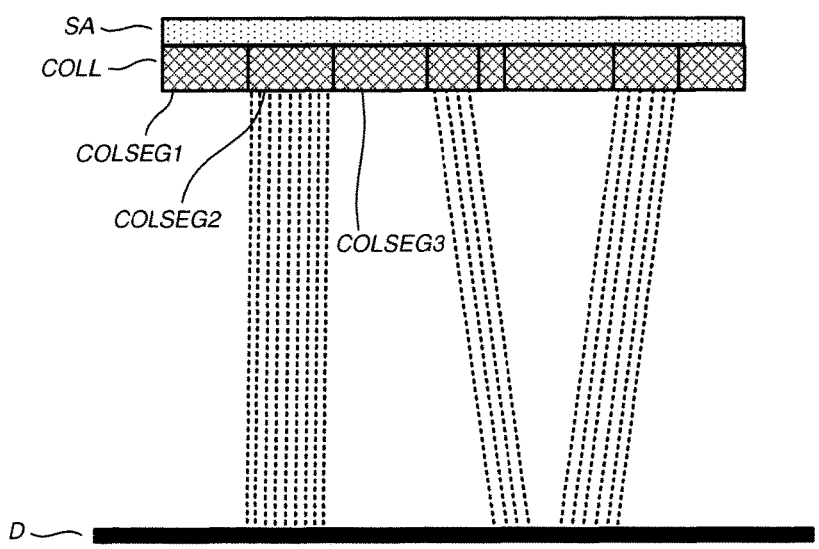

FIG. 14 illustrates a smaller scale (i.e., less detailed) conceptual side view of an x-ray source array SA and collimator COLL according to a preferred embodiment, wherein the collimator COLL is segmented into a number of separately controlled segments COLSEG1, SOLSEG2, COLSEG3, and so on. In the illustration of FIG. 14, individual x-ray sources in the source array SA and individual louvers in the collimator COLL are not illustrated, it being understood that there is a generally a large population of each of them per unit distance. The individual segments COLSEG can be a variety of different shapes and sizes, and can range from association with a single x-ray source (i.e., aligned with a single x-ray source focal spot) to hundreds or even thousands of x-ray sources without departing from the scope of the present teachings. Moreover, there can be anywhere from a single segment COLSEG to tens, hundreds, or even thousands of such segments distributed across the emitting surface of the source array SA without departing from the scope of the present teachings. In one preferred embodiment, the collimation direction of each segment COLSEG is separately controlled, each segment thereby being operable as an independent "floodlight" that can be independently aimed in a desired direction. By virtue of the combination of (i) independently steerable collimation segments, together with (ii) independently controllable x-ray sources throughout the source array, a very large and rich variety of controlled target illumination scenarios are made possible, each of which is within the scope of the preferred embodiments.

Figure 15:
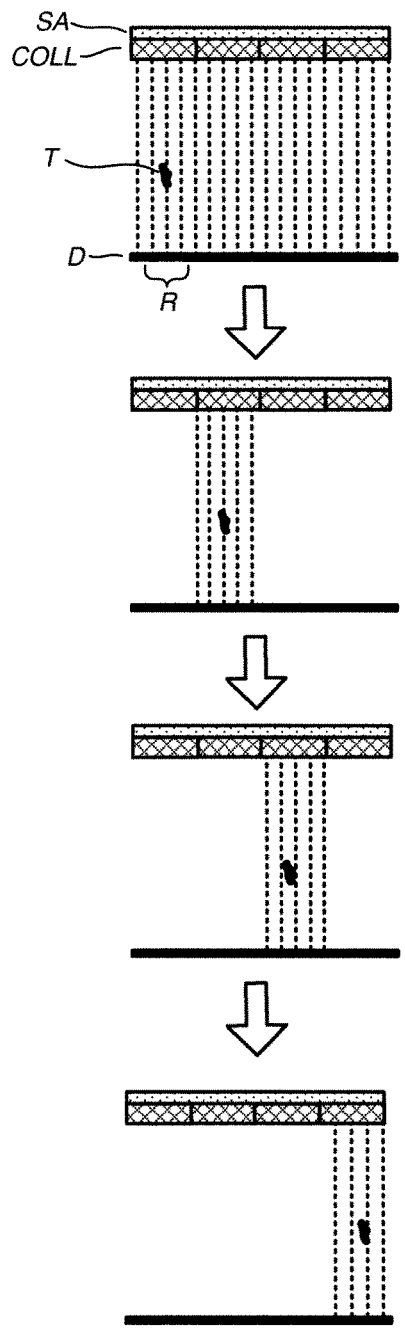
FIGS. 15-16 each illustrate reduced dosage x-ray imaging (or higher quality imaging for a predefined x-ray dose) and target tracking of a target structure T using an x-ray source array SA and an x-ray collimating device COLL according to a preferred embodiment.
Figure 16:
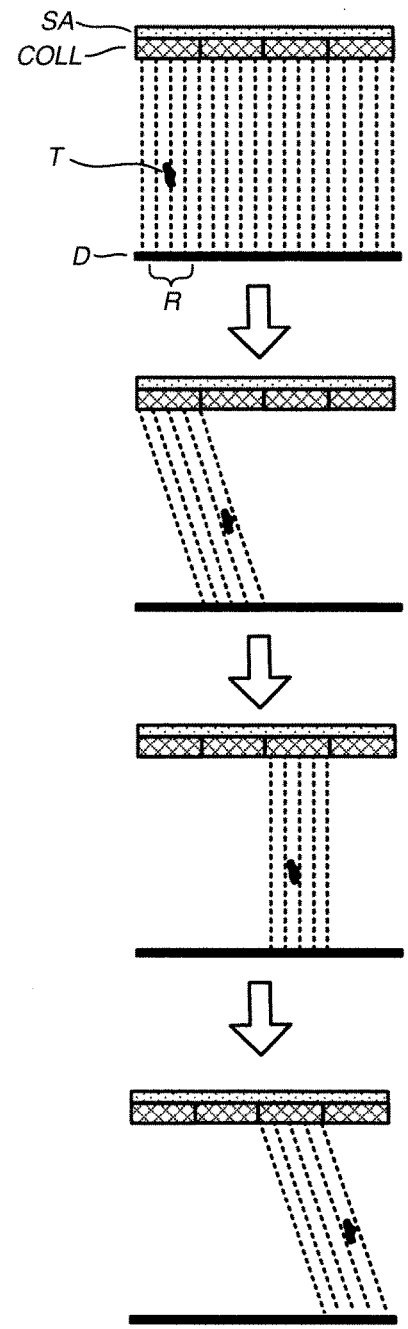

FIGS. 15-16 each illustrate reduced dosage x-ray imaging (or higher quality imaging for a predefined x-ray dose) and target tracking of a target structure T using an x-ray source array SA and an x-ray collimating device COLL according to a preferred embodiment. As would be appreciated by a person skilled in the art in view of the present disclosure, FIGS. 15-16 represent but two examples of a large number of different imaging/tracking scenarios that are made possible using x-ray source arrays having individual source control and collimating devices having segmentwise directional control according to one or more of the preferred embodiments. For each of the examples of FIGS. 15-16, a low dose "pilot" image is first obtained by illuminating the entire imaging area of the detector with parallel x-ray pencil beams. The low dose can be achieved, for example, by only activating every second, third, or $N^{th}$ x-ray source in the x-ray source array SA. In the example of FIG. 15, the target structure T is tracked by virtue of non-steered x-ray pencil beams that are selectively activated on a segmentwise basis across the x-ray source array SA. In the example of FIG. 16, the target structure T is tracked by virtue of a combination of selective segmentwise x-ray source activation and active steering of the x-ray pencil beams.

FIG. 17-1 through FIG. 17-5 illustrate acquiring a set of x-ray tomosynthesis projection images of a target volume according to a preferred embodiment. Provided is an x-ray tomosynthesis imaging source comprising a plurality of x-ray source array units SAU1-SAU5 disposed at a respective plurality of tomosynthesis projection angles relative to the target volume, each x-ray source array unit SAU comprising a first plurality of x-ray sources S spatially distinct from each other. Also provided is an x-ray tomosynthesis imaging detector comprising a plurality of digital detector units DDU1-DDU5 respectively disposed opposite the x-ray source array units SAU1-SAU5 relative to the target volume, each digital detector unit DDU being thereby paired with a corresponding one of the x-ray source array units SAU, each digital detector unit comprising an array of detector pixels extending over a predefined imaging area. Also provided in association with the x-ray source array units SAU1-SAU5 is a respective set of x-ray collimating units XCU1-XCU5, each x-ray collimating unit XCU being disposed between its associated x-ray source array unit SAU and the target volume, each x-ray collimating unit XCU being positioned closer to that x-ray source array unit SAU than to the target volume. Each x-ray collimating unit XCU is configured and dimensioned to collimate x-ray radiation from its respective x-ray source unit SAU onto the paired digital detector unit DDU.

For the example of FIG. 17-1 through FIG. 17-5, a set of five (5) tomosynthesis projection images are acquired by respective activation of the five SAU-DDU pairs. It is to be appreciated that as few as two SAU-DDU pairs and as many as 1000 SAU-DDU pairs can be provided, for acquiring 2-1000 tomosynthesis projection images, without departing from the scope of the present teachings. Although illustrated in FIG. 17-1 through FIG. 17-5 as being non-overlapping with each other, in other preferred embodiments neighboring ones of the digital detector units DDU1-DDU5 can be overlapping with each other (i.e., can share one or more digital detector pixels).

Figure 18:
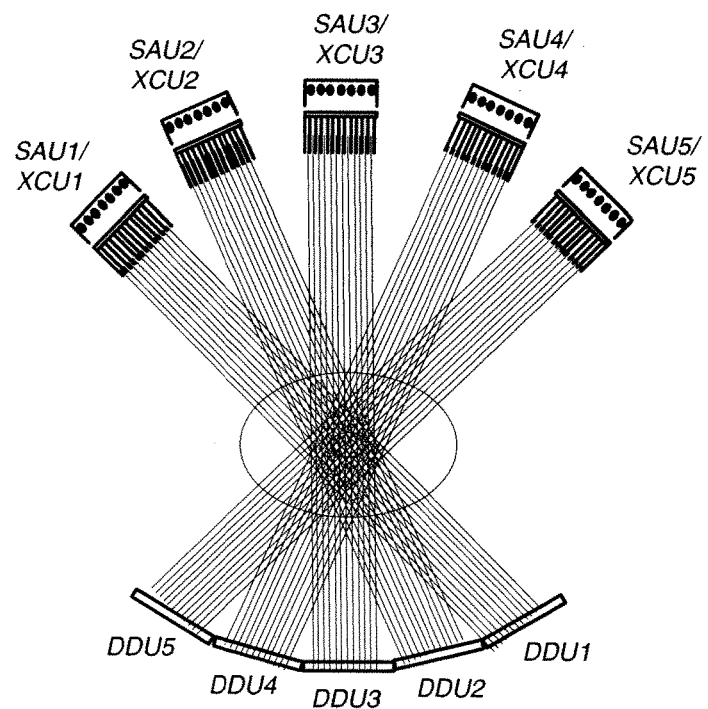
FIG. 18 illustrates acquiring a set of x-ray tomosynthesis projection images of a target volume according to a preferred embodiment in which (i) the digital detector units DDU1-DDU5 are non-overlapping with each other, and (ii) the x-ray source array units SAU and x-ray collimating units XCU are configured such that each separate x-ray source array unit illuminates only its paired digital detector unit DDU with primary x-rays, with no spillover of primary x-rays onto neighboring digital detector units.

FIG. 18 illustrates acquiring a set of x-ray tomosynthesis projection images of a target volume according to a preferred embodiment in which (i) the digital detector units DDU1-DDU5 are non-overlapping with each other, and (ii) the x-ray source array units SAU and x-ray collimating units XCU are configured such that each separate x-ray source array unit illuminates only its paired digital detector unit DDU with primary x-rays, with no spillover of primary x-rays onto neighboring digital detector units. Advantageously, for this preferred embodiment, all of the x-ray tomosynthesis projection images can be acquired simultaneously, which can be particularly useful for dynamic target tracking when used in conjunction with the radiation treatment system of FIG. 1, supra.

Figures 1, 19:
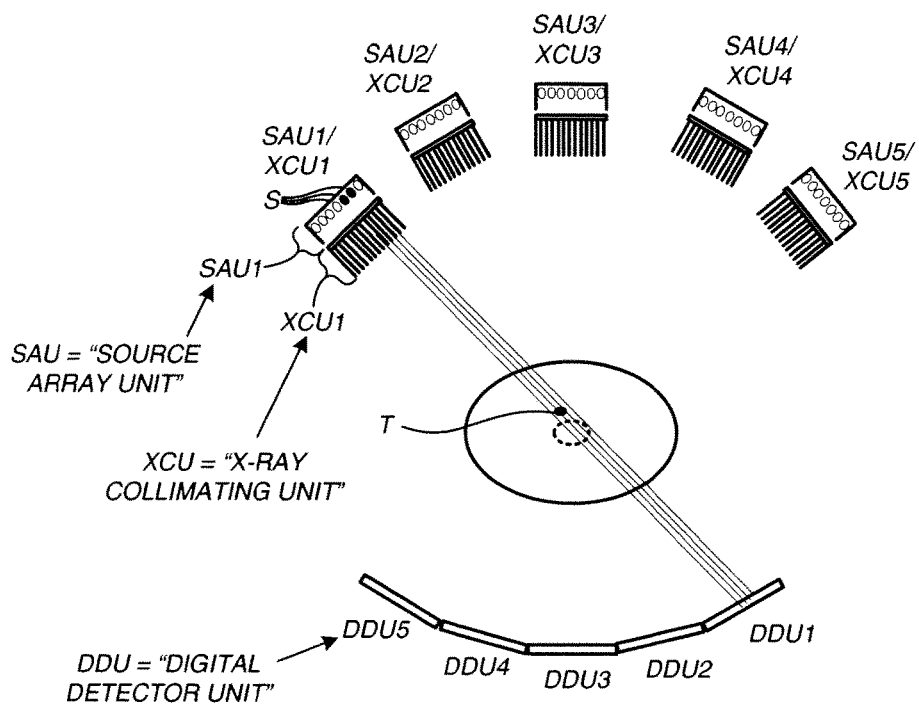
Figures 2, 19:
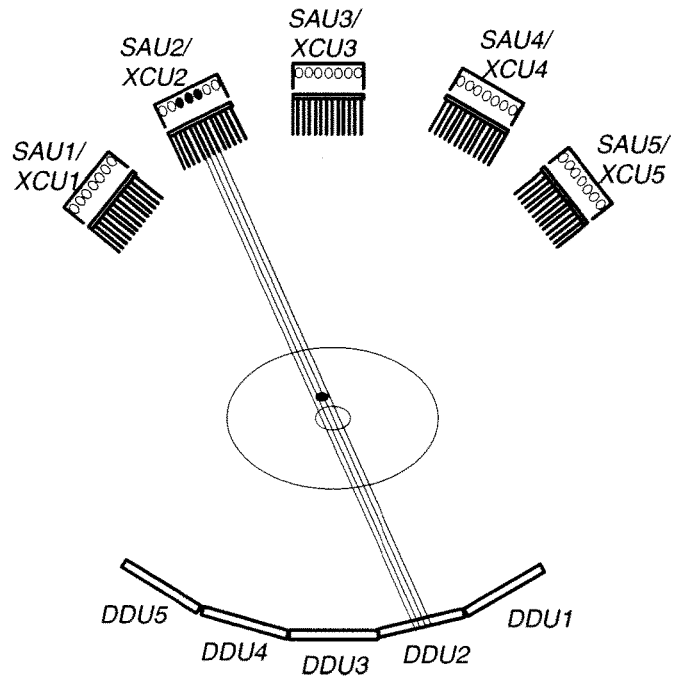
Figures 3, 19:
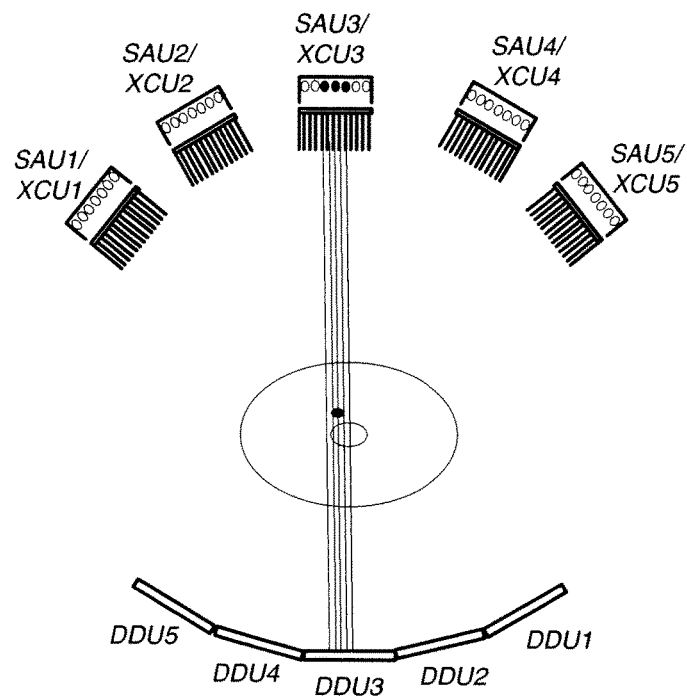
Figures 4, 19:
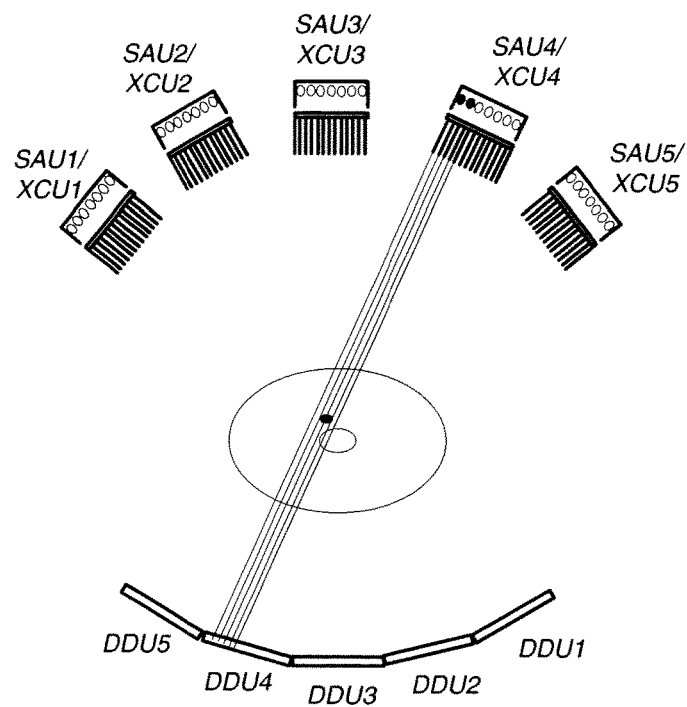
Figures 5, 19:
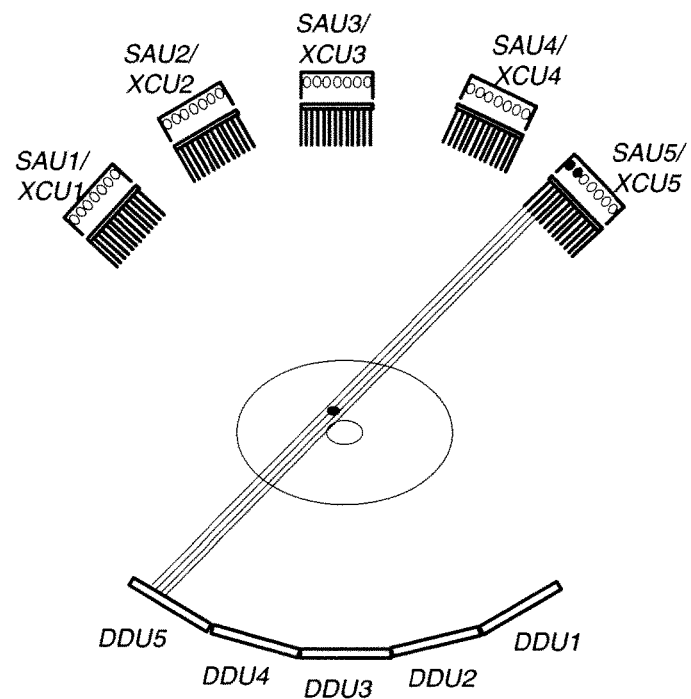

FIG. 19-1 through FIG. 19-5 illustrate acquiring a set of x-ray tomosynthesis projection images of a target structure T according to a preferred embodiment. The target structure T can be, for example, a target tumor needing treatment radiation that is positioned off-center relative to the tomosynthesis imaging system. Each x-ray source array/x-ray collimating unit pair (SAU/XCU) is configured to be capable of a first mode of operation in which x-ray radiation is adjustably collimated onto only a subgroup of detector pixels (i.e., only a portion of a predefined imaging area) of the paired digital detector unit DDU. Information is received that is indicative of the position of a target structure T, for example by virtue of a low-dose "pilot" tomosynthesis data set acquired using a second mode of operation similar to that of FIG. 18, supra. The x-ray source array units SAU are sequentially activated to acquire a set of x-ray tomosynthesis projection images. However, for each x-ray source array unit SAU, only the particular subgroup of x-ray sources whose projections onto the paired digital detector unit DDU are necessary to laterally encompass the target structure T are activated. The identity of the necessary subgroup of x-ray sources can be readily determined from the low-dose "pilot" tomosynthesis data set. Methods for generating tomosynthesis reconstructed image data from the x-ray tomosynthesis projections of FIG. 19-1 through FIG. 19-5 would be apparent to a person skilled in the art in view of the present disclosure.

Figure 20:
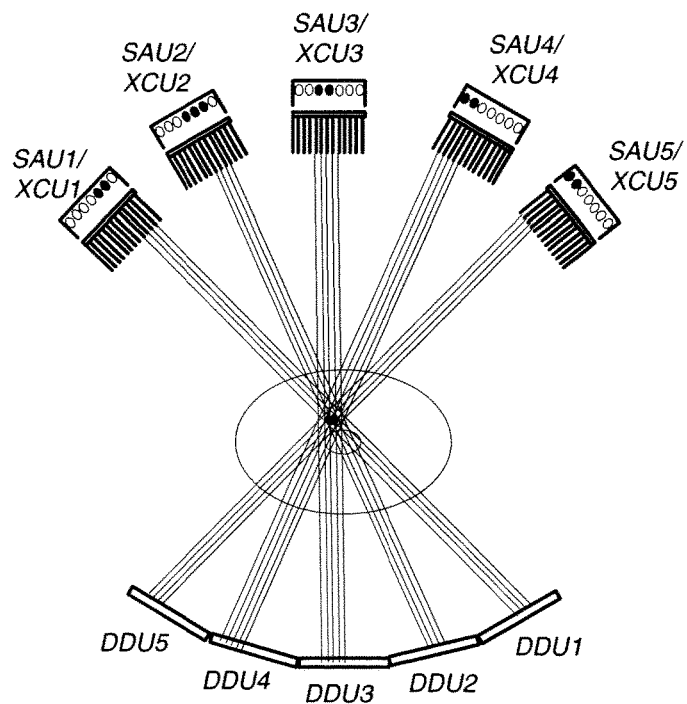
FIG. 20 illustrates acquiring a set of x-ray tomosynthesis projection images of a target volume according to a preferred embodiment similar to that of FIG. 19-1 through FIG. 19-5, except that all of the x-ray tomosynthesis projection images are acquired simultaneously.

FIG. 20 illustrates acquiring a set of x-ray tomosynthesis projection images of a target volume according to a preferred embodiment similar to that of FIG. 19-1 through FIG. 19-5, except that all of the x-ray tomosynthesis projection images are acquired simultaneously. Advantageously, when compared to a scenario in which each x-ray source unit comprises a single x-ray source that illuminates the entire predefined imaging area of the paired digital detector unit, the preferred embodiments of FIG. 19-1 through FIG. 19-5 and FIG. 20 can provide a similar-quality image at a substantial x-ray dose reduction. Alternatively, for a similar overall x-ray dose as would be applied to the patient by the single-source units, a higher-quality image can be obtained by increasing the power of the activated x-ray sources in the x-ray source array. In yet another alternative, for a similar overall x-ray dose as would be applied to the patient by the single-source units and for a similar image quality, the time rate of capture of respective x-ray tomosynthesis data sets can be increased (for example, acquiring an x-ray tomosynthesis data set every 5 seconds rather than every 15 seconds) for providing improved temporal accuracy in target tracking.

Figures 1, 21:
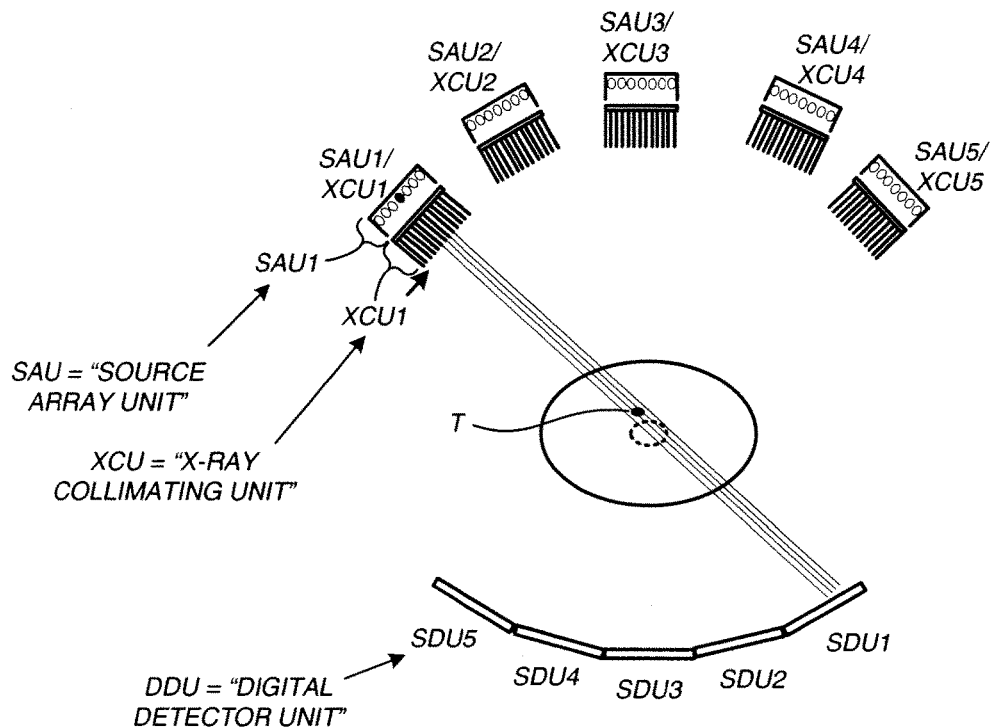
Figures 2, 21:
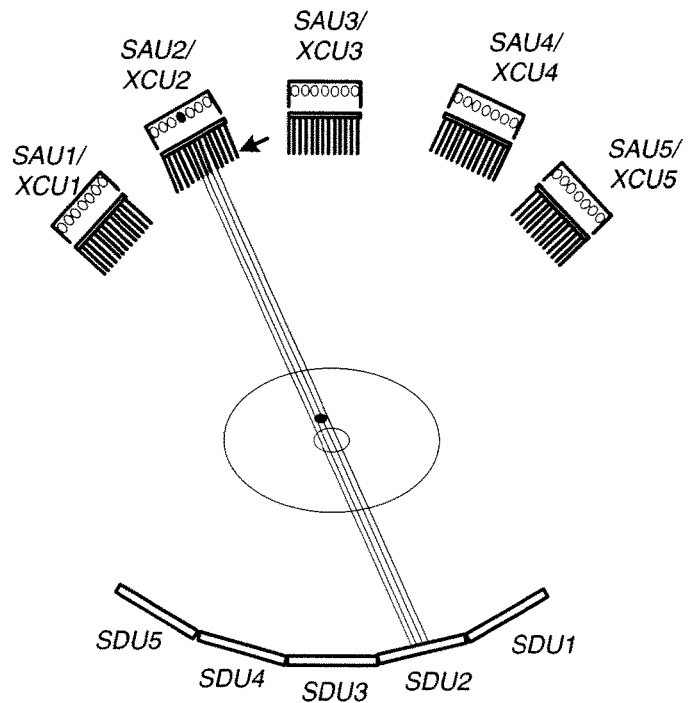
Figures 3, 21:
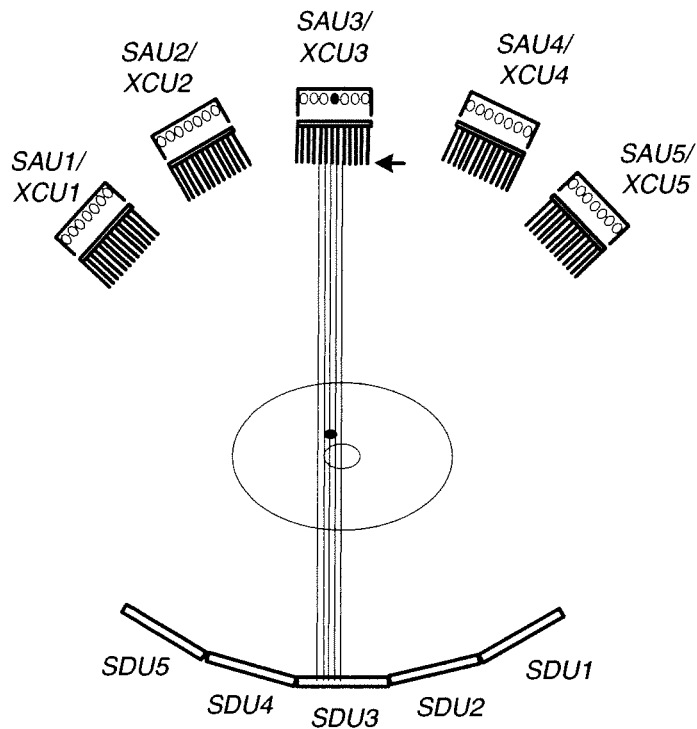
Figures 4, 21:
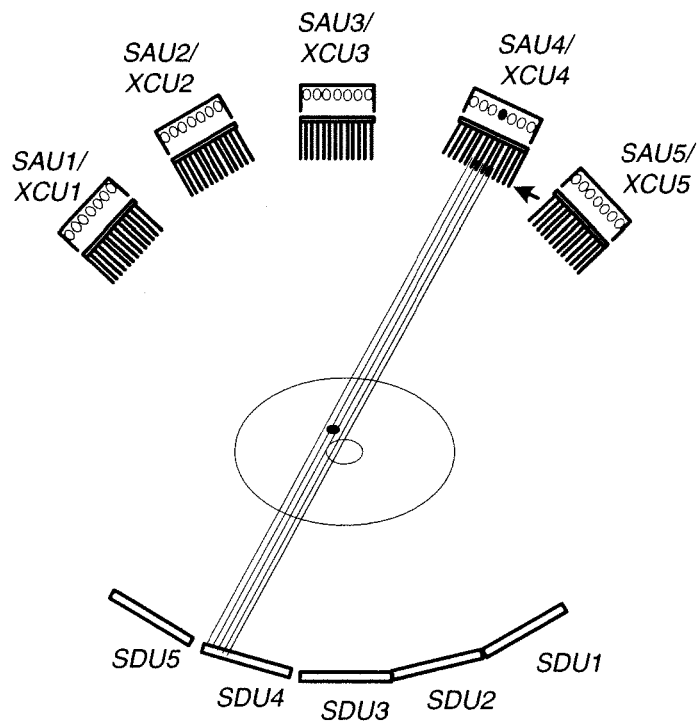
Figures 5, 21:
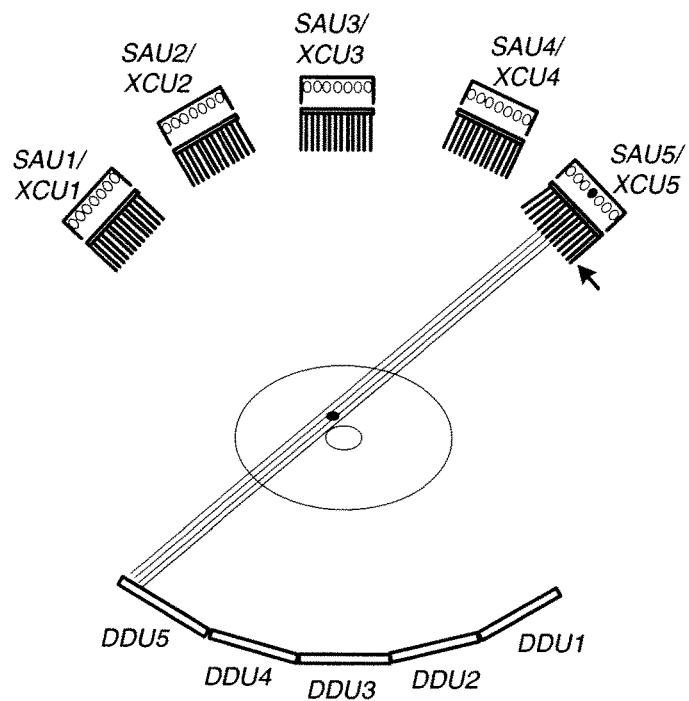
Figure 22:
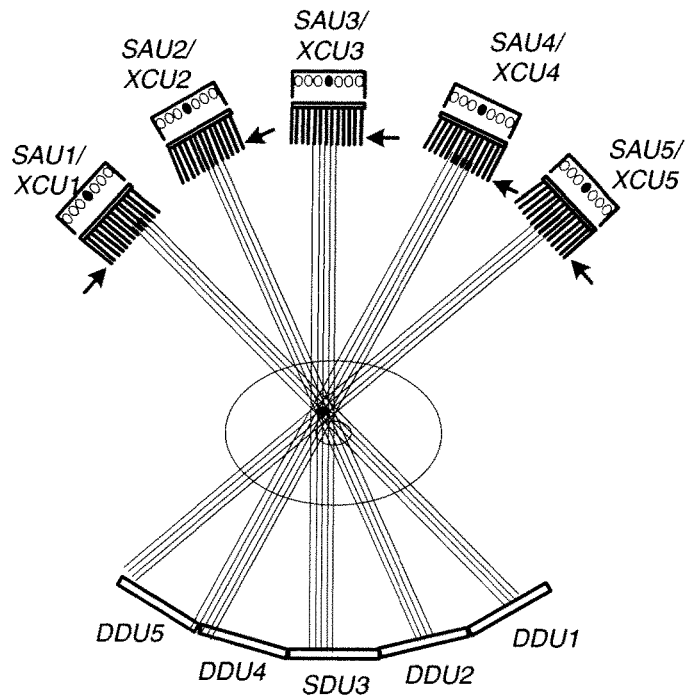
FIG. 22 illustrates acquiring a set of x-ray tomosynthesis projection images of a target volume according to a preferred embodiment similar to that of FIG. 21-1 through FIG. 21-5, except that all of the x-ray tomosynthesis projection images are acquired simultaneously.

FIG. 21-1 through FIG. 21-5 illustrates acquiring a set of x-ray tomosynthesis projection images of a target volume according to a preferred embodiment that is functionally similar to that of FIG. 19-1 through FIG. 19-5, except that the selective localized illumination of digital detectors is achieved by mechanical control of the beamsteering angle of the x-ray collimating units XCU while the subset of x-ray sources within each x-ray source array unit SAU is kept constant. FIG. 22 illustrates acquiring a set of x-ray tomosynthesis projection images of a target volume according to a preferred embodiment similar to that of FIG. 21-1 through FIG. 21-5, except that all of the x-ray tomosynthesis projection images are acquired simultaneously. Any of a variety of different combinations of selective target illumination configurations and strategies, as exemplified by FIG. 19-1 through FIG. 22, can be used and are within the scope of the present teachings.

FIGS. 23A-23D illustrate an inverse geometry tomosynthesis imaging system 2301 that can be used in tomosynthesis imaging according to a preferred embodiment. Inverse geometry tomosynthesis imaging system 2301 comprises a digital detector array 2302, an x-ray source array 2304 having a collimation device 2306 closely positioned therenear or integral therewith. The digital detector array 2302 is positioned opposite the x-ray source array 2304 and collimation device 2306 relative to the target volume V, which includes a target structure T. Preferably, the x-ray source array comprises a computer-steerable electron beam and a spatial arrangement of metallic targets, each metallic target becoming an active x-ray focal spot when the electron beam is steered onto it, such as one or more such devices developed by Triple Ring Technologies, supra. However, other types of x-ray source arrays, such as cold-cathode source arrays, can alternatively be used.

In one preferred embodiment, the inverse geometry tomosynthesis imaging system 2301 can be implemented in conjunction with the robotic arm-based IGRT system 400 of FIG. 4, supra, with the x-ray source array 2304 taking the position of x-ray source array 406 and the digital detector array 2302 taking the position of the detector array 412. In one example, the x-ray source array 2304/406 can be positioned in or near the floor of the treatment vault, positioned beneath the treatment couch C by about 0.5 m-1.0 m, while the digital detector array 2302/412 can be positioned in or near the ceiling of the treatment vault, positioned above the treatment couch C by about 1.0 m-2.0 m. In another preferred embodiment, further to the configuration of FIG. 4, supra, there are two similar inverse geometry tomosynthesis imaging systems provided that are oriented in a stereoscopic configuration relative to the treatment volume, the first being implemented by the source/detector pair 406/412 and the second being implemented by the source/detector pair 408/410. Optionally, the two inverse geometry tomosynthesis imaging systems can have different x-ray energies (e.g., 80 keV and 140 keV, respectively) for providing a dual-energy capability. In another preferred embodiment, the arrangement of FIG. 5 is used in which the stereoscopic angle is subtended along the head-to-toe direction of the treatment couch C. For clarity of disclosure, only a single inverse geometry tomosynthesis imaging system 2301 is illustrated in the example of FIGS. 23A-23D.

Figure 23A:
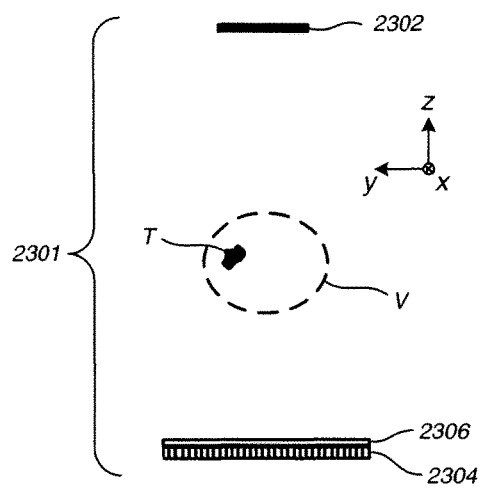
FIGS. 23A-23D illustrate an inverse geometry tomosynthesis imaging system 2301 that can be used in tomosynthesis imaging according to a preferred embodiment.
Figure 23B:
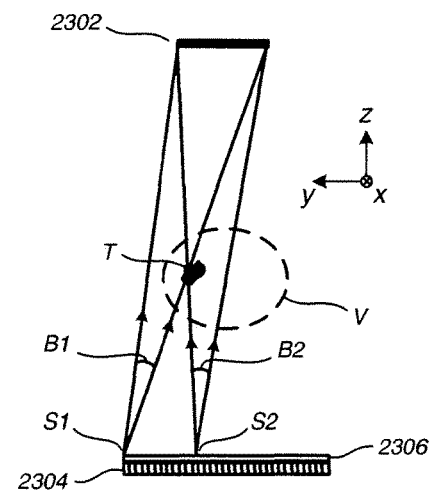

The inverse geometry tomosynthesis imaging system 2301 is characterized in that the digital detector array 2302 is smaller than the x-ray source array 2304, at least with respect to the direction of a tomosynthesis imaging arc to be subtended in the tomosynthesis imaging process. Preferably, the x-ray source array 2304 is large enough so as to be able to subtend an appreciably large tomosynthesis imaging arc relative to a point in the target volume. By way of example and not by way of limitation, for the discussed IGRT implementation similar to that of FIG. 4, supra, the x-ray source array 2304/406 should be at least about 20 cm in length along the tomosynthesis imaging arc if separated from the treatment couch by 0.5 m-1.0 m, with better results being obtained for longer x-ray source array dimensions. Each x-ray source within the x-ray source array 2304 is collimated by the collimation device 2306 such that the x-ray beam emanating therefrom is directed at the digital detector array 2302 and is only wide enough to cover the spatial extent of the digital detector array 2302. This is illustrated in FIG. 23B, which shows a collimated beam B1 manating from an x-ray source S1 and a collimated beam B2 emanating from an x-ray source S2.

Inverse geometry configurations in the context of CT imaging are discussed in U.S. Pat. No. 7,734,004B2 and US2006/021005A1, each of which is incorporated by reference herein. Algorithms for tomosynthesis imaging based on inverse geometry configurations are also known in the art and, accordingly, implementation of the tomosynthesis imaging and reconstruction methods set forth herein would be achievable by a person skilled in the art in view of the present disclosure without undue experimentation. Inverse geometry configurations can provide certain advantages in tomographic imaging, with one important advantage being reduced scatter in comparison to conventional configurations having larger detectors.

In accordance with one preferred embodiment, tomosynthesis imaging of a target structure contained within a larger target volume is provided using an inverse geometry tomosynthesis imaging system in a manner that provides at least one of increased image quality and reduced image dose, by virtue of actuating only a subset of the x-ray sources in the x-ray source array that are necessary to image the target structure in the inverse-geometry tomosynthesis imaging process based on a known or expected location of the target structure. It has been found particularly useful to apply the method in the context of image-guided radiation treatment systems, and still more particularly in the intrafraction tracking of a target structure, such as a tumor, that may be moving during the treatment fraction. It is desirable to locate the tumor with a high degree of precision during the treatment fraction, while at the same time avoiding the excess introduction of ionizing kV imaging radiation into the target volume at locations away from the tumor location.

Figure 23C:
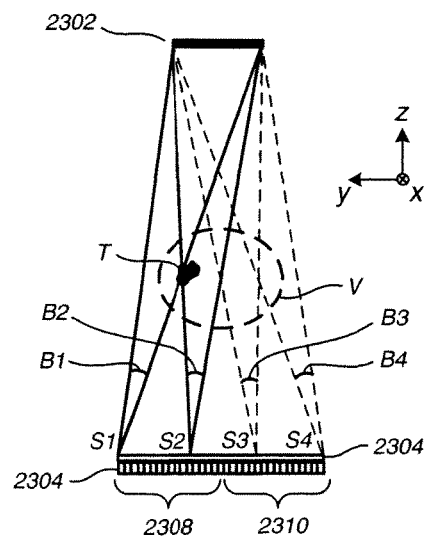
Figure 23D:
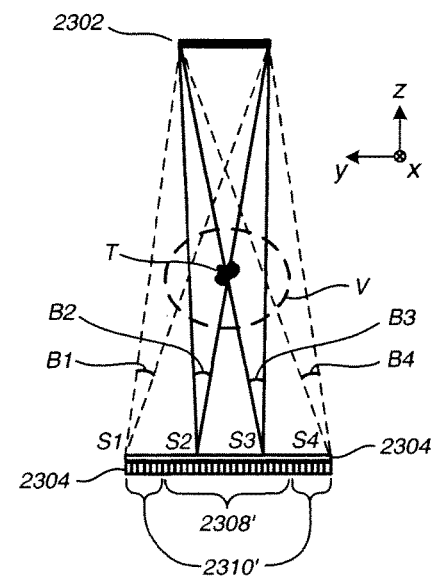

Referring now to FIGS. 23C-23D, it can be seen in FIG. 23C that the target structure T is in a first location and is encountered by the collimated beams B1 from source S1 and B2 from source S2 on their way to the digital detector array 2302, but is not encountered by the collimated beams B3 from source S3 or B4 from source S4 on their way to the digital detector array 2302. Accordingly, the tomosynthesis projection images based on radiation from the sources S3 and S4 would not be contributing any information relevant to the target structure T in any tomosynthesis reconstructed data set. Likewise, it can be seen in FIG. 23D that the target structure T, which is now in a different location within the target volume V, is encountered by the collimated beams B2 from source S2 and B3 from source S3, but is not encountered by the collimated beams B1 from source S1 or B4 from source S4, and thus the tomosynthesis projection images based on radiation from the sources S1 and S4 would not be contributing any relevant information in the tomosynthesis reconstructed data. According to a preferred embodiment, knowledge of the particular target structure location at any particular time is used in the inverse geometry x-ray tomosynthesis imaging process to "turn off" any x-ray sources in the source array whose collimated beams do not pass through or near that structure (e.g., the subset 2310 in FIG. 23C and the subset 2310' in FIG. 23D), and to only activate those x-ray sources whose collimated beams do pass through or near that structure (e.g., the subset 2308 in FIG. 23C and the subset 2308' in FIG. 23D).

Figure 24:
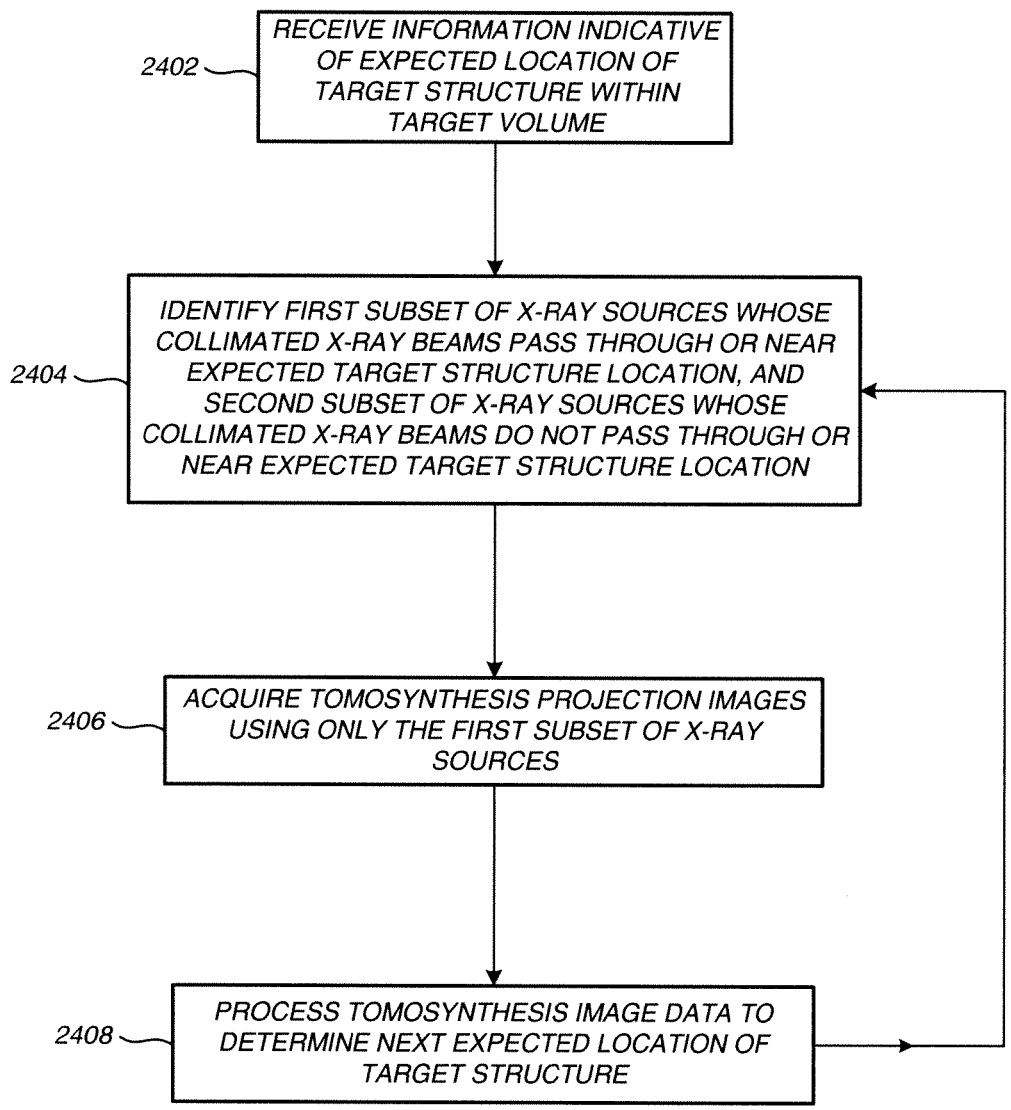
FIG. 24 illustrates inverse geometry tomosynthesis imaging of a target structure located within a target volume according to a preferred embodiment.

FIG. 24 illustrates inverse geometry tomosynthesis imaging of a target structure located within a target volume according to a preferred embodiment. At step 2402, information is received that is indicative of an expected location of the target structure within the target volume at a first point in time, i.e., at the time at which the tomosynthesis image volume will be acquired. This expected location information can be derived from a pilot tomosynthesis image data set acquired using all of the x-ray sources in the source array 2304, or alternatively from a previous low-dose tomosynthesis imaging iteration. As another alternative, the expected location information can be derived from 2D pilot x-ray images acquired using one of the x-ray sources, or from a very sparse set of tomosynthesis projection images acquired using only a very small subset (for example, every fifth x-ray source or every tenth x-ray source) of the x-ray sources. The use of a stereoscopic implementation in which there are two separate inverse geometry tomosynthesis imaging systems can be especially helpful in providing a low-dose prediction of the target structure location from 2D pilot x-ray images or sparse tomosynthesis projection image sets. Optionally, additional information from external sensing systems, such as the SYNCHRONY® respiratory tracking system, supra, can be incorporated into the computation of the expected target structure location.

At step 2404, the expected location information is processed in conjunction with the known imaging geometry of the inverse geometry tomosynthesis imaging system to identify a first subset of the x-ray sources whose collimated x-ray beams would pass through or near the target structure at the first point in time, as well as a second subset of said x-ray sources whose collimated x-ray beams would not pass through or near the target structure at the first point in time. At step 2406, a first plurality of x-ray tomosynthesis projection images of the target structure is acquired during a first tomosynthesis imaging interval that includes the first point in time, using only the first subset of x-ray sources and not the second subset of x-ray sources. At step 2408, in addition to using the acquired tomosynthesis image data for its intended purpose, such as for reconstructing a tomosynthesis image volume therefrom and guiding the delivery of treatment radiation to the target structure, the acquired tomosynthesis image data can be further or otherwise processed to compute a next expected location of the target structure, which information can then be used again at step 2404 for identifying the next subset of x-ray sources to use for the next set of tomosynthesis projection images, and so on.

Whereas many alterations and modifications of the present invention will no doubt become apparent to a person of ordinary skill in the art after having read the foregoing description, it is to be understood that the particular embodiments shown and described by way of illustration are in no way intended to be considered limiting.

What is claimed is:

1. A method of image guided radiation treatment of a treatment target within an internal target volume of a patient, comprising:
   providing an image-guided radiation treatment (IGRT) apparatus having first and second x-ray tomosynthesis source-detector pairs positioned to acquire tomosynthesis projection images over first and second projection angle ranges, respectively, said first and second source-detector pairs being at a non-zero angle with respect to each other;
   acquiring first and second sets of tomosynthesis projection images of the target volume at distinct first and second x-ray energy levels, respectively, using said first and second x-ray tomosynthesis source-detector pairs, respectively;

respectively processing said first and second sets of tomosynthesis projection images to generate respective first and second tomosynthesis reconstructed image sets of the target volume;

processing, by a processing device, said first and second tomosynthesis reconstructed image sets in conjunction with each other on a locationwise basis within the target volume to generate a dual-energy processed image set; and delivering treatment radiation to the treatment target within the target volume based at least in part on said dual-energy processed image set.

2. The method of claim 1, said first and second x-ray tomosynthesis source-detector pairs being disposed relative to each other and to the target volume such that no primary x-ray passing through the target volume from the first source impinges upon the second detector and no primary x-ray passing through the target volume from the second source impinges upon the first detector, wherein said first and second sets of tomosynthesis projection images are acquired simultaneously.

3. The method of claim 1, wherein said first and second x-ray tomosynthesis source-detector pairs are symmetrically disposed relative to a central sagittal plane of the patient.

4. The method of claim 1, wherein said first and second sets of tomosynthesis projection images are each acquired, and said corresponding dual-energy processed image sets are generated, at periodic time intervals longer than a physiological movement cycle of the patient;
wherein said first and second sets of tomosynthesis projection images are each periodically acquired at times corresponding to a common phase of the physiological movement cycle;
wherein said IGRT apparatus further comprises a target movement sensing system that processes continuously monitored external patient movement data in conjunction with a correlation model to predictively compute target volume movement during the physiological movement cycle; and
wherein said dual-energy processed image set is used to update said correlation model for each said periodic time interval.

5. The method of claim 1, wherein said first and second sets of tomosynthesis projection images are each acquired at periodic time intervals, wherein said first x-ray energy level alternates between a low x-ray energy level and a high x-ray energy level at said respective acquisition times, and wherein said second x-ray energy level alternates oppositely between the high x-ray energy level and the low x-ray energy level at the respective acquisition times.

6. The method of claim 1, wherein said processing said first and second tomosynthesis reconstructed image sets in conjunction with each other comprises generating a dual-energy subtraction image set.

7. The method of claim 1, where each of said first and second x-ray tomosynthesis sources comprises a digitally addressable x-ray source array.

8. An image-guided radiation treatment (IGRT) apparatus to provide image guided radiation treatment of a treatment target within an internal target volume of a patient, the IGRT apparatus comprising:
first and second x-ray tomosynthesis source-detector pairs positioned to acquire tomosynthesis projection images over first and second projection angle ranges, respectively, the first and second source-detector pairs being at a non-zero angle with respect to each other;
a processing device, operatively coupled with the first and second x-ray tomosynthesis source-detector pairs, the processing device to:
acquire first and second sets of tomosynthesis projection images of the target volume at distinct first and second x-ray energy levels, respectively, using the first and second x-ray tomosynthesis source-detector pairs, respectively;
respectively process the first and second sets of tomosynthesis projection images to generate respective first and second tomo synthesis reconstructed image sets of the target volume;
process the first and second tomosynthesis reconstructed image sets in conjunction with each other on a locationwise basis within the target volume to generate a dual-energy processed image set; and
control delivery of treatment radiation to the treatment target within the target volume based at least in part on the dual-energy processed image set.

9. The IGRT apparatus of claim 8, wherein the first and second x-ray tomosynthesis source-detector pairs being disposed relative to each other and to the target volume such that no primary x-ray passing through the target volume from the first source impinges upon the second detector and no primary x-ray passing through the target volume from the second source impinges upon the first detector, wherein the processing device to simultaneously acquire the first and second sets of tomosynthesis projection images.

10. The IGRT apparatus of claim 8, wherein the first and second x-ray tomosynthesis source-detector pairs are symmetrically disposed relative to a central sagittal plane of a patient couch.

11. The IGRT apparatus of claim 8, wherein the first and second sets of tomosynthesis projection images are each acquired, and the corresponding dual-energy processed image sets are generated, at periodic time intervals longer than a physiological movement cycle of the patient; and
wherein the first and second sets of tomosynthesis projection images are each periodically acquired at times corresponding to a common phase of the physiological movement cycle.

12. The IGRT apparatus of claim 11, further comprising a target movement sensing system to process continuously monitored external patient movement data in conjunction with a correlation model to predictively compute target volume movement during the physiological movement cycle, and wherein the dual-energy processed image set is used to update the correlation model for each said periodic time interval.

13. The IGRT apparatus of claim 8, wherein the processing device further to:
acquire the first and second sets of tomosynthesis projection images at periodic time intervals;
alternate the first x-ray energy level between a low x-ray energy level and a high x-ray energy level at the respective acquisition times; and
alternate the second x-ray energy level oppositely between the high x-ray energy level and the low x-ray energy level at the respective acquisition times.

14. The IGRT apparatus of claim 8, wherein to process the first and second tomosynthesis reconstructed image sets in conjunction with each other, the processing device to generate a dual-energy subtraction image set.

15. The IGRT apparatus of claim 8, where each of the first and second x-ray tomosynthesis sources comprises a digitally addressable x-ray source array.

16. A non-transitory machine readable medium comprising instructions that when executed cause a processing device of an image-guided radiation treatment (IGRT) apparatus to:

acquire first and second sets of tomosynthesis projection images using first and second x-ray tomosynthesis source-detector pairs positioned to acquire tomosynthesis projection images over first and second projection angle ranges, respectively, the first and second source-detector pairs being at a non-zero angle with respect to each other, wherein to acquire the processing device to acquire first and second sets of tomosynthesis projection images of a target volume at distinct first and second x-ray energy levels, respectively, using the first and second x-ray tomosynthesis source-detector pairs, respectively;

respectively process the first and second sets of tomosynthesis projection images to generate respective first and second tomo synthesis reconstructed image sets of the target volume;

process, by the processing device, the first and second tomosynthesis reconstructed image sets in conjunction with each other on a locationwise basis within the target volume to generate a dual-energy processed image set; and control delivery of treatment radiation to the treatment target within the target volume based at least in part on the dual-energy processed image set.

17. The non-transitory machine readable medium of claim 16, wherein the processing device to simultaneously acquire the first and second sets of tomosynthesis projection images.

18. The non-transitory machine readable medium of claim 17, wherein the first and second sets of tomosynthesis projection images are each acquired, and the corresponding dual-energy processed image sets are generated, at periodic time intervals longer than a physiological movement cycle of the patient; and wherein the first and second sets of tomosynthesis projection images are each periodically acquired at times corresponding to a common phase of the physiological movement cycle.

19. The non-transitory machine readable medium of claim 18, wherein the processing device further to:

process continuously monitored external patient movement data in conjunction with a correlation model to predictively compute target volume movement during the physiological movement cycle; and update the correlation model for each said periodic time interval using the dual-energy processed image set.

20. The non-transitory machine readable medium of claim 17, wherein the processing device further to:

acquire the first and second sets of tomosynthesis projection images at periodic time intervals;

alternate the first x-ray energy level between a low x-ray energy level and a high x-ray energy level at the respective acquisition times; and alternate the second x-ray energy level oppositely between the high x-ray energy level and the low x-ray energy level at the respective acquisition times.

21. The non-transitory machine readable medium of claim 18, wherein to process the first and second tomosynthesis reconstructed image sets in conjunction with each other, the processing device to generate a dual-energy subtraction image set.

\* \* \* \* \*